(12) United States Patent
Murphy

(10) Patent No.: US 8,962,913 B2
(45) Date of Patent: Feb. 24, 2015

(54) HUMANIZED IL-7 RODENTS

(71) Applicant: Regeneron Pharmaceuticals, Inc., Tarrytown, NY (US)

(72) Inventor: Andrew J. Murphy, Croton-on-Hudson, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 13/795,765

(22) Filed: Mar. 12, 2013

(65) Prior Publication Data

US 2013/0340104 A1 Dec. 19, 2013

Related U.S. Application Data

(60) Provisional application No. 61/660,976, filed on Jun. 18, 2012, provisional application No. 61/740,074, filed on Dec. 20, 2012.

(51) Int. Cl.
*A01K 67/027* (2006.01)
*C12N 15/90* (2006.01)
*C07K 14/54* (2006.01)

(52) U.S. Cl.
CPC ......... *A01K 67/0278* (2013.01); *C07K 14/5418* (2013.01); *A01K 2217/052* (2013.01); *A01K 2217/07* (2013.01); *A01K 2217/072* (2013.01); *A01K 2227/105* (2013.01); *A01K 2267/0331* (2013.01); *A01K 2267/0387* (2013.01); *A01K 2267/0393* (2013.01)
USPC .............................................. 800/18; 800/21

(58) Field of Classification Search
CPC ................ A01K 2227/105; A01K 2267/0331; A01K 2267/0387; A01K 2217/07; A01K 2217/072; A01K 67/0278; C12N 15/8509; A61K 38/19
USPC .................................................... 800/18, 21
See application file for complete search history.

(56) References Cited

U.S. PATENT DOCUMENTS 7,759,541 B2    7/2010    Wolf et al.

FOREIGN PATENT DOCUMENTS

GB          2434578 A      8/2007

OTHER PUBLICATIONS

Silva et al. (2011) Cancer Res., vol. 71, 4780-4789.*
Willinger et al. (2011) Trends in Immunology, vol. 32(7), 321-327.*
Lupton et al. (1990) J. Immunol., vol. 144, 3592-3601.*
Clark et al. (2003) Nature Reviews: Genetics. vol. 4, 825-833.*
Munoz et al. (2009) Stem Cell Rev. and Rep., vol. 5, 6-9.*
Wheeler (2001) Theriogenology. vol. 56, 1345-1369.*
Prelle et al. (2002) Anat. Histol. Embryol., vol. 31, 169-186.*
Niemann et al (2005) Rev. Sci, Tech. Off. Int. Spiz. vol. (24), 285-298.*
Rich et al. (1993). J. Exp. Med., vol. 177, 305-316.*
Fisher et al. (1993) Leukemia, vol. 7(2), 566-568.*
Watanabe et al. (1998) J. Exp. Med., vol. 187, 389-402.*
Rongvaux et al. (2011) PNAS, vol. 108(6), 2378-2383.*
Willinger et al. (2011) PNAS, vol. 108, 2390-2395.*
Anderson et al. (2008) Nat. Immunol., vol. 9(4), 353-359.*
Carpenter et al. (2014) Nat. Reviews, vol. 14, 361-376.*
Foss et al., "Frequent Expression of IL-7 Gene Transcripts in Tumor Cells of Classical Hodgkin's Disease," American Journal of Pathology, 146(1): 33-39, 1995.
Freeden-Jeffry et al., "Lymphopenia in Interleukin (IL)-7 Gene-deleted Mice Identifies IL-7 as a Nonredundant Cytokine," J. Exp. Med., 181: 1519-1526, 1995.
Fry et al., "A potential role for interleukin-7 in T-cell homeostasis," Blood, 97: 2983-2990, 2001.
Fry et al., "IL-7 comes of age," Blood, 107(1): 2587-2588, 2006.
Fry et al., "The Many Faces of IL-7: From Lymphopoiesis to Peripheral T Cell Maintenance," Journal of Immunology, 174: 6571-6576, 2005.
Fry, et al., "Interleukin-7: from bench to clinic," Blood, 99(11): 3892-3904, 2002.
Geiselhart et al., "IL-7 Administration Alters the CD4: CD8 Ratio, Increases T Cell Numbers, and Increases T Cell Function in the Absence of Activation," The Journal of Immunology, 166: 3019-3027, 2001.
Goodwin et al., "Human interleukin 7: Molecular cloning and growth factor activity on human and murine B-lineage cells," Proc. Natl. Acad. Sci. USA, 86: 302-306, 1989.
Guimond et al., "Cytokine Signals in T-Cell Homeostasis," J. Immunother, 28: 289-294, 2005.
Jacobs et al., "IL-7 Is Essential for Homeostatic Control of T Cell Metabolism In Vivo," The Journal of Immunology, 184: 3461-3469, 2010.
Kang et al., "Defective Development of γ/δ T Cells in Interleukin 7 Receptor-deficient Mice Is Due to Impaired Expression of T Cell Receptor γ Genes," J. Exp. Med., 190(7): 973-982, 1999.
Kieper et al., "Overexpression of Interleukin (IL)-7 Leads to IL-15-independent Generation of Memory Phenotype $CD8^+T$ Cells," J. Exp. Med., 195(12): 1533-1539, 2002.
Lent et al., "IL-7 Enhances Thymic Human T Cell Development in "Human Immune System" $Rag2^{-/-}IL-2R\gamma_c^{-/-}$ Mice without Affecting Peripheral T Cell Homeostasis," The Journal of Immunology, 183: 7645-7655, 2009.
Lombard-Platet et al., "Expression of Functional MHC Class II Molecules by a Mouse Pro-B Cell Clone," Developmental Immunology, 4: 85-92, 1995.
Lupton et al., "Characterization of the Human and Murine IL-7 Genes," The Journal of Immunology, 144(9): 3592-3601, 1990.

(Continued)

*Primary Examiner* — Anne Marie S Wehbe
(74) *Attorney, Agent, or Firm* — Scully, Scott, Murphy & Presser, P.C.

(57) ABSTRACT

Genetically modified non-human animals comprising a human or humanized interleukin-7 (IL-7) gene. Cells, embryos, and non-human animals comprising a human or humanized IL-7 gene. Rodents that express human or humanized IL-7 protein. Genetically modified mice that comprise a human or humanized IL-7-encoding gene in their germline, wherein the human or humanized IL-7-encoding gene is under control of endogenous mouse IL-7 regulatory sequences.

6 Claims, 2 Drawing Sheets

(56) References Cited

OTHER PUBLICATIONS

Mahajan et al., "Homeostasis of T Cell Diversity," Cellular & Molecular Immunology, 2(1): 1-10, 2005.
Mazzucchelli et al., "Interleukin-7 receptor expression: intelligent design," Nature, 7: 144-154, 2007.
Mertsching et al., "IL-7 transgenic mice: analysis of the role of IL-7 in the differentiation of thymocytes in vivo and in vitro," International Immunology, 7(3): 401-414, 1995.
Munitic et al., "Dynamic regulation of IL-7 receptor expression is required for normal thymopoiesis," Blood, 104: 4165-4172, 2004.
Murphy et al., "Antitumor Effects of Interleukin-7 and Adoptive Immunotherapy on Human Colon Carcinoma Xenografts," J. Clin. Invest., 92: 1918-1924, 1993.
O'Connell et al., "Lentiviral Vector Delivery of Human Interleukin-7 (hIL-7) to Human Immune System (HIS) Mice Expands T Lymphocyte Populations," PLoS ONE, 5(8): 1-11, 2010.
Pleiman et al., "Organization of the Murine and Human Interleukin-7 Receptor Genes: Two mRNAs Generated by Differential Splicing and Presence of a Type I-Interferon-Inducible Promoter," Molecular and Cellular Biology, 11(6): 3052-3059, 1991.
Repass et al., "IL7-hCD25 and IL7-Cre BAC Transgenic Mouse Lines: New Tools for Analysis of IL-7 Expressing Cells," Genesis 47: 281-287, 2009.
Rich et al., "Cutaneous Lymphoproliferation and Lymphomas in Interleukin 7 Transgenic Mice," J. Exp. Med., 177: 305-316, 1993.
Samaridis et al., "Development of lymphocytes in intereleukin 7-transgenic mice," Eur. J. Immunol., 21: 453-460, 1991.
Schluns et al., "Interleukin-7 mediates the homeostasis of naive and memory CD8T cells in vivo," Nature Immunology, 1(5): 426-432, 2000.
Silva et al., "IL-7 Contributes to the Progression of Human T-cell Acute Lymphoblastic Leukemias," Cancer Research, 71(14): 4780-4789, 2011.
Tan et al., "IL-7 is critical for homeostatic proliferation and survival of naïve T cells," PNAS, 98(15): 8732-8737, 2001.
Uehira et al., "Immunologic Abnormalities Exhibited in IL-7 Transgenic Mice with Dermatitis," J. Invest Dermatol 110: 740-745, 1998.
Uehira et al., The development of dermatitis infiltrated by γδ T cells in IL-7 transgenic mice, International Immunology, 5(12): 1619-1627, 1993.
Van De Wiele et al., "Impaired thymopoiesis in interleukin-7 receptor transgenic mice is not corrected by Bcl-2," Cellular Immunology, 250: 31-39, 2007.
Watanabe et al., "Interleukin 7 Transgenic Mice Develop Chronic Colitis with Decreased Interleukin 7 Protein Accumulation in the Colonic Mucosa," J. Exp. Med., 187(3): 389-402, 1998.
Williams, et al., "IL-7 Overexpression in Transgenic Mouse Keratinocytes Causes a Lymphoproliferative Skin Disease Dominated by Intermediate TCR Cells," The Journal of Immunology, 159: 3044-3056, 1997.
Campbell et al., "Neurologic disease induced in transgenic mice by cerebral overexpression of interleukin 6," Proc. Natl. Acad. Sci. USA, 90:10061-10065, 1993.
Dimitris et al., "The Pathophysiologic Roles of Interleukin-6 in Human Disease," Ann Intern Med., 128: 127-137, 1998.
Eisenbarth et al., "Development and Characterization of a Human IL-7 Transgenic Humanized Mouse Model," iwhm2, 2nd International Workshop on Humanized Mice, Program & Abstract Book, Sint Olofskapel, Amsterdam, The Netherlands, Apr. 3-6, 2009, Abstract #19.
Fattori et al., "IL-6 Expression in Neurons of Transgenic Mice Causes Reactive Astrocytosis and Increase in Ramified Microglial Cells but no Neuronal Damage," European Journal of Neuroscience, 7: 2441-2449, 1995.
Fattori, et al., "Development of Progressive Kidney Damage and Myeloma Kidney in Interleukin-6 Transgenic Mice," Blood, 83(9): 2570-2579, 1994.
Goya et al., "Sustained interleukin-6 signalling leads to the development of lymphoid organ-like structures in the lung," Journal of Pathology, 200: 82-87, 2003.
Heinrich et al., "Interleukin-6 and the acute phase response," Biochem. J., 265: 621-636, 1990.
Hirano et al., "Biological and clinical aspects of interleukin 6," Immunology, 11: 443-449, 1990.
Hirano et al., "Complementary DNA for a novel human interleukin (BSF-2) that induces B lymphocytes to produce immunoglobulin," Nature, 324: 73-76, 1986.
Hirano et al., Purification to homogeneity and characterization of human B-cell differentiation factor (BCDF or BSFp-2), Proc. Natl. Acad. Sci. USA, 82: 5490-5494, 1985.
Hirota et al., "Continuous activation of gp130, a signal-transducing receptor component for interleukin 6-related cytokines, causes myocardial hypertrophy in mice," Proc. Natl. Acad. Sci. USA, 92: 4862-4866, 1995.
International Search Report for PCT/US2012/062379 (5 pages), May 3, 2013.
Keller et al., "Molecular and Cellular Biology of Interleukin-6 and its Receptor," Frontiers in Bioscience, 1: 340-357, 1996.
Kishimoto, Tadamitsu, "IL-6: from its discovery to clinical applications," International Immunology, 22(5): 347-352, 2010.
Kishimoto, Tadamitsu, "The Biology of Interleukin-6," Blood, 74(1): 1-10, 1989.
Kovalchuk et al., "IL-6 transgenic mouse model for extraosseous plasmacytoma," PNAS, 99(3): 1509-1514, 2002.
Maione et al., "Coexpression of IL-6 and soluble IL-6R causes nodular regenerative hyperplasia and adenomas of the liver," The EMBO Journal, 17(19): 5588-5597, 1998.
Naka et al., "The paradigm of IL-6: from basic science to medicine," Arthritis Research, 4(3): S233-S242, 2002.
Peters et al., "The Function of the Soluble Interleukin 6 (IL-6) Receptor In Vivo: Sensitization of Human Soluble IL-6 Receptor Transgenic Mice Towards IL-6 and Prolongation of the Plasma Half-life of IL-6," J. Exp. Med., 183: 1399-1406, 1996.
Rongvaux et al., "Human thrombopoietin knockin mice efficiently support human hematopoiesis in vivo," PNAS, 108(6):2378-2383, 2011.
Suematsu et al., "Generation of plasmacytomas with the chromosomal translocation t(12;15) in interleukin 6 transgenic mice," Proc. Natl. Acad. Sci. USA, 89: 232-235, 1992.
Suematsu et al., "IgG1 plasmacytosis in interleukin 6 transgenic mice," Proc. Natl. Acad. Sci. USA, 86: 7547-7551, 1989.
Sugita et al., "Functional Murine Interleukin 6 Receptor with the Intracisternal a Particle Gene Product at its Cytoplasmic Domain," J. Exp. Med., 171: 2001-2009, 1990.
Tanabe et al., "Genomic Structure of the Murine IL-6 Gene—High Degree Conservation of Potential Regulatory Sequences between Mouse and Human," The Journal of Immunology, 141: 3875-3881, 1988.
Tsantikos et al., "Autoimmune Disease in Lyn-Deficient Mice is Dependent on an Inflammatory Environment Established by IL-6," The Journal of Immunology, 184: 1348-1360, 2010.
Tsujinaka et al., "Interleukin 6 Receptor Antibody Inhibits Muscle Atrophy and Modulates Proteolytic Systems in Interleukin 6 Transgenic Mice," J. Clin. Invest., 97(1): 244-249, 1996.
Tsujinaka et al., "Muscle Undergoes Atrophy in Associate with Increase of Lysosomal Cathepsin Activity in Interleukin-6 Transgenic Mouse," Biochemical and Biophysical Research Communication, 207(1): 168-174, 1995.
Ueda et al., "Novel genetically-humanized mouse model established to evaluate efficacy of therapeutic agents to human interleukin-6 receptor," Scientific Reports, 3(1196): 1-8, 2013.
Weissenbach et al., "Two interferon mRNAs in human fibroblasts: In vitro translation and *Escherichia coli* cloning studies," Proc. Natl. Acad. Sci. USA 77(12): 7152-7156, 1980.
Willinger et al., "Human IL-3/GM-CSF knock-in mice support human alveolar macrophage development and human immune responses in the lung," PNAS, 108(6):2390-2395, 2011.
Woodroofe et al., "Long-Term Consequences of Interleukin-6 Overexpression in Transgenic Mice," DNA and Cell Biology, 11(8): 587-592, 1992.

(56) References Cited

OTHER PUBLICATIONS

Written Opinion for PCT/US2012/062379 (7 pages), mailed May 3, 2013.
Yamasaki et al., "Cloning and Expression of the Human Interleukin-6 (BSF-2/IFNβ 2) Receptor," Science, 241: 825-828, 1988.
Yasukawa et al., "Structure and expression of human B cell stimulatory factor-2 (BSF-2/IL-6) gene," The EMBO Journal, 6(10): 2939-2945, 1987.
Zilberstein et al., "Structure and expression of cDNA and genes for human interferon-beta-2, a distinct species inducible by growth-stimulatory cytokines," The EMBO Journal, 5(10): 2529-2537, 1986.
Alves et al., "Characterization of the thymic IL-7 niche in vivo," Proceedings of the National Academy of Sciences, 106(5): 1512-1517, 2009.
Fisher et al., "Lymphoprolierative Disorders in an IL-7 Transgenic Mouse Line," Leukemia, 7(02): 566-568, 1993.
International Search Report for PCT/US2013/045788 (6 pages), mailed Jul. 10, 2013.
Kim et al., "Seeing is Believing: Illuminating the Source of In Vivo Interleukin-7," Immune Network, 11(1): 1-7, 2011.
Mazzucchelli et al., "Visualization and Identification of IL-7 Producing Cells in Reporter Mice," PLOS ONE, 4(11): p. e7637, 2009.
O'Connell et al., "Lentiviral Vector Delivery of Human Interleukin-7 (hIL-7) to Human Immune System (HIS) Mice Expands T Lymphocyte Populations," PLOS ONE, 5(8): 1-10, 2010.
Repass et al., "IL7-hCD25 and IL7-Cre BAC transgenic mouse lines: New tools for analysis of IL-7 expressing cells," Genesis, 47(4): 281-287, 2009.
Shalapour et al., "Commensal microflora and interferon-[gamma] promote steady-state interleukin-7 production in vivo," European Journal of Immunology, 40(9): 2391-2399, 2010.
Written Opinion for PCT/US2013/045788 (9 pages), mailed Jul. 10, 2013.
Van Lent, A.U. et al., "IL-7 enhances thymic human T cell development in "human immune system" Rag2–/– IL-2Rgammac–/– mice without affecting peripheral T cell homeostasis" The Journal of Immunology (Dec. 15, 2009) pp. 7645-7655, vol. 183, No. 12.
Anderson, P., "Post-transcriptional control of cytokine production" Nature Immunology (Apr. 2008) pp. 353-359, vol. 9, No. 4.
Carpenter, S. et al., "Post-transcriptional regulation of gene expression in innate immunity" Nature Reviews, Immunology (Jun. 2014) pp. 361-376, vol. 14.
Genebank Report, "*Homo sapiens* interleukin 7 (IL7), transcript variant 1, mRNA" NCBI Reference Sequence: NM_000880.3, dated May 4, 2014, 5 pages.
Genebank Report, "*Mus musculus* interleukin 7 (IL7), mRNA" NCBI Reference Sequence: NM_008371.4, dated May 4, 2014, 5 pages.

\* cited by examiner

SEQUENCE LISTING

```
<160> NUMBER OF SEQ ID NOS: 15

<210> SEQ ID NO 1
<211> LENGTH: 8777
<212> TYPE: DNA
<213> ORGANISM: Mus musculus
<220> FEATURE:
<221> NAME/KEY: MISC
<222> LOCATION: (1)..(8777)
<223> OTHER INFORMATION: Mouse 5' genomic sequence present in humanized
      IL-7 mouse (from NC0000696)

<400> SEQUENCE: 1
ggcagatcct acggaagtta tggcaaagcc agagcgcctg ggtggccggt gatgcatgcg      60 gccctcttg ggatggatgg accaggcgtg gcgtgggtga gaggagtcag ctgcctgaac     120
tgccctgccc agcaccggtt tgcggccacc cggtggatga ccggggtcct gggagtgatt     180
atgggtggtg agagccggct cctgctgcag tcccagtcat catgactaca cccacctccc     240
```

```
gcagaccatg ttccatggta agcgctgctc tctggtgcgc acaagtaggt gcgcctagcg    300
cgccggggac tctgggacag tccgggaggt gccacccgcc cccgcgcctc cgcacgtccg    360
ggaatagccc ggccttgcac tttggacagg ctgagagctt ggcctctccc atggtcagcc    420 actcccgcg ctgagctcgg ttgcccagaa ccattggcac ctgggcgtac aaccctggcg    480
ggcggggagg aacagttccc gaggcggttt tcagatcccc agacccagag cttcagtgcg    540
ggagccgcga cgcggtggcc ccctgcagtc aagactcagt agtcagtggt tttcagccac    600
tttgtcccta gccagtacct cttcaatgca gcccttcctg gcttcctggc tgtgcagtta    660
ctcacaggct gcctgggttc agggcgttgc tgggctctcg cagctcagaa cttcatggag    720
aatgaaagag tcgctcccag gatgcgcttt taaaccctaa aggacagatc attggaaaac    780
cccctcttct ccccgcagta agtctgggag tttccgatcc aggctgtaag ttgacttgtt    840
tgctgggaac ccaagtcctg cggctgagat tgcaaaaggc cagattttat tttccttcta    900
tatatttgct acttaaggga ggcagaactt taagtaccca tgagtacaaa ttcttagctc    960
cctgatcaaa tctaataggc ttgcattagt tttaaataag taaggattta aagtggacaa   1020
gaacagaatt gacagaggct ggaatccatt tgtagctaga actaatagag atgagaacag   1080
aatggagtgt gaggaggtct acctaaggga atgcaggtgt tttaaatact tcctcaagca   1140
agagaaccta tggaggtgca ggatctagcc taaggctctt tccttttgca accccattgc   1200
aaaccattgt attggtttcc ggcccactgt tttaggtaca attacttccc ctctcttagg   1260
tactagcgaa ccaaaaacat ttgagggagt acttatcaga aaccaaataa agatgtgga   1320 gacctgagag actgcccaag aaaatgatgg aaggctgcca aggtgcccct gcaggagctc   1380
actgtacagc tagagacacc gcatcccgt cttctttgca atgccctggg ttctgaaatt   1440
gcctttcact ttaacccttg gattacctac aacctggaga gataaaagga caaggaaaa   1500 gcaaaggtgt aatttaaacg aggaggcttt tcccattgag atacatccat atcggacatg   1560
ccttattttc ttagtaaaga aaatatgaaa atattaaact cacgggagtt aaagtaagtg   1620
gctttttttt tttctttcat tttcggtcca aaatttacta gaggcgtggg taaactccat   1680
caaggctgtg tgctgtgttt ccactttgtt atgtcgggac accaagtaaa caaggattca   1740
ctcgctgacg ctcaattgtg ctgcctcatt atgaatcagc atacatttta tttgtatact   1800
aataaaagga aacaatgaga aacatagagc cttgggaata tggaggaagc ctgaagatct   1860
atctgtaaag gagaattaga aatttcatct cagtgtgtat acttcttgaa caaaaatgga   1920
aagttctttt ataaaaccaa tctcatggcc catgggtatg aagtactgtt atcctgactc   1980
ttgacagata attttgtttt ttaattaatt tatttttatt ccttaatctt ttttttttaca   2040 gtacagactt tatacctctc ctgttctgcc ccccccact gctctcctcc ccatacctcc   2100
tccccagccc ccaccccacc cctgactcca agagaatgcc ctcatccccc atgccactag   2160
gcctccccac tccctgggc ttcaagtttc tcaacagtta ggtgcctctt ctctcactga   2220
ggccagacca ggcagtcctc tgctctatat gtgttgggga cagacaactt tataatatgt   2280
agaaatattt acttttttccc ttgaaatagg agcatacgct gtagtttcag agcttggcca   2340
agaagcccct tcatgtagaa gacaatgaat atttgtactt cctctcacta tctgtgcatg   2400
cagttatgtt gtaggaagtg taattcagta gctaatagcg gattccctag acacctcaac   2460
ccgaacatca aatgcagctc ctgaatccct agaaaaattg ttttggagaa ttgttctttg   2520
ggctccagat tctctactgt aaactgctag tgacctgtat atatatatat atatatatat   2580
```

```
atatgtatca tgaaatggct ataaaattga attatttgtt gaaatagact tgggaaagga    2640
cattgaaaga acacttctca aggaggatgg gaaagtcctc aaggtctcaa ccctagacaa    2700
actgttcagg ccacgaagaa atgctgactg acagtggaga aatagacatc cccagagagg    2760
agcatacaaa ttgtttatcc aaacagccag ccctgaagac atatgtgcaa gtaaggttat    2820
acagactggg caggttgact ttatgtattt agggagatag atggatgata gctagctagc    2880
tagctagagc acaacactta atgaaataaa aggtcatgaa tttgaaatag agcaagaaag    2940
gatatatatg agagtttagg ggaagaaatt gattgaggaa ataaaataat gatgttgtaa    3000
tctcaaaaac taaagaaac tgatagatga caggatatga tggactgagg aatccaattt     3060
tattatgtcc actttgacct cataacttaa gcagttgaag attgtatgta ttatttggct    3120
tacatttaaa accaacaaga attttagac agctatcatt ctggtttaac caaattcccc     3180
actgaaaaca aattctccag tttcaaaccc tgtaagcgat ttaaagacaa tactacaagc    3240
caacacttgt cttgtaatgc ttctacagtt tgttttatct gtgacctaat gaaaagttca    3300
gtggaggctg aggagtgagc tataaatcaa agtaacaaa atatggtaag tgctgaattc     3360
ggatgccatt gggacaaaag tgttaaataa acttctcaaac cagaaaata ttaacttgtt    3420
acggtgcttg tatgtggaag aaataactgt aaccacagaa caaggtcac actcctgatg     3480
gtggagccag aaacccatgg gatcatacat tatcatacat atcatacatt agagagcctg    3540
gaaggttttc attttagaaa tcagggccag gaagctgaaa tgaaactcag ctatttagtc    3600
agttacacaa aatcctaaat tctctatgct ctaaatctcc ttgtttataa tatatatact    3660
atttatatgt attataaaat attaagtata tattataata tattaaaata tgtatggtac    3720
tgctctggtc tgtcagcagc tactttactt gattgaaata gtctacaaat gaagggctgt    3780
attgtaaaaa tagtatagaa ttgaaaattt cacgtaacac acacatgtat tatcaaagca    3840
agtgtgaagc aatgaaaaag tgctgcccgg tgaggtgtaa ggtcacatca ttctgggaag    3900
cacatatctc agaagaaaac tggcaatctt ggaaagtatg gcaaatgaac ttattgaaac    3960
aggaaatgga ctttgaaatg acttttagat ataggtgcga attaatctct tttcactaac    4020
catcataact ttctccttg agttcaagtc acattccctg tctctttcat ttgcctggtc     4080
cccccaaaaa cataattttt agggacctat aaggcaaaag atgaaataaa aagccagttt    4140
ctacaaaaaa tgtagatggc tataatccaa ttgagtagta attgatacct gtgtatccca    4200
gtgaagggca gtcataggag aaggctgatg aatggtatta tgagaaggtg cctttcaaac    4260
agaatagcag cagataagat gttatcaatt gattatgggt atttaaaagt gattgtcatt    4320
ttctccccct cttgaagcag atatagatca gattaggcca gattaaaagt agataaaggc    4380
agttttgtta ggaatcccct ctctggtggg ttcatccatc tcacaggtgg aagtcagtga    4440
agtcacacag ccaggctaaa gcatgggggt tttatagagc ttaagcaggg agtagtgatg    4500
tgccagaagg agctaggatg gtgtccatac gtggtcaaaa actgagcccc tggtgggcac    4560
tctgggtgt gttgcaggaa cccagggatg agacatggcg acttattggc ctagagtttt     4620
ttgttttgt ttttgttttt cccaagcagg ggttccgggt gcaggcaggg ttggggaaag     4680
gagggtagct tccaagtggg gtttccctgc ttgttcagaa tatgagcagg agttccagcc    4740
taacaccccg acctcttggg gtatagatac agccacactc tgctgaagag ggacgggaga    4800
gttgggagcg ggtgggatca tactcatctg caggcatgct gtaggaccat tcggtggtgt    4860
gttacttaga aactttatg aatccgttcc tggatgaaga gaaggtagca aggtgctagg     4920
aagatgtgca tgtgcaaggt gctaggaaga ctgaggctag ccatgtgaag agtaacactg    4980
```

```
ctagagagaa ttgaatgtgt cttggttgtg ttgtgggaac tctttagaca atttgcggag    5040
tgactctgtc caggtctcca caaggccaga ctcactgatg taagagtggc agggacatgc    5100
agatgccgcc cttaccagtc atgaggatac ttttagggcc attgaagcct ataagaatct    5160
tattaagttt acagagagag agagagagag agagagagag acagacagac agacagacag    5220
acagacacag agacagacag agacagacag acagagagat tttagacatg ttagacagta    5280
gacttatacc tttttgtcat agtacaggct tcggaaacat taaaatttga ttattattaa agctttgaat    5340
tttgaattct taatataaca gaaacatagc taggggaaga atctgaagca tttttttaaa    5400
aaaatatatt ttatgtcatt ttttctcttt tgtcttttaa cctttataac ttgcatttat    5460
taactttaaa catcttttat actatgaaag aactttctta catcctttga atttaaactt    5520
ttatatactc agaccaccta tgggtttttc tctcttttta tccagatatt gaccatgact    5580
cgtaggtagc tgatcattga gagcagttat tgcaaagtga gttcctttag ataaaggaat    5640
attgaaaatt ttatattgaa tttttcagtc taataatgag ataaattgta tctagccaaa    5700
gtagtggcat gtcttggaga gtgtcgtttg aggactgatt tttacacatg aagaggactg    5760
ggaaggtagc tgaagtcttg gatcctgatg ttaaatgaat cctcaaaccc accagagtcc    5820
tgagaaggat caatttttatc tgagtaagga gggaactgca agagcaagca gtttctgagt    5880
ctattaaaaa tgacacagac ttacaggact ccctggacag tcagtcatcc aggaattctc    5940
tgtggtcagt ggggcatcca ttttggctat caggccaaga aaatctggca gactttgtgt    6000
gtgtgtgtga atcaagacta tgagaaaaag actgccctac cttgtctagg caagtgaatc    6060
agtcaacttc ccagtgtcct acctgtccac agtgtggccc atgtgctgtc aacagtcgca    6120
gcaaagggct ctttatagcg agcaagcttc aggcagaagt tcttctgggc tgtgttcttt    6180
ggaggagatc agggtgctg tcaagagctg gtgtgtctct gttatgaaaa gctttttcat    6240
tagccatttt aaatgccata ttttatagac ctctgaagcg tctgaggacc atttgtgtct    6300
ctacagtata tctaaataga caaacgtttg ttttttggct attcaattttt tatttaactt    6360 tgaaaatata gataggaggc taagtaaaac ttattttggt aattaatcat aattataagt    6420
gtagttatga acatattaaa gaatgtgatt atttttgagg taactgataa ctaacttgta    6480
tgttttaata atgtttaaca gcttataata aatgctgtat gttatattta acctgaaggc    6540
agtgttagga cagaaaaggc ttaataagtt ggaaaaatgt ctcagtagcc cttcatgggc    6600
ctaaggaaaa agagtcgctg tggcccaggc ataggtttaa ggaagctgta gttactggag    6660
gaaatggagt gaccattaag ttaaggggtg tgggagaggc tgatgtgctc agtgtatgag    6720
caatgaggtc tcctcacagg acaggctgga ctgtgcagag tggatagggt ggacatggga    6780
gtgagtgtag ccttgcccca ttggcgagga gaaaagccag gttaccagga ggaagaggag    6840
gaggaggggg ggggaagtg ggggaggag gagggctgct gaagctttaa cagagtgcag    6900
gcgaactgaa aggaaggaat cctgcggggt tacaagaacc agagccatgt ggaacacata    6960
gcaggctaaa gaatcggact tcagaattta gaatcaaatt tccagacaag taagtgatcc    7020
atacacactt tgggaggatt agcatggttt ggagcaacca ttgcagttac aaaaggttga    7080
gtgtgtcaaa gagaagaagt gggaagagtc tgggctctgt caatacaggg gtttggggtt    7140
tgggatccag gtccttggag gcaagggtc ttttggagtg aacatccttg ctagtaggac    7200
gtgagcctta gaacattggc tacagaggaa gggacagggt gtggttccca acaaacctgg    7260
ccagaaggga ttcaggccat tgcccgcat accaaaagaa atgttaagct taagatccgt    7320
```

```
ggagaatttt aacatcaaga atgctctctt gtggccgttt actgaagcga ggccatagaa    7380
caaagtctga acagtccta atttggacaa cttttgtagc agtcacccca ggaatgtctg     7440
aggatcaggt ttagactccg tgttgcccat ctcctagact tgtggcgacc tatgatacag    7500
tgtcccactt ggtagcctgg ggtaaaacag tgaggagtaa agaaaccttg taaaggatat    7560
ctcagaatcc aaatactagg ccatggcttg gcagaggatc ttggtaagtt caaagttgat    7620
ccttcagatg aagagagaaa gggagagaaa ggagcagacc ccatgcagcc atggtccctg    7680
cccgctgggc tgcaggctca acttctcccg cattttgaac caagatgata ggaattttct    7740
ctccatccat gaagcagatc tagggcagat ttgatgagat aaaaagtaga tacaggcagg    7800
tttattagaa gacaactctc aagtgggttc accgatctta cacatggaag tcagtcaagt    7860
cctatatctg ggctaaaaag caagggaggt tttatagagt ttaggtgagg aatgatgcca    7920
tgccagctag gaactgggat ggtgtgcata catggtcaaa aatgagaaa aaaggagtga     7980
tagctctttc ctgtgcttag cacgatttag ttgcctgtag ttcttttgtc tatagttgta    8040
gctctgtgag attctgtaat ttcgaccaag catactttct ttacatatat atatatatac    8100
actcagctgc taatttatgg tggatttata aataaattta tttataaatt tataatttat    8160
tgcctttta ataccatgta taatagtatg atatattgca tcctatgata tccttacatt     8220
ctttaagttg tttccaatgt caattccttg ggtttagaga aatattgttt agacttttaa    8280
atagagaaga tgcacataaa atgctgaaca ctgggatttt ataacgttaa tttgggaaaa    8340
tcatggtaag tatattttca acataactga gttcagggaa aaatgaaagc aagattcatg    8400
aagatatagg tggcttaacg tttttatgta ccagaagttt ccatcttaat tatttactcc    8460
aagtgatgat tccatttaaa atctccttcc ttttaattaa acagttcact ctgattggca    8520
tgacttactt gatgtagtca taaacaccag ctgagaggtc tcgagtctat tgtgtgaact    8580
ttgcctaaca gggaaggaat ttaaagagag ctatgcttga acagaatcta ggtctttggg    8640
aaaatagata cacaaaataa tgacataagg gaaagagttt gcgaacatga tttagggggc    8700
aaagtaaaac tctgtaaagt ccatcacaaa gaatcgccat agtgcaagca ccaaaaaggt    8760
gaccacactt cacattg                                                   8777
```

<210> SEQ ID NO 2
<211> LENGTH: 944
<212> TYPE: DNA
<213> ORGANISM: Mus musculus
<220> FEATURE:
<221> NAME/KEY: misc_feature
<222> LOCATION: (1)..(944)
<223> OTHER INFORMATION: Mouse IL-7 downstream (3') genomic sequence from the humanized IL_7 mouse (from NC00000696)

<400> SEQUENCE: 2

```
ccaattgcgt actttggata gtgtctcttt ttaacctaaa tgacctttat taacactgtc     60
aggttccctt actctcgaga gtgttcattg ctgcactgtc atttgatccc agttttattg    120
aacacatatc ctttaacaca ctcacgtcca gatttagcag gagactagga ccctataact    180
ttgttaagag agaaaacact aatttcttgt tttatagtag ggtcttattc gtatctaagg    240
caggctagga ttgcagacat gagccaatat gcttaattag aaacattctt tttatgttaa    300
actcatgtct tttacaagat gcctacatat atcctatgta tatgcctgtt taaatccttt    360
tttgtaaggt ctgctgtctt ccttcagttg taatggaaag aaacactatg ttgtagaggc    420
caaatttctg aaagtgataa gggtttgctt gtactgaatt ctcattctcc ttgcttttc     480
```

| | |
|---|---|
| cagccacgtg agcatctagc tatctatacg ctggatgtat ttgaccgatg cctgctccac | 540 |
| tggcacattg catgtgtggt agccatgcct tcttgcttct ccttttcccc aaccoctata | 600 |
| atgctctact cagtggtaca gatagctggg attatcacaa ttttgagaga aacaccaatt | 660 |
| gtttaaagtt tgtttcataa tcaccatttg cccagaaaac agttctctca acttgtttgc | 720 |
| aacatgtaat aatttaagaa actcaattt gttaatggac tttcgataac ttccttagat | 780 |
| atcccacatc tcctacgtgt cagtcctttg tcctgaggaa ctggtaaaat gggtaagccc | 840 |
| ttagctagcg aactgaaggc attcgcatgt gtaagataat ctctatacct gcaaggctgt | 900 |
| ctggatggct ccctaccaat attgaacaat attctgattt tggc | 944 |

<210> SEQ ID NO 3
<211> LENGTH: 72752
<212> TYPE: DNA
<213> ORGANISM: Homo sapiens
<220> FEATURE:
<221> NAME/KEY: misc_feature
<222> LOCATION: (1)..(72752)
<223> OTHER INFORMATION: The human genomic IL-7 sequence (NC#166E2F2)

<400> SEQUENCE: 3

| | |
|---|---|
| acatccgcgg caacgcctcc ttggtgtcgt ccgcttccaa taacccagct tgcgtcctgc | 60 |
| acacttgtgg cttccgtgca cacattaaca actcatggtt ctagctccca gtcgccaagc | 120 |
| gttgccaagg cgttgagaga tcatctggga agtcttttac ccagaattgc tttgattcag | 180 |
| gccagctggt ttttcctgcg gtgattcgga aattcgcgaa ttcctctggt cctcatccag | 240 |
| gtgcgcggga agcaggtgcc caggagagag gggataatga agattccatg ctgatgatcc | 300 |
| caaagattga acctgcagac caagcgcaaa gtagaaactg aaagtacact gctggcggat | 360 |
| cctacgaag ttatggaaaa ggcaaagcgc agagccacgc cgtagtgtgt gccgcccccc | 420 |
| ttgggatgga tgaaactgca gtcgcggcgt gggtaagagg aaccagctgc agagatcacc | 480 |
| ctgcccaaca cagactcggc aactccgcgg aagaccaggg tcctgggagt gactatgggc | 540 |
| ggtgagagct tgctcctgct ccagttgcgg tcatcatgac tacgcccgcc tcccgcagac | 600 |
| catgttccat ggtaagcgct cttctccctt gcgcacaagt tcgcgcgccc gacgcgccgg | 660 |
| ggcaatccca gacgcgctgg gggcccctgc tcctaggcaa gtccgggaat agcccggcct | 720 |
| tgcactttgg acctgcggag agcactggct ctcccatggg cagccaacag ccgcgcctga | 780 |
| gtatcctggc acatagccac ttgaacctgg ggcggctgct gcccctggca ggctgcgagt | 840 |
| aacagtcccc aacgcctgct ttctgtcctg agagggaacg ctgcagcctc cgcgccgctc | 900 |
| agcggtggca gcccacagcc ggtctcagaa gcagccaaag gctctctgtc tggcgccctt | 960 |
| cccgtgctcc tggccgcccc aagttactca cgcaggcggc ccgggttcgg cgagtagctg | 1020 |
| ggctcttgca gctcagaact ccctagagaa gtgaaagcga agctcccacg ggacgcgctt | 1080 |
| ttaaaccota ggggaacagg tctccggaaa accccattt tccccctga gtaagactgg | 1140 |
| gagtttccgg caagggctgt accttgcgcc tattgctggg aaaccagtcc tggggctggc | 1200 |
| gctgaggaag gccagcttct gggttttttt gttttgttt ttgtttttgt tgttatttt | 1260 |
| tcctacgggc gcttcttgat ggaggcagaa tgaaataggc gtgactctaa cttccagacc | 1320 |
| agtattgaga cctaatatat cttatttgtg cagaatacgg atttagaatg gacagggaca | 1380 |
| gaattcagga ggggttggatt cggatggcag tcatatatga ccaatgaaag agccaaaaaa | 1440 |
| cttactggaa ttaaaaaaga ggaaaaagga ttgtgagggg aaaagatctg cttaggaaaa | 1500 |
| ttggaatgct ttacagtaag tacttcctca agcaagaaga cagctggggg gagggtgcgg | 1560 |

-continued

```
gaataggaaa ctgactgctc tttcttttga tggctactcc gttagatcaa gacttctttc    1620
cactctcgtg ggtaaagaat caagaattga cacaaccaag gagtgccagc tcagtaacaa    1680
aacaaagata gagagagcgg aaagaatagc caacgtaatt atggaggact tctaaggaat    1740
gtcctcccgg agcttaatac aaaactaaaa attgagcaca accctatttt ccttgcaatg    1800
cccatagttc tgcagtttct tcttctggat cacccttggt tctaatcctt gcaacacctc    1860
tgctctaaag tagaaaggta aactgagaaa aggaagctag cgtgtgcatt tttcagaaaa    1920
agcctttact tcctgaagca cagttatatg aatcatgggc tataagtttt cattagcaga    1980
caaaatatta aaattctaat aataatgatt ataatgcatg gcttcctgaa gtttgtttca    2040
agaaatttca ctagaagctt gttccattaa gagtgcacat aatgttactc tttacccttt    2100
gtctttgcca tttcttttga gagttgaagt agttgaggat ctactatgtg gtctccaact    2160
gtcttatctg gtttgggtaa tttcatcata tttgaggacc aaaaagttga atagcaataa    2220
aaatagactc tactcgggag gctgaggcag gaggattgct tgagcctgga agtcaaggct    2280
gccgtgagcc atgatcttac cactgtcctc cagcctaggc aacagagtga tgccctgtct    2340
caaaaaataa taatagagaa ctaatattag aaaccctgaa caagcataaa ggagaattac    2400
aaactgcatc acgttagtgt ttgaatattt ttttaaaaaa tggaaaaggc catttcatag    2460
aacgaactta cgtgtcatat tcacactcat ctatgtgact ttttttttctg cttttaaccc    2520 tgacacataa cctactgtaa caagaacaaa tatttagtct ctttttctga aataaaagca    2580
tatgatgcag tttcacagtt tggccaggaa gtaccttagt gaggttcatg cacaggaaga    2640
tgggttttta tgcaatcccc ttgactacac atatatggtt atttttttaag gaagcaatgt    2700 agttcagtgc ctaaaagctg aggttctaga ctcttcaatg tgacagtctt ggatttgaat    2760
tccatatcta tattatgtac aggaattttc tgactaggca tggtggctca agcctgtaat    2820
cccaacactt ggggaggctg aggtgggcag atcaccttag gtcaggagtt cgagaccagg    2880
ctggccaaca tggtgaaacc tcgtctcaac taaaaataca aaaaatttg ccaggcgttg    2940 tggtgggcac ctataatccc agctactcag gaggctgagg gaggagaatc acttgaacct    3000
gggaggctga ggttgcagtg agccgtgatc gcaccattgc actccagcct agatgataga    3060
atgagactcc atatcaaaaa aaaaaaaaag agagagaaaa atacgaaagg aattttccta    3120
catgactgtc tttgtgcccc agattctcca tctataaatg tgaataactt gtagtactta    3180
cctacttctt catgaagtgg ttatggaatt aaattatcag tgaaaatagg tctatgcaat    3240
ggacattcag taaacactgg ttttaaagac tgataaagac tggagttgat ggattgtaga    3300
aaactattta tgttaacttt gaccccata acttaagcag ctgaggattg aatgtattat    3360
ttggcttaca ttaaaaacca acaagaattt ttagacagac ctccttctgg tttaaccaaa    3420
ttccctactg aaaacaaatt ctccaatttc agcctcttca ggggaagtaa gggcaatccc    3480
acaagccacg cttgccttgc gttattccta tggtttatct tttcggtaac ctaatgaaaa    3540
gttcaggatg gtgggagtg tgggtgtgac aacaatgcca aaagcactct caaaccagcc    3600
attcttaata tgttactctc tatgtgatgt aggagaaagg tcttcaatta tggaccaaac    3660
taccaagcta catcattaat gggagagctg ggaacctatg agatgtgggt ccaaggccct    3720
aggtatgttt gcagcattgt ccgtgaggca atttcagatc taaagagttt ctgcatttgg    3780
aggaccaggt agattcttag aataaggtgt ctgcaagatg aaaagatca tttagtctga    3840 agttttcatt ttagaaatca ggtaagtgac cttaagagat gctgtgtcat ttacacagtc    3900
```

```
acacaaacca ttgtcttggc aagtcaaaag tctcaagttt tgacttgact actcagccta    3960
ggctcagtag atcgtggctc acggccatgg cttacggcca tggctcacgg taagatcatg    4020
gctcatggca gccttgactt ccaggctcaa acaatcctcc tgcctcagcc tcccaagtag    4080
agtctgtttt tattgctatt caacttttg gtcctcaaat atgatgaaat acccaaacc     4140
agataagaca gttggagacc acatagtaga tcctcaacta cttcaactct caaagaaat    4200
ggcatagaca aagggtaaag agtaacatta tgtgcactct taatggaaca gcttctagt    4260
gaaatctctt gaaacaaact gcaggaagcc atgcattata attattatta tgagaatttt   4320
aattccaaaa cctctgtgct ttatattgcc atagtctgtc tggggctaat tattcaatga    4380
caacaatggc aacagaaaac actcttaaca ggcaaggcaa attatgtttt aaaattgaga    4440
aagtacgtgt aatatacaaa aagactgaat tttccagcaa ccctcattgg aaagaatgca    4500
caaaatgcca tccggtgaat aaataggttg atttaaattt gaggagcact taactactga    4560
aaattgaggt gaagaagaca gctaatgctc atagcaagta aaacaacctc atgtattaaa    4620
acaaaggtg gacctttgga atatttatga taatggtaaa agtatccctt tcactctagc    4680
atttaattat tttattatat tctccttaa gctcatttca gttatatgt tatataattt      4740
ttcctctatc atctactcct cccgaagtat acctttgga cccctgtaag atgacagaga    4800
aaataaaaag tatgatttca tacaatctat acaaatctga ttacaaggtc agaatctggt    4860
gaataattag caattgatca tccaaatgtc catcagcaga ggtttggata agaaaatgt     4920
ggtatggccg ggcttgtaat tacagcttgt aattctgaca cttaaggagg ctgaggcagg    4980
aagattgctt gagcccagga gttcaagacc agtctgtaca aaagagtaag agccgtctgc    5040
taaaaacaaa ttttaaaaaa ttagctgggc atggtgggc accctgtagt cctagctact     5100
cagaacgctg aggtaggagg atcgcttgaa cctaggaatt tgaggcttca gtgagctatg    5160
atcatgccac tgcactccag cctgggcagc agagtgaaac cctgtctcaa aaagagaggg    5220
agaaaaaaag aaaatgtggt atatgtatac catggaatac tactcagcca taagagttaa    5280
gtcgtctttt gcagcaaaat ggatgaaact tgaggccatt atctaagtga aatgactcag    5340
aaagtcaaat gctgcatgtt tttacttata actgggagct aaacagtggt acagatggac    5400
atacagggtg gaataatagg cattggagac tttgaaaggt gggagagtag gaggggata     5460
aggattgaaa aattacctat tgggtaccat gttcactatt caggtgatag atacactaaa    5520
gcccagactt caccactgta cagtatatta aatatgtatt agtaagaaat ctgctctggt    5580
ccccttaaa tctatgagtg tacattttt taattgccaa atatttttt ttaaattagc       5640
aattgatcac tgaggatctt taggttgaag gaacaggagt agaagagaga ggcaaaactt    5700
cattcagaag acaaatgtga ttacatgtta tcaatagatt atggccattt ctaatcgaat    5760
cctggtaaag caacaaattc aggttagcat ccaaacctgg cacctactat gtatgtgtta    5820
cagaaagact aacttgcaga acttttttgga tatttataaa tcatatatat atatatgaga    5880
ttttatatat aaagttcctg acacatggta ggtactcaac taaaggtaac tagcatcatc    5940
atcattatct gtctcctaag ttaattcatg ctcatcatgc atataggcac ttagtggcag    6000
agttattaat atatttgtat aaataaaatt atcaattttt gtttctctta ctatgttgtc    6060
acatatgcag atgagaagtt agatttatgt ttgttttcat aattgctacc cagaaaattt    6120
tctctatttg taacaacatg ggtcacttga tttattggga ggtgttattg attgttttat    6180
atgacagatc atgatataat agatgacaat gttactggaa actttatgat atccctaaca    6240
gtcttcaggc tgtcacaata ttagttcctt gggtttgaag gagtgttgct tgtactctta    6300
```

```
atcagagaag gcacacaagt gaaatatctt gcattcaagt acaattgaag ttcatttggg   6360
aaattcacag gaaatacatt gtcaacatgc ctcagagttt acaaaaagat acaaataaga   6420
cactatggca ggtttatgaa gaaataggtc cctgtatgat cagattttaa tgtttgtggg   6480
aaccactggc tttccatctt tctgcctgaa ataataccat tatttcagtc cttttgatta   6540
gacaattgct cctaattggg aagagttatc aaaaacagat agaaatcatt ggtttctatc   6600
tgaggatgtg aatttattta cagagttttt ctaaacatgac aagaagctgg atagcgctgt   6660
gtttgaaaag aatctgggtc tctggggact cagagacaga agatagtgaa aggataggag   6720
agtagtccca aaatacaaac ataaactttg taagactttt gggaatgtaa acccttcagg   6780
gttcattatt aaaagaaag agtgcactta cagtagttac agtgcaatcc cagggagatt   6840
aacctcccac agtgttgcct ccaagaagca aatagacatg gactaccatc aaggtttaca   6900
aaaatataca attacgtgca gtacatcata aaattccaac aatatgtaac tcttcgaact   6960
gtagtgcacc tctttacctg tatatgcctt ttcttatggg gatgttcaac ataaattcaa   7020
attgattaac ccctggagt gttttcaga agcagtctat gatttcatca cccttgtttt   7080
gcactttcct aaagagtaat tgcaaaataa aaagtgaaa ggacgctata ctccaaaatg   7140
ctgttccact ttggttgtta cataagttca acttttgagg ttcttcctgt agtatctcca   7200
aaccaagatg tattttaaa attattagaa attagtggtc cagtccattg aaaccccaca   7260
atcaaatgca atacgatata acatttagct cattcttatt tactgtcaaa tttagtttct   7320
tttaggtata tctttggact tcctcccctg atccttgttc tgttgccagt agcatcatct   7380
gattgtgata ttgaaggtaa agatggcaaa caatatgaga gtgttctaat ggtcagcatc   7440
gatcaattat tggtatgtga ttattttgtt ttactcacat tttcatgcat tgggaaaatt   7500 tgaaccttt tggtatgcag ttttataatc aagtattcat ctttcttgac aagaaagtga   7560
agtaactata gaataaaatt taatgagcta ctaactgtat attttatag ctgacataat   7620 tatgtagctt aaaaataatt ctttcctcga ctctaagatt ctcacaacta ttcatttcag   7680 tcctattcc cttttagtaa atttcttgta agcataattc agtatcactg cctaaatttc   7740
ctcacctccc atttaccatg ttagtccctg tagaagcatt acattaagag tgggaaaata   7800
acagagtaaa tagttaagac ttatggtgaa tagatgtgta ttttatttgg ctgtgtgtag   7860
atgcatagtt atttatatgt gtgtatttta tatctatgtg taatcaataa tttgttatga   7920
gttaaatttt ctattttga tggttaaagc ttttctaatt aatagatttt atacctaga    7980 gccaacttag gttctagaa aattcgagca gaaagtagaa aattcccata tgctctctct   8040
ctctctgcac tgtttccctt attatcttac atcagtatgg cacatttatt acaattgatg   8100
agccagcatt gatacattac ataagtgcat agttaacatt aggattcatt ctttatgttt   8160 tatagttttta tgggttttga taaatgtata ccatcacata tccgtgatta catatcatac   8220
aaatcatatg gtaaaaatct cctatccacc gactcatcct tctctttctt cccctgaact   8280
cctagtaacc actgatttgt ttatgtctct gtagtttgc cttcttaga atgtcatata    8340 gttagaatca tgcggtctgt atgtggcctc tttagactgg attctttcac ttagcaatgt   8400
gaatcaaagc atcccccatg atttttttgtg gtttgatatt tcatttttc ttattgctgg   8460 ataacagtct attgaatgga tataccacaa cttgtttatt ttttcactga ttgaaaaatg   8520
tgtcacagtt gcttccaata tttggaaatt atgaataaaa cttctataaa catatacgtg   8580
cagggttttg tgtggacata agttttcaac tcaggtaaat acctacaagc atgactgctg   8640
```

-continued

```
gatcatatgg taagactgtg tttagctctg tacaaaactg ccaaactttc ttccaaagtg      8700
gctgtaatat tttgcattct taccagcaat gaatgagatc ctaatgcctt ccatcttcgc      8760
cagcctttgg tattatcagt tttgcagatt ttaaccattt taataggctt gtcatagtat      8820
ctcagtgttg tttcaatttt ccattccata atgacataca atgttgacca tcttttcaga      8880
tactttttgc catttgtata tctgctttgc tgaggtgtct gaactcacat ttttactgaa      8940
atcttaacaa tattgagtct tcttagccat tatcatgcac tatctctttt ttaattttt      9000 tcatcattta attgtattat ctggacagag aacaaatgag tattactgtg acaacatttg      9060
taaataatta tatgtgtgta aaactctgca aagaagatg caattgaaaa tgcaaacttt      9120
catcagagct ttgttctttt cagcatataa atcctgtaaa tattttatta gacttatacc      9180
taaatatttc atattttagt gctattttaa atggtgtgtt tctaatttca aattttagtt      9240
gtttattgct ggtacatagg aaagcaattg attttttgtat attaacctat gtcctgcaac      9300
cttactataa tcacttgttt gttctagaag tctgttgttg attattagga attttctaca      9360
tagacaatca tgtcatctgc aagagttaat tttttccaag gtttcagagc tgtatcaata      9420
caatgtgatt gatttattgt tttaacagat aattagtctc ttttcaatca gattgaaact      9480
gaatagcaaa ggaaaactct ctcaaatgtt cataagatgg gagaaattgt ctaatctgtc      9540
ccccgacttt tactccactg tctcttccac atactcatac tgaagtggca tgatgccttg      9600
aggaatttag tgttatacct cttgtaggaa tatggaaact aaaaagagat actgtgctac      9660
actgtacatt gtaatccaga ggttcctgat tttgcccatt gacaagaaaa aaaatagtgc      9720
acagtaaatg gcaattgctc catttagatt tcttgctaat ttggacattg catttgatga      9780
tgctactaaa ttaatctttt gagtcaagat aatatttctc atttaatttt gttatctggg      9840
cagagaacaa actagtgcta gttcaacatt tataaataac tatatgtgta taaaagtgca      9900
aaataatatg ctattaaaaa ttcagtaaaa ggagagtttc atccaacaga ctcatgacac      9960
atttttttgg tgggagaata tagaggagct tatctcatta acacacaaaa caagaacaag     10020
tacatcagca gcaataatta tattattttc aaaaaacaaa acatggctac tcttcttaag     10080
gaggttaatt cacaagacat ggaagagaac acagctaatc agtccaactg agtagttcca     10140
tagtaacctt aagaatgttt tctatacata gaaggtgata aatttgaggg aaggagaaag     10200
aaagtctcaa tgaattatta atgtcaacat gactggtaga gcagatttag ttactcattc     10260
attcagtgtg gactagatgc tttgcagaca ttactgtgtt taagtcttgg ggagaccata     10320
atactaatag ttatgaagtg cttgttatgt tctcagtgct ttccatgtgt taactaattt     10380
aatccttaca acagcccttg agaaagacac tcttactacc tccgtttcac aacagaagaa     10440
tctgaggccc agggttatcc agtttataag tgaccgagcc agaatctttg tccatgctct     10500
ctaccccact ctcctacctc ccaaggacaa tctctgtgat agtttattca atcagcaaac     10560
atttatttag ggcctgatat gtacaagtta ctatgaaaaa cccatttgtg taggtgatgt     10620
tgggtttggg tgtggataga atgatggacc aagtacagat cttttttcaa gaagcttaca     10680
ttttggtgag tgttaaagat tggtggtgaa taatgcaagt tacagtttta aaagtaggaa     10740
gagtgacttc ctgtttgtta gatgtctgct tatcatctaa caaatagact ggttgtaaaa     10800
caagctcaga aacaaaaaga tgtaaatggt gttctggaag tagtaaagaa gcaattttgg     10860
cctgtgtaga agtttcagca agttatccag aaggtctagc taagatgatt ggtaaaagtg     10920
gctacactaa acaacagatt tcaatgtaga tgaaacatcc ttctactgga aacaggcgac     10980
atctagaact ttcatagcta aagaagagaa gtcaatgcct ggcttcaaag cttaagagga     11040
```

```
caaactaact ctcttgttag ggacaaatgc agctggtgac tttaagtttt agcaaaatat    11100
tactgctcat tgacaatgca aaactagtca cccaagagtg ctgatggata ttaatgtttt    11160
cataactgct aatataacat ctgttttca gcccgtgaat caaagagtag tttcaacctt     11220
caagccttat tttttaagcc atgtatttt gaggctatgg ctgccagaga taatgattca     11280
tctaatagat ctgggcaaag aattgaaacc ttgtgaacag cattcattgt tctgtagtag    11340
atgtccttaa aaacatttgt gattcatggg aggaggtcaa aatatccaca ttaacaggag    11400
ttcggaagaa gttgattcca actgtcatag atgactttga ggggttcaag acttcaatag    11460
agaaagtaaa tgcagatatg gtagaaatag caagagaatt agaattagaa gtggagcctg    11520
aagatgtgac tgaaatgctg aaatctcagg ataaaactgg aatggatgat gagttgcttc    11580
tcaggcatga gcaaagaaag tggtttcttg aaatgatttt actttgagta aagatgctgt    11640
gaacattgct gaaatgacaa gaaaaaattt aggatattac acaaaattag ttgttaaagc    11700
aatggaagga tttgagagga ttgcctctaa ttttaaaaga agttctactg tggataaaat    11760
gctttcaaac agtatcacat gctacagagg aatctttat gaaagaaaga gttaatctat      11820
gtggcaaact tcattgttgc ctcatttaa aaattactac agccacccaa ccttcagcaa     11880
ccaccactct gatcagtcag catccactaa cgttgaagca aggccctcca ccagcaaaaa    11940
agtttacaac accctgaagg ctcagatgat tgttagcatt tttcagcaaa aaattctttt    12000
taaattaaaa tgtatacatt gttatttag acataagact attgtacaca taatagacta     12060
cagtatagtg taaacataac ttttatatgc tgggaaacca aacaaaattg tatgactcac    12120
tgtattgtga tacttgcttt actgcagtgg aaccaaaccc acagtatctc tgaggtatgc    12180
ctgcaataaa ttatgcaatc attatcacta tctaattcta gaatatttc atcattgcca      12240
aaagaaatat tctacccatt agcagtaact ctttattccc catcactagc ctctggcagc    12300
cactattctg cattctgctt tctgtctcta ggaatttgcc tattctggac atttcacatc    12360
tgtcttgtat ataattcata tggatgatat gcagctttt gtattgatct tgtttgcctt      12420
agtataatgt ttttaaaatt aatccatatg ataacaggag ttagtatttc atttctcttc    12480
atggctcaat aaaattctgt tgtatggata tgccacattt tgtttatcca ttcatcaatt    12540
tctggacatt tgggttttcc attgtttggc tatgcaagtt tttatacaat tgtcttgata    12600
tgttcctagt agtcaaattg ttggattata tggtcactct gttaaacttt ttgagaaact    12660
gcaaactgtt tctaaagagg ctgcaccatt tgcgtttcta tcagcagtta aggctctgat    12720
ttttctactt tctcaccaaa gcttgttatc atctaacttt ttattctagc tatctctgtg    12780
ggtgtgaagt agtatctcat agtgatactg attggcattt ccttgatgac taatgatgtc    12840
aagcatcttt tcattattgg ctgttattat cagccatttt atatatcttc ttttggagaa    12900
ttgtttattc aaatctttca cccacttta aattggatta tttgtctttt cattttata      12960
gttgtaagag ttcttatat gctctggatc ttagaccttt atcagatatt atatttttc       13020
ctcccatcat ttgtattgtt tttatttc ttgatagtgt cctttgaagg acatttttaa       13080
cttttatgaa gtccaattca tttactcttg ttgcccatgt ttttgttttc atatcaaaga    13140
aactattgct taatccaaga caacaaagat ttacatctat gttttattct aagagctta     13200
tagtttcagt ctcacatgtt ggtctttgat tcatattgag ttaatttatg tacgtggtgt    13260
gaggtagggg tccaacttca ttcttttca tgtggctata cagttgttcc tgcatctgat     13320
attgaaaatt atatttcccc tcattgaatg tctggacacc cttgttgaaa ataaattgaa    13380
```

```
ctcaaatgta tgggtttatt tctgacctct ccatggtaat ccattgatat ataatccta    13440 tgccaggacc agacagtctc aattactgta gcttggtgtt tagttttgaa atcagttttg    13500
tctttcaatt atgtttttat tttcttaaaa tcatttatac tgatgaaatt gctgatattt    13560
attttatgga ttgactacct ttttttaggg attagtatat taaatagctt tataatttaa    13620
atgcaatcta aatctctctg gtgatgtcat atctctgagc aattactaaa ccatgtgact    13680
ccatatacta gtaagtatgg tccagtgagt ggcatggaca gaagtaatga cagactgtag    13740
agaagtggtg gggagcttaa gagtattctc ttccttatag ctctcaagat ccgttttcat    13800
tctcccatta gattttgatg atatgctcat catttggtaa gagcacatga taatatatta    13860
agtataatgt tattgattta tttagagaca gagtctcact ccatcaccca ggctggagtg    13920
cactggtgtg ttcttagctc attgaaatct ccacctccca ggttcaagca attcttgtgc    13980
ttctgcctac caagtagcta ggattacagg catgtgccac cacacccagc taattttgt    14040 attttagta gagatgggtt tttgccatgt tggccaggct gttctcaaac tcctgacctc    14100
aagtgatctg cctgcttcag cctctcgaag tgctgggatt acaggcatga gtcactgtgc    14160
ttggcctaag tataactctg taattgtcct atctgtttaa aacatctttc cattcataat    14220
tcccttattt tcttactttt gatatataat tttattttta tgtagtgaca tctatataat    14280
aaaatttcag atggttcaat ttgggcacca aggtgggagg gatcagggac tggtgtgaaa    14340
ttgatacaga aatagtttc ctataaagcc acaaataagt gatacttgga gaagaaagaa    14400
cttgtctttc ccccttgaat aatcttggca tcctcatcaa acatcacttc accagagatg    14460
tatgggttta tttctggact ctccaattcc attttgttca tctgtatatc tgtcctgggt    14520
cagtaccaaa ctgtctttat tactcttttct ttggataagt ttgaaatcgg gaaatatgaa    14580
tcattttact ttttttttt ttgagattgt tttggttcat gcataaacta atttgggacc    14640
atcattttcg taataatgtt taaaaatgct tgtggtccat gaacatggga tttttgttcc    14700
atttatttgt atcttttaaa ttttcttta acaatatttt atagttttca gaatataggt    14760
tttacccttc ttttgttaaa tttattccta agtatcttat gtctctttaa tgctattgca    14820
aatggaattt tttctttatt ttaaaattat ctatgatttc taactctcca ctccttgtat    14880
acttacctaa gtatgtgtct tatttccccg tactagtcca tatgtatatt aaggacagat    14940
tttatgtttg agtcatcttt gtatctcaca gactattagc ccagcatctt acacgtagta    15000 gttttcaaa tgtttaatta ataatttatg gattgttaat caacaccata aattaatgaa    15060
aacccagagc taattttgaa taatctagga agcctgtttt tttaacatat gttctttgga    15120
aatttgttat gaattaaata tcaggtactt tttgatatca atatgaacta gttttggatg    15180
ttatacaata ttttttatcc ataaaaaatt attttaccta aatataactc acatggttga    15240
actacataac tcttagtcac cacagcaaag gctgtttcaa aatataaagg ctgctagaaa    15300
tggccaaacg ctttctagga ataactcagt ctaattgtag gcaaatacag ggctatccct    15360
ttattttaag ttgtaaactt ataaatctaa tgactaatcg gttataatat actttcacaa    15420
cttccaatat ctttaactgt gactctattc cagaggcttt cacagattca acttctgtct    15480
ttgcactgac agctctcata tagcctgagg tctacatttc tcccattaac tctaggacca    15540
tttaattcaa atatctagta gatatctcta cccagatgta ctatggcacc tcatgcataa    15600
tagtcaacta attgccatca catttagcct gttcctgctt ctgtattctc tatcttaggt    15660
aattttagca ttttcctagt cttttcaattc tgaaagccta gaatcatctt tgatggcctt    15720
catctcatcc atcaccaaat tctatagttt aatatatcat cttaacacct gtattatcca    15780
```

```
tctattctat agacttctac tactagtctt agttcaagta gttgtcgat ctcaccggga    15840 ccacttctgc agctgtcagt gggccctgac taaccttcct gcctcccctg tgcatctggc    15900 cttttaatg atgcttgagt tatctgtccc gattcaaatc tgttaccatt tttcttcttt    15960
ttaaaaactc tttaatgaag tatctctccc ccagcaccta tcaggatttg gtcttgcatt    16020
tgattggttt gctaacagaa gtagccaaag aaggatcaaa ttctagccaa atattgcttc    16080
aaaaatatgt gtaaataaat ggacaatgtt taaataattg tagttaacaa ataaggaaaa    16140
tgtaaattga ttacaataaa aattagtttt ttaatatcaa tttatgctag agtaaaatat    16200
aaatttcctg tttatatgac tcagtagcat gactaatcag ttgcaattta acaagagaca    16260
ttgcttttta agaggcaagg ctttttgttt tatgaataac ttttttctag ttataaaaat    16320
taaagaaaaa tagactaatt aaaagataga gactgcctga gtagatttta aaacccctac    16380
tttacgttgc ctaaaagaaa cctactttaa atataaagat acatatagat tgaaagtaaa    16440
aggatgggga atgatacact atgttaacac taatcaaaat gggagtagct atattcattt    16500
cagtcaaagt caacttcaga gcaaggcgga ctatcatgga tataaagagg gtgcattaca    16560
taataataaa gggccaatta tccaagaaga cataagaatc cttgctctgt acatatctaa    16620
aaacagcatc aaactctgtg aagcaaaaac tgataaactg caagaaatac atgtatctat    16680
tattatagtt ggaaacttca cagccttctg tcagtaattg acagattcag cagggaggaa    16740
atcagtaagg ttacagatga acttgaaagc accataaatc aactggatct aattgacagt    16800
tataaaatac ttcatcaaac aacagcataa tacacatttt tctcagactc acatggaata    16860 ttcccccaaaa ttgaacatgt actgagccgt aaaacacacc ttaacaaatt tttataaagt    16920
acaagtcatg cacaacatgc tctcaaccaa aatgtaattg aagtagaaat caataaaata    16980
agaaaaatag gtggaaaatt cccaaatatt tggaaattaa aaacacaatt tttgataaca    17040
tatgggtcaa acaaaatgtc tcaaaagaaa ttttaaaata ttttgaatta atgaaaaga     17100 aaatagatat ttgcatgata cagtgagagc agtgcttagg gtattaaatg catagaaaga    17160
aaagaaaaag atataaaatc aatagtctaa tcttccacct taggaaaaca gaaatgagaa    17220
agaaaattaa aactaaatta atcagaagaa aataaataat gaaattagag atgaaattga    17280
gaacaagaaa ttagtagagg aaaatcaatg aaaccaaaac tggttctttg aaaagatcaa    17340
taaaattaat aagcctccag ccaggctgac cacgaaaata agaaacaaga cacaaactac    17400
tactatcaga agtgaaaaga gagccatcac tactgattcc atggatatta taaagataat    17460
gaggtaaaag tattttgatg gttaatttta tgcattaact tatcttggcc aaggaacacc    17520
aaggattgcc agcagccacc aaaatctagg agaaagtcat gaagtggttt caccacagag    17580
cctccaaaag gaaccaaccc tgccaacact ttgatgtcag acttatggct tccagaactc    17640
tgagagacta aatttctgtt gttttaagcc accctgttca tggacatttg ttatagaagc    17700
cctaggaaac tcaaataaat ggtgacaaaa gtggacaaca tcctgaaaaa aaattcacta    17760
acactccact ttgaagagag gccgtggaaa tgtctactgg ggaaaagcaa gtgaattggg    17820
gaaatgaccc ctaaatatgg tagtctctat gaaaagcaaa acacctcttt ctcagttggg    17880
aggaaacttg aagaccaaat gagcactctt tcctcatgca ggccagctca ccatacacca    17940
tgatgcactt taacaaaagg taaattgtta aaagagagc acagtgttaa taacagggaa     18000
ggctatgcat gtgtggggac agagagtatc tgtgggaaaa aaacagtttt cttattctc     18060 tcccctcaaca acaatcaaca taggagactt ctatgaccaa atgtgtgaga gtttttttcc    18120
```

```
tcatattcta agcaaagaat caattctgca aaggacacaa gctggctgtc aattcaatta    18180
tgacactatc tatctgaaga cagcaccaca tagcacaggt tgaggctgtc ttcatgactc    18240
ctccttcccc ctccacccccc atttcagatg ccaatcacaa accctaggat gtctaacctg    18300
tgcttctgac caactggctg tacaatgggg atcccacaac ctgctccttg ggtttaacta    18360
atttgctaga gcagctctca gaacttgggg aaatactaat atttatcatt tcttataaag    18420
gatattacaa aggtacagat gaagagattc atgggcaaga tatgggagaa caggtctgga    18480
gctttcttgc cttctctggg catgccaccc tccaaatacc tccacatgtt cagctatttg    18540
taagctctct ggagagttag gcatgactga ttaaatcatt ggccattggt gatcaacata    18600
accttcagcc cctctcctct ccccagaagc tggggatgg ggccgaaagt cccaaccctc    18660
tatttatgcc ttgttatcct aggggctggg actgggctg gagctggggg ctgcctaggg    18720
gctgccagat accagtcatc tcattagcac agaaaaagac attcctttgg aggtttcaag    18780
gattttatgg gttgtgtgtc aggaatctgg gacaaagacc aaacatacag tcatacgaca    18840
caatgtttca gtcaatgagg gactgcatat accatgatgg ccccataaga ttataatgga    18900
gttgcaatat tcatattgcc tagtgacatc atatctgtgg taatgtctta gaatgcatta    18960
ctcacatgtt tgtgatgata ctgatgtaaa caaacccatt gcactgccag tcatataaag    19020
gtatagcaca gtagtgttca gtaatgtcct aggccttcac attcactcat ggctcactca    19080
ctgactcatc cagagcaact tgcagttctg caagctccat tcatggaagg tgccctatac    19140
aagtgtacta ttttaatat tttataccat attttactg tacctgttct atatttagat    19200
atgtttagac acacaaatac ttaccattgt gttattatta tctatttagt gcatgctatg    19260
caggtttgta gcctgagagc aatagactat accttatagc ctaggtatgt aataggctat    19320
accatttagg tttgggttct atgatgtttg tgcgatgatg aaatcatcta atggcaccat    19380
tacaatgaca catttctcat aatatatccc ctatcattaa gtgacacata actgtatttc    19440
acagtatcac aatgtacatg aggaatctct ataccttctt ctcatttttt tgtggaccta    19500
aaattgctct ataaaatagt ctttaataaa aagagagaaa gaggacagtc cctgtccacc    19560
aacaaaattg accacaggtt ttcccacttc tcagtgcact accattgcca catacccctt    19620
cgcatatagc tgtgttccca ggcttttccaa gagcacacag agcagataat actgtggctt    19680
cacttagaaa ttcaacagag aagtgactgt gataagtgag aagaggatca tgagatatgg    19740
agtcaaataa atatcagcac agagtggtcc actttaaatt taagatgaaa ataacataca    19800
acgatacaga aatgccacag caaaataaaa agactaaaag aaacctagaa tataagcatc    19860
cattctggaa gggggcagac acgaagaaac agaataaaaa ctttcatttg tacttcacgc    19920
catagtttta aagtacacat gaattttaca acagaatatc aaagagtagt tgataaaaga    19980
atagaatgag atgaaaaaat attatacaac caaggaaata cattgaaatc caaaattatg    20040
cactccctcc attttagatg tgacaaaagt gttagcaaca acaagaagaa tgaacaaaaa    20100
atatgaaata gatttgttat aatcaccata aatgcacagt aaaaatacaa ataccaaaca    20160
gttgctgaaa caataaaaga taagaagaga tgatagtgat ccatttttatg aataattgtt    20220
cctaccaaag aaaattcatc gaatggaaga ataaacaac ctatgataga ggaaattttt    20280
tccacaaatt gaggcaaaat ggaatgaaca gtgctaggta gtatatcatg tactataaaa    20340
attgattcaa catgattgtt actaagttat atcttggaaa agtgactgaa tttcaagagc    20400
aaggaagaat aattctaaag gtggaaatgg caagtcagtt ggaggagaat cagagtggct    20460
tcagattttt cacatctaaa tgcaaaagat aatggaataa tgtctacaaa attctgagag    20520
```

```
ataaaaatgt ggctcagaat ttgataccta gacaagatgt tgttcaaata taaagtgcac   20580
aggcagaaat ttatgtatgt cagaatttag gcaatagaac actcatgagc cttttcaagg   20640
agaagatgga gggggagggg agctactgga tataaaatcc aaccaaccaa gagaaaagtg   20700
aagacactgt agtaaaaggt caattgatag cacaaaattc acttccttgt agaattagag   20760
tagcctcttc aaaatatatt atattctttt attttcctca tggttcttgc tactgtctca   20820
aattatcata tttttaggac agagactctc tgtcttgata atccttgtat ccccaccatc   20880
tagaatgtta cctggtacag acaagaccct tcataaatat ttattgactg actgagtgaa   20940
tgaacatagt ttacattaaa aaaaacttaa atgttatttt aaagttataa aattacagtg   21000
tagcataaaa ttatatgtta tatcgtgtat atagtataat tcaaaattat gttgtaaaga   21060
tgttgatata cataagtgac tgtgttagac acttctggct gccatatcaa agaaccatgg   21120
actttggtac tttggtggct tataaacaag agaaatttat tcctcacagt tctggaggct   21180
ggaagtccag gattgggtg gcatatggtt gggttctggt gaaggacctc ttccaggttg   21240
tggactacca gcttctcata tcttcacgtg gcagaatgtg aaattttcag atggctagag   21300
agctctctgg tgtttcttta taaggcacta ccaccattca ttagaggttc accttcatga   21360
cttaattacc tcccgaaggc ctcactttct aacgacaaca cattgggggt taggatttca   21420
acatatgaat ttcgaggaga cacaaatgtt cagttcataa cagtgacatt ttaaaatcat   21480
tatatgactt atagtcttca ccatattggc tctatcagtg acttctcact attggtttat   21540
gtgctactca tatatttact tgcagtttac ctaatggctc gcttattttt gcttaaccag   21600
gtggtgttta gagttatgct ctcaaaacag aacactctct tctgacagtt tggtttatca   21660
tacttggctg ctttgcttta catatttctt taataaatct ttatctttga tctgcctgtt   21720 accacccac ttcagctcac tagaatcttc gaatatatcc atctcatact tcatctctca   21780
aattgtctca ttaatcacag gttatatagt tgaaattgat atttaaagtt caagtaaata   21840
gttataaagt acagcatata agcatttgtg attataaatt tacagttgcc acatatgtta   21900
attggtaatt agatcgctgc ttgtaggatg gtatataacc attactgcat attaaccta   21960 agactaatga gtgagagctg ggccatgatg gctgactaga cacagttgca gttggaggcc   22020
tccaccgaga ataacaaaaa cagcaagtga atcctgtgct ggcaactaag gtatccaggt   22080
tctctcattt ggactgacta ggtggttggt gcaactgaca gaaagcaaag aaatcagagt   22140
ggagtaatgg cccacctgca gggggtaagt gggactccca tccccagcca agggaggcag   22200
tgagtgattg gccatcctgc ccaggaaacc atattttcc gtggatgggt gcaacctgca   22260
aatcaggaga ttcccatcat aagcccacac caaagggcc ttgggttcca agcacagagc   22320
agtgcatatt ctctcagtgg ccactgggct ggggtctgcc taagactaca gagttcctag   22380
agggaagggt agccaccatc gctatggcta cctgctgcct aagatgactg aacttagaaa   22440
aggggcagca accatcactg cagctccagt ctgccttttc ccctgctggt gccagagata   22500
ttgggtggtt cagatccagg aggaattctc cacagtgcaa cacagcagct gtggcagata   22560
atcaccagac tgcctctta ggctgcaccc ggacccatcc atcttcactg catgtggcct   22620
ccctctggga atttcatcat ctccagccag gggtttacgg acagagctct gatacccctg   22680
ggatggagct tctgggggga ggagcggctg ttgtctctgt ggatcagcag acttagtctt   22740
ttccccgctg gctctgagga atccaggcag ttcagacgag tgggattcca gccagagtgc   22800
ttcattaagt gggtctttga tcctgttctc ctgactgggt gagaccaccc ccaacagggg   22860
```

```
tcaccagata ccttatatag agacattccc actaacatga agtcaataac cctctgggat    22920
ggagctccca gaggaaggag cagtaagcca tctttgctgt tgcgcagcct ccactggtga    22980
cacccccagg ggtgggagag acccaggcaa atagggtctg gagtgaaccc ccagcaactg    23040
acaggagcct tatggaagag gggcctgact gttaaaagaa aagcaaacag aaagcaacaa    23100
caacaacagc atcaacaaaa aggcacccac agaaacccca tccaaaggtc agcagcctca    23160
aagatcaaag gtagataacc tcagcaagat gagaaacagt caatgaaaaa acactgacaa    23220
ctcaaaagcc agagtacctc ttcttgaaat gatcgcaaca cctttccaac aaggcacaga    23280
actgggctga ggctgagatg gataaactgg cagaagtagg cttcagaagg tgggtaataa    23340
tgaacttcac tgagccaaag gagcatgtcc taacccaatg caaagaagtt aagaaccatg    23400
ataaaacatt atagaagctg ttaaccagaa taatgtttag agagaaacat aaatgacctg    23460
atggagctga aaatacaac acaagaactt cccaatgcaa ccacaggtat caatagctga    23520
atagatcaag tggaggaaag cacttcagaa cttgaggact atcttgctga aataagacac    23580
aaaattagag aaaaaaggca tgaaaagaaa tgaacagaac ctgtgagaac tatgggatta    23640
tgtaaaccca caaaacctac gcctgattgg ggtacgtgaa agagatgggg agaattgaac    23700
taacttggaa aacatgcttt aggatatcat ccaggagaac ttcctcaacc tagcaagaca    23760
gggcaacagt caaattcagg aagtacagag agccccagta agatacgcca tgagaagaac    23820
cactccaaga cacatgatca tcagattctc caaggttgaa atgaaggaaa aaatattaa    23880 gggcagccag agagaaaggc caggtcacct acaagggaaa gcccatcgga ataacagcaa    23940
acctctcagc agaaacccta caagccagaa gagattgggg gccaatattc aacactctta    24000
aaagaaaaat gtttctaacc agaatttcat atccagtgaa actaagcttc ataagcaaag    24060
gagaaataaa atccttttcca gacaggcaaa tgctgaggaa atttgtcatc accaggcctg    24120
ccatgcaaga gttactgaag gaagcactaa atatggaaag gaaaaatgat taccagccac    24180
tacaaaaaca cactgaagta cacagaccaa tgatactatg aagcaactac atcaacaagt    24240
ctgtaaaata accagctagc atcatggtga caagatcaac tgcacacata ggaatattaa    24300
ccttaaatgt aaatggccta aatgccccaa ttaaaaggca cagagtggca agctggataa    24360
agagtcaagg tccactagtg agctgtattt aagagacaca tctcatgtac aaagacacat    24420
ataggctcaa aatagtaaaa tctaccgagc aaatggaaaa cagaaaaaat caggggttgc    24480
aatcctagtt tctgacaaaa cagactttaa accaataaag atcaaaaaag ataaaggcat    24540
tacataattg taaagggttc aattcaacaa gaagagctaa catcctaaat atatatgcac    24600
ccaatacagg agcacctaga ttcataaaac atattcttag agacatacaa agagacttag    24660
actcccacag aataatagtg agagaattta acactgcact gtcaatatta gacagatcat    24720
tgaggcagaa aattaacaag gatattcagg aattgaactc agctctggat caagtggacc    24780
tgatagatat ctacagaact ctccacccca aaataacaga atatacattc ttcttggcac    24840
cacatggcac ttactgtaaa atcaaccaca taattggatg taaacactc ctcagcaaat    24900 gccaaagaac tgaaatcaca acaaacagtc tcttagacca cagtgcaatc aaattagaac    24960 tcaatttaa ggaactcact caaaagcata caattcatg gaaattgaac aacccgatcc    25020
tgaatgactc ctcggtaaat aatgaactta aggcacaagt caggaagttc tttgaaatca    25080
atgaaaacaa agaggcagtg tgccagaatc tctggaatgc agctacagca gtgttaagcg    25140
agaaatttat aaaactaaat gtccacatta aaagctaga aagatctcta gtcaacatcc    25200
taacatcaca atgaaaagaa ctagagaacc aagggcaaac aaaccacaaa gctagcagaa    25260
```

```
gacaagaaat aaccaagatc agaaaagaat tgaagcagat gtagacataa aaaacccttc   25320
aaaatattaa tgaatccaga agctggtttt tgaaaaaaat taataaaaca gactgctagt   25380
tagactaata aagaagaaaa gggagaagaa tcaaatatac acaataaaac gataagataa   25440
atatcatcac tgaccccaca gaaatacaaa caaccatcag agaataccat aaacacctct   25500
atgcaaataa attagaaaat ctagaagaaa tggataaatt cctggacaga tatatactcc   25560
caagactgaa ccaggaagaa gttgaatcct tgaataggcg aataacaagt tctgaaattg   25620
aggcagtaat aaatagcctg ccaaccaaga aaacccgcga ccagacagat ttagagctga   25680
attctaccag aggtacaaag aggagctggt accattttt ctgaaattat tccaaacaat   25740 tgaaaggag ggactcctca ctaactcatt ttatgaagcc agcatcattc tcacaccaaa    25800
acctggcaga gatactacaa aaaagaaaa cttcaggcca acatctctga tgaacgtcaa   25860
tacaaaaatc ttcggtaaaa tactgccaaa ccaaatccag gagcacatcg aaaagcttat   25920
ccaccatgat caagttggct tcatctctgg gatgtaaggc tggtgcaaca tacaaaaatc   25980
aataaatgta attcatcaca taaactgaac taaagacaaa aaccacttga ttatctcaat   26040
agatgtagaa aaggccttg ataaaattca acatcccccc atgttaaaaa ctctcaataa    26100
actagatatt gatggaacat acctcaaaat aacaagagcc atttatgaca aacccacagc   26160
caatatcata ctgaatggac aaaagctgga agcattcctc tagaaaacta gcacaagaca   26220
aggatgccca ctctcaccac tcctgttcaa catagtattg gaagttctgg ccagggcaat   26280
caggcaaaag aaacaaataa aggtaggcaa ataggaagac aggaagtcaa actgtttgcc   26340
gatgatgtga ttttatatct agaaaacccc attgtctcag cccaaaagct tcttaagctg   26400
ataagcaact tcagcaaaat ctcagaatac aaaatcaatg tgcaaaaatc acaagcattc   26460
ctatacacca acaatacaca aggagaaagc aaaatcatga atgaactccc atttacaatt   26520
gctaaaaaga ggataaaata cttaggaata cagctaacaa gggcaagtga agacctctca   26580
gggagaaata caaaccactg ctcaagtata tcagagagga cacaaacaaa tgaaaaaaca   26640
tgtcatgctc atggatagga agaatcaaca ttgtgaaaat ggccatactg cccaaagtaa   26700
tttatagatc caatgctact cccattaaat taccattaac attcttccca gaattagaaa   26760
aaactaccat aaaattcata tggacccaga aaagagccag tattgtcaag acaatcctaa   26820
gcaaaaagaa caaagctgga ggcaccatgc tacccaactt caaactacat tctacaaggc   26880
tacagcaacc aaaatagcac agtactcata caaaaacaga cacgtagtcc aatggaaaag   26940
aatagagacc tcacaaagaa gaccacatat ctacagccat ccgatctttg acaaacctga   27000 caaaacaag caatggggaa aggattccct atttaataaa tgtttcctta atattccatt    27060
attttaaaca tttattaagc atctgctaat agtaatctgt caactcaaat ctgaatgatg   27120
tattcccctc ttcaagaact ctagtgactc agagtggaat aacaatttta atgggacttt   27180
gaagaatgta tagttcttaa ggaggcaaaa atgaaaggga atgccatttc atcagagagg   27240
actatttgag tcaaagcttc gaatcctgcc tttccatgca atttttgcatg catttatgaa   27300 atggctgtta aagattgtgt gcaagctgtt aaataatgag cacaggtata aaaaagacca   27360
gtttaccaga ctatgaggtt tagttttgaa agagagctag actcttaaat aaagaattgc   27420
aatgcaatgg gataatgctg ataattacag ttgaaaatgt ttagggatac caactaattt   27480
gacctggggg cttggtaatt agatttaagt caatggcccc atgtagctct agaggagatt   27540
tggatgtaga aaagttggaa ggtagggtat ggctagattt gcaagacct tacataccag    27600
```

```
gccgaagaat gtgaacttga tctttaggac tatataataa ggagcgatca ggcttttaaa   27660
ctgcagcagt gtagaattaa atctgggatt tagaaagata attcatatgc gccatataaa   27720
ataaatttgt gatgaaaagc attcagaaag ataggttatt tcagcattcg tagttggcac   27780
tgttgagtat ggcatgtttc ttttttaaaaa ccatagtaaa atttacagat ggcagctgat   27840
gtcctctgaa agtttgggag tatgtgattg atgatattgt cattcaatca gtaattttta   27900
ttacatgaaa atacaatgga aaactcaaag attgataaaa tatagttctt gcattaggaa   27960
caagcaaata aaaggcagta gtgaatgcat ggagtcctta aaggtagttt cccaaaagga   28020
agagtaaaac tgaaatggcc cccagcacct ggagagaaaa aggagaaact gcaagttgga   28080
gcaatgagat gaatgctaat gccacaacat aattacaaag tccgtcctag tgaagaagga   28140
aggcactttc agattgccct ttttatagg tgcctgttgt tgtcaaggcc tgttctcata   28200
cctggccaga cttccattaa gtctgtgcat tcaactttga ggacaatgat gcgtctaata   28260
ctcccaggcc tgaatagcta ttttatgaaa attactatat tggtatttt atttgttttg   28320 aacccacatc tatgcctgca ttagatatta taaactttat tatctagctt ctttaccatg   28380
tgcagataga ggtgaatctc aactagacaa ccgatgaaga cattgtcgat cacataatga   28440
taatatttgt gcttcagttg ttttctctt aatggtgctt attatgcagg ttattaattc   28500
aaagaccatc attggtattg aggaatgtga gagtaggaat gtcatttata gagatgaaaa   28560
gtttctattc accatgaaga tcacagatgt tttcatctgc cagggagtaa tttatactgc   28620
atctacttat gttatgaccc gtgtggaccc tgtgtcaata ttgaatctga atatgccact   28680
tgctagctat gtgacattgg ataaattact taatccttct gtgccttagt ttccttattt   28740
ctaaagtggg gataaaatta ggacccatac ttcatagggt tattttaaat aaattaaatg   28800
ggctaatata tgtaaagctc atggaacagt gcctggaact taagcattca acaagtcata   28860
gttcttgtca tattattaat gttagaaata atgtctgcaa caatgctctc taaatttcct   28920
atctcacatc cttaagaaca gatgcaaata aaaacctgta atatttgaaa atggctagaa   28980
attgtgtgat ttatgagagc aaaattcaaa catacacaat atgattttgc attcacttta   29040
gtcccctctt atccaacatt tcagcttctg tggtttcagt tacccaaaaa tcaatgaagg   29100
ttcaaaaatc ttctatggaa acttccagaa ataattcgta aattttaaat tgtgtgccgt   29160
tctgagtagc atgatgaaat cttgcactgt ctcactctat cccatccaag gggtgaatca   29220 tcccttttgtc tagcagaacc gggctgtgga tgctacctgc ccattagtct catagtagcc   29280
ttttagatta tcagattggc tgcagaggta tctcagtgct tatgttcaag tcattcttac   29340
tttacttcat aatggcccca aaaagcaaga gtagtgatgc tagaatattg tcataattgc   29400
tctatttcat tattaggtat tgttattaat ctcttactgt gcctaattta taaattaaag   29460
ttttatcatt ggtatgtatg cataggaaga aaagtaccgc atatataggg tctggtacca   29520
tgtatggtct caggcatcca ctggtggcct tggaaagtat cctccaagga taaggggtac   29580
tactgtagag aatgtagaag tggctatta ataaccacta aatatttatt tagcatggaa   29640
gtgtttgaag taaatctta cacagaggtc cagtgaagtc ccaagccctg actatcctgt   29700
atcatcctta cgcttacttc taagcgcccc cccagttacc ttatgaaatc ctaggactac   29760
atggaatatg atctatgaaa accactgccc tagtccaatg tactcatttt gcttatgaga   29820
aaattcaagg agaggttaca gtaagtcagt aaaacgctac aggaagaaaa aggactggaa   29880
atgaaatgct ttggtcagag tccccacttt gcccctttgg ctatgagatg ttggacaatt   29940
cagttaactg cttgaaagcc tgattttcc aattagaatt ttgattttca taatctctga   30000
```

```
gatccattcc tgctgtaaaa ctattcaatg tcagaaatgc acacagtcat ccacaaactc   30060
tagtttggtg ttcttttcat tgcactgatg tagaagtatc gactacttag gagaaccaaa   30120
gaatgaatgc cctggatgaa ttccataata acctttctgc acatccagag taggatatgt   30180
ataattttgt gacgtatggc actgtaccaa gtacaggtga atatgccgtc aggttttcaa   30240
tagttatgca gtgtgtgtat ttaacatgaa cactgatagc taggcaaatc tgccaattgt   30300
tgaatcatat agttcctgga acaccatttc ttatccccaa acttatataa ccacacctgg   30360
attaaagtaa attaataaaa tactacgttg tgtacctaag gtgtgttggt aaagctggaa   30420
aaggcaactc atgaataaaa aatatatatt acctccagaa aaataaatgt aatgcataca   30480
caactttaca caagttaaag aatgggttta acaactaaga tttgttcatt accctttcat   30540
gagacattct tttgttctgt attcattaca ttattagatt ttctagtgaa tttcaccaat   30600 tgattttct taagttgagc ttcatcagag aaattctgta gaggtatttt cacaaatgaa   30660
aactcacaat cacaagtttt ctaactcttt tgcataaaaa agcactgagg cactttcat   30720 gatgatatta ttctgaaaca ccatatttaa gaatatagtc attttatc tttgtttgtt   30780 ctttatgtcc taatgttctc tacagtggat tccatcaata ttaattgtta aaatattaac   30840
tttctatttc tgccattgtt ttatgtacca cagagacatg tattagaaaa cacgctatgt   30900
tatgggtgta agttaaatga gaagcacagt gccataaaat tgcacgagaa ttgctttact   30960
tgggctattc ttggtcatag gaaggactgg gaaattaata tagtcacgtt tttatagatg   31020
cagagctttt attaattaac atacagttgt taattagtag tatatgttca cctttgttat   31080
taacataaaa tttagtacaa aacacttttg ggatattaaa ttttggtatt aaatatgtcc   31140
tatttcatac atgttagaat ataattaata tatacttatt gtcatcacaa agaatcaatg   31200
ctaaagtcaa aaaattccag gtacttttt tccttcttgt taacctagca atgttgggca   31260
ttagatgaag aagaggcaag gctacagggt tagataagga tctgcagtct tagtctttgc   31320
aaatacttgg tatctcttgc cttctcaaaa cttaggcatt gaaaattatt ataagtaatg   31380
aaatccaaaa tgttagatag ggtaaacaca gttgaactca caaatatatg tttttttttc   31440
ttttctctgc tcttttggta gaaaatgtag aacatgatta ataaggttgg agttttttct   31500 ttataattt tttcacagtg gcgttccaaa ctaaagaatg cttgtttacc taatatggcc   31560
aaattggagc cagtaccttc attcagctag atttacccca gttgcatatt tgcaatgagg   31620
cagaattcct acagacagcc ttccttctga tttttctgcc tttgttcctc ctcacactgt   31680
gtttctccca taattcacat ctaccctcta cctaattggc ttctccagtc aaagtggata   31740
agcatctcag tcagaaatac attatgagaa cttcccaaac atgtactaat cgccacaaac   31800
caaggctcag atcatgccat atcgctgctc aacaactttc cttaggttac cactcactgg   31860
ctattgcagg actaattcct tatgtgggca ttggagaagg aaaatctgtt ctttacattt   31920
ctagcctact tgccactctg tattgcccct tacacgccca gcaccacaac caaattggat   31980
tacttactgt ttccaaaata tgctccacat ttttgtacct cagtgccttt gctgttttct   32040
cattgtggaa ttttctactt cccctgtctt gctccacaaa tcttcccgca cccaaattta   32100
aagacagcag gaattgaata acatcctttg ttcaataccg ttcgttatga cattgatgag   32160
aaaaaagtcc atttctggcc ctggaccact gtctgtgtag agttagcaca ttctccccgt   32220
gtctgtgtgg gttttctctg ggtactttgg tttcctccca catcccaaag acgtgccac   32280 tgggtgaatg ggtatgtcga catggtccta gtctgagtgt aggtgtgtgt gaatgcaccc   32340
```

```
tgtgatcgag ggtgtcctat ccaggactgg tccgtgcttt gtaatctgag ctgctgagat    32400
agactccagc cacctgaact agaataagca gtttggaaag tgaccctgaa ctagaataag    32460
cagtttggaa aatgaacaaa tcaatcaatg taaattattg tcaaataaaa atttgttaag    32520
taaatggtca ttatacaaat acacaacaat aaatgatgca agacgaaggt gctcatccag    32580
ctgtgagtca gccttacttg tttgtgattc tttttttaact gtgtggtgga agtgctcctg    32640
acagttttag ctttgcaaac acttatttct tgacttaatc caccaccact atgaccatcg    32700
acactcactg atttacaaaa acatgggtaa ttatcttgtt tttgttaatc tttcttaaat    32760
gtatgtgtag ctcatattta attcagtgtt taatattaga aatgtttggg gtcttcattt    32820
agaaatttgg cgatgttttt gtgatgagaa atatgccaca ggatcttaac tctttttat    32880 atcaattaac ctacggtaaa attggtttct ttgtacaaca gtttacttaa agtcgcagtt    32940
tccaagaacc tatccgtgat gttagatgag gacttactgt gccatttaag gtcaagttca    33000
ggttctactt tattcataac gcaagtcaaa agtagtctta ctgttgcact ttatcttgaa    33060
cactattaag gaaggtatca ttctatattt tatgcataaa atctgaatat gcatatacat    33120
tcaatatttt ttttaaagta gacatgtaaa tgactaagca aacaaaatgt attacaggct    33180
atgtcatgtg gtcagggctt aggattcaga aaataatatg ttgtcttgaa ttttgctagc    33240
acttatattg tcaactcttc tattaaattc tgttgattga aaattttgaa tcaagctcac    33300
attacttata tgacaaattc gggtaataga aaaagcatgg gctttgtaac caggcaaacc    33360
agtatttgca tgctagccct gccaatcatt agttttttcca cttagtgttt ttgtgaatct    33420
ggtttctttg ggattgtgga gtgtaatgat agtgacagtt gttagatatt gcttgcactg    33480
tccattattc taggaagaaa gtttcctgga ataggaaata taactgattg ttttcccaca    33540
ggagaagaag gcacttcctc tcctctttgg ggctagaaat gacttacttt aaaaatctca    33600
gttaagagag gactaaagct gttccaatgt tatgattgta ttccctaac tatgtgaagg    33660 tacagcagga gcaagccttt catttgtagc agtggctgca acagaagggg gggcagtttt    33720
tagagcggcc tggcacaggg tattagtttt tgaatcctcc aggctgaaga atgtgtgctt    33780
cctcagcatg tgtaagtatt tgtgtcagta tgctttcatg tataattagt agaaaactga    33840
acataaatgg acttaaacat taaagagtta tttaatggcc tgtataactg aaaagacccc    33900
agttgaatgc tttcaactgt ggcttagaat ttcaacttaa tttctttgca atttttgac    33960 tctgcgtttc tccatgtggc attaatcttc atgttgtggc ttaccagtag ccaccagggt    34020
ttctttattc ttccatatcc agcagaatga taattccttt gcctataatt aactaagttc    34080
ttagatgtac tctgattgga ttatctatga aaaaatcctt atgtcagcgg aagacccagg    34140
tcttaactgc cttagacctt gtttaattga gcaagttgct ttggtcagag agatgggata    34200
acctttattt acttagtatc taagtcttag accaatcaaa actcaagcca gagctggaag    34260
tggtattaac tttcattaaa aaaattactg ctaataatg gagagagaga aataggaatg    34320
atatgcaatg aaaaccacaa tgtctattgc gttgggaggt tttggagctc caacagccag    34380
gaaacagcta ggaaaacact ttctgacata ataagatctg tcccctctcc acaaatggag    34440
tgggaacatt agtgattccc actagagaag tagctttacc taggaaagtg gtgatttcat    34500
gaagttcgtc atttctatga cagcaagttg tggagaccaa ggagaagaac ctgaagagtt    34560
tattacagaa cacacattag ataacattat gggaattttc agaaattaca tggtgctttc    34620
agaggagttt atctccatca gataggaact taaaggctta aattataata atgtgtgtat    34680
aaaaaaagaa gagtgatttt attatataat cactggatag acaaaactgt aaagatctcc    34740
```

```
tataaagcaa aaggaaataa tttgtgtatc tgtctacata ctatcttcct acctatctca   34800
cttgtgtgcg tgtgcgtgtg tatgtgtgtg tgtgtgcgtg tctttgcata ttggtctgtg   34860
tatgcatatg tatatataat taagagaaga tgattgatac catagacaga gcagagagct   34920
aatctataaa taataagtgt ttctgaagag aaaatagccc atcaaaacag aagcaaaagt   34980
tcagaataaa agagagatat atttctgtat taaaatctta aacttgttga ttatgactca   35040
agggtaagag acaaacacta ggatatatca aggtgaattt tttcaaggaa gcatccttcc   35100
agtaagagag gggaaacatg tcgacaaaag gatacaatta ggttagcctc tatttttta   35160 ccaatgttta gctccaattg accaagctct actgaatttt gtgataacta ctaagttttg   35220
ttactgtggg ttcacagtct tagacccagg caaatttat tgaatgtacc aagaataata   35280
aagacacaga taggccagca agggtactgc ttctttattc aataaaaacc tgaccttaag   35340
attagtccat ttggcttttg ttgccactgc ttttggtgtt ttagacatga agctcttgcc   35400
catgcctatg tcctgaatgg taaagcctag gttttcttct agggtttta tggttttagg   35460 cctaacattt aagtctttaa tccatcttga attattttt gtatcaggtg taaggaaggg   35520
atccagtttc agctttctac atatggctag ccagttttcc cagcaccatt tattaaatag   35580
ggaatccttt ccccattgct tgtttttctc aggtttgtca agatcagat tgttgtagat   35640 gtgtggcatt atttctgagg cctctgttct gttccattgg tctatatctc tgttttggta   35700
ccagtatcat gttgttttgg ttactgtagc cttgtagtat agtttgaagt caggtagtgt   35760
gatgcctcca gctttgttct tttggcttag gtttgacttg gcgatgtggg ctcttttttg   35820
gttccatatg aacttaaaag tagttttttc caattctgtg aagaaagtca ttggtagctt   35880 gatgggatg gcattgaatc tataaattac cttgggcagt atggccattt tcatgatatt   35940
gattcttcct acccatgagc atggattgtt cttccatttg tttgtatcct cttttatttc   36000
attgagcagt gatttgtagt tctccttgaa gaggtccttc acgtcccttg taagttggat   36060
tcctaggtat tttattctct ttgaagcaat tgtgaatggg agttcactca tgatttggct   36120 ctctgttgt ctgttattgg tgtataaaaa tgcttgtgat ttttgtacat tgattttgta   36180
tcctgagact ttgctgaagt tgcctatcag cttaaggaga ttttgggctg agacaatggg   36240
gttttctaga tatacaatca tgtcatctgc aaacagggac aatttgactt cctcttttcc   36300
taattgaata cccttatt ccttctcctg cctaattgcc ctggcagaa cttccaacac   36360 tgtgttgaat aggagtggtg agagagggca tccctgtctt gtgccagttt tcaaagggaa   36420
tgcttccagt ttttgcccat tcagtatgat attggctgtg ggtttgtcat agatagctct   36480
tatgattttg agatacgtcc catcaatacc taagttattg agagttttta gcatgaaggt   36540
tgttgaattt tgtcaaaggc cttttctgca tctattgaga taatcatgtg gttttgtct   36600 ttggttctgt ttatatgctg gattacattt attgatttgc gtatattgaa ccagccttgc   36660
atcccaggga tgaagcccac ttgatcaagg tggataagct tcttgacgtg ctgctggatt   36720
cggtttgcca gtgacaaatg ggatctaatt aaactaaaga gcttctgcac agcaaaagaa   36780
actaccatca gagtgaacag gcaacataca aatgggaga aaattttcgc aacctactca   36840
tctgacaaag ggctaatatc cagaatctac aatgaactca aacaaattta caagaaaaaa   36900
acaaacaccc ccatcaaaaa gtgggcaaag gacatgaaca gacacttctc aaaagaagac   36960
atttatgcag ccaaaaaaca catgaaaaaa tgctcaccat cactggccat cagagaaatg   37020
caaatcaaaa ccacaatgag ataccatctc acaccagtta gaatggcaat cattaaaaag   37080
```

```
tcaggaaaca acaggtgctg gagaggatgt ggagaaatag gaacactttt acactgttgg    37140
tgggactgta aactagttca accattgtgg aagtcagtgt ggcgattcct cagggatcta    37200
gaactagaaa taccatttta cccagccatc ccattactgg gtatataccc aaagaactat    37260
aaatcatgct gctataaaga cacatgcaca cgtatgttta ttgtggcact attcacaata    37320
gcaaagactt ggaaccaacc caaatgtccg tcaatgatag actggattaa gaaaatgtgg    37380
cacatataca ccatggaata ctatgcagcc atacaaaagg atgagttcat gtcctttgta    37440
gggacgtgga tgaaattgga aatcatcatt ctcagtaaac tatcacaaga acaaaaagcc    37500
aaacaccgca tattctcact cataggtggg aattgaacaa tgagaacaca gggacacagg    37560
aaggggaaca tcacactctg gggactgttg tgaggtgggg ggaggggggag ggatagcttt    37620 aggagatata ccaaatgcta aatgatgagt taatgggtgc agcacaccag catggcacat    37680
gtatacttat gtaactaacc tgcacattgt gcacatgtac cctaaaactt aaagtataat    37740
aataataaaa taaaaagat tactccattt gaacaagata ttaataaata tcaataatag    37800
agaaatggtg atataaaaca atcactatta aatgctgcag tatttggtga tttctagata    37860
gctattgtaa atattaaaac acaaaaataa cttgtttcac ctaagcccta agaatataaa    37920
aagtgcgtgg ttatgggagg actgagaaag ctaaaaagat gataaatccc tccctttcat    37980
tagaatgatt agtggatatg tatactaatt agattggtag agaatataat tttaataatt    38040
attggaaaac actcttaaaa gaattatagt ctttcaaatt acaagaaaaa aggaaaatac    38100
aatgtagtca cttaaatacc aaaattatac caaaattata aaataaagga aaggaacaa    38160 aaagaaatag aatgactatc tgacaataaa tataaaattat gttaaactcc aaaattaacc    38220
tgattgttca cactcacaca cacacactca cttgttcaca ctgtatgcac tatataagag    38280
ataaacacag acacacacac acactcactc acactgtatg cactatataa gagataaacc    38340
taaagtaaaa tatcaaaaat tttttaatc ccttatataa aattatcaac tgatcattaa    38400
aagacaaaaa acttataaga aagtggataa gaacagacta ttcatagaaa agaagatgca    38460
aattgttaat taacatgaaa tgatgttcat cttcaagtag ttacaaaaat gcaaatgtaa    38520
gctataatga ggcataattt tttacttctc aggattggta aaaatggtaa agactgatga    38580
catctgatcc aaataagaat gtaacagaat ggcctccttt atatgctggt agaagcacaa    38640
attattttaa aaatacatat accatttat tcagcaaatc tcactttttgg gaactaagtc    38700 tacagaaatg caagcattaa tataaaatga gataacaaac acatacagat acacatacaa    38760
agatgtctgt tacagaattg ttggtaggag caaatatttg actattcatc aataagtatt    38820
gaataatttg tggaacacac ttaatgtgga atattacgca gttataaaac aattgttcta    38880
gtatgtttga cctagaatga cagtcatgat ataaagtgag aatgatacaa aaatcaaagt    38940
gtaatgtata cactgtgatc ctatttttta acaaaatgaa aaaggaaaat accctcataa    39000
aaccctatat atgcatgtat atatgtgtat tttctatgcc tgcagaccta acacgcatag    39060
gcataggatg ctgagctgaa agtatagagg tctcatatac tccttgtgcc cacagacaaa    39120 tttcccact atcaacagtt gctatcacag tggtacattt attatgatca atgactctac    39180
acatcattgt cacccaaagt ctatagtttta gattaagatt cactcttggt gttgtacata    39240
ctatgggttt tgtcaaatgt cttcaatcca aattatatta cagaatagtt tcactctcct    39300
aacaacttca ctgttcattc tttgtgcctc tcctattcat ccacttgctc cctcttaaat    39360
cttgacaaac cacgaatctt tttactgtct ctagtttac ctttttccaga atgttacata    39420 gttgcactca aactgtatat agccttttc agtttggctt ctttcactta ataatatgca    39480
```

```
tttaagatcc ttccatgttt tcttgttgct ttatagctca tttcatttta gaactgaaaa   39540
aatattccat tgtctggaag caccacagtt tacttattca ttcacctact gaaggacata   39600
ttcattcctt ccaagttttg gtcattatga ataaagctgc tataattatt cacatggggg   39660
ttttgtgtgg ccacaaattt tcaaattctt tgggtatata gcaaggattg ctgcattatg   39720
tcgtaagaga ttgtttagtt ttgtagaaga ccaccaaact gtctttcaaa gtggctgtac   39780
tgtttacctt cccatcagca atgaatgaga attcttttg ctttacatcc ttgccagcat    39840
ttactgtggt cagtgttttg ggttttggcc attctaatag ggtgtcatgg tatctcattg   39900
ttgttttaat ttgcatttcc ctgatggcat atgctgttga ataacgtttc atatgcttat   39960
ttgctatctg tgtatcttct ttgctgaggt gcttattcag gttttttgcc aatttttat    40020 tgggttgtaa attgtcttat tttagatttt taagagttct gtataatatt ttggataata   40080 ttatttacc agatatgtct tttgtaaata ttttttccag tctgtggctt gtaatctcat    40140
tctcctgatg ctgcttttg caaagcagaa gttctgaatt ttaatggagc tcagcttatc    40200
aatcacctct ttcatagatc atgcctttgg tatttattt aaaatgtcat ctcaatgccc    40260
aagttcatca agaatttctc ctatgtcatt ctctaagatt tttataatct tgcattttac   40320
attgaagtct atgatccatt ttgagctaat ttttgtgaaa ggttcaaggt ctgtgtctag   40380
attaatgtta ggggtgtgga tgtgaatgtc cagttgtctt agcaccattt gttgaaaaga   40440
gactgctcca ttttattgcc tttgcccgtt tgtcaaaaat caatggatta tacttaggtg   40500
agtcgatttc tcagctcata ttctggtcca ttgatctatt tgtctgtttt ttcactaatg   40560
ctatagtgtc ttgattactg taagtttatg gtaggttttg aaattgagtg gtgtcagtcc   40620
tctaactttg ctctttcttt tcaatattga atttactctc ctgggtcttt ttcctcttca   40680
cataaacttt agaaccaatt tgtcaatttc tacaaaataa cttcctggga ttctgattgg   40740
aattgcattg agtctgtcca ttcatttgga aagaactgac atcatgacaa tattgagtct   40800
ttctacccat gacctggaat atctctccat ttattttttt ctttttttga tattatttat   40860
cagagttttg tagttttcct catatgtatt ttggacattt tttttagat ttacacttaa    40920 gcattttatt tttagggctg ctaacataaa gtggcaatgg gttttaatt tcaaatttca    40980 cttgttcatt gatggtacat agaaaagtga ttgacttatt tctcttgtat cctgcaactt   41040
ttatataatt gctattagt tatcagagac ttttttacca atttaaaaaa attttctaca    41100
tagacaatta tatcatctgc aaacaaagac tgtattattt tgttcttacc aatctgtata   41160
cattttattt cctttttttgt cttactgcaa tagctaagtt ttgcagtaag atgttgaaag   41220
ctgaagtgaa gggagatagc tttttttta ttatcaggaa acctacaaat ttcttattat    41280
taagtatgat attagctata ggacttttgt agatgtcctt taagttgagg aagtccctct   41340
ctattcctaa tgtgttaaaa tttttatca tgaatgggtg ttgaatgttg tcaaatgctt    41400
tttctgcatc tattgatatg attgtgtgat ttttcttcat tggcctattg atgtgatgga   41460
ttagattaaa caatattcca atgttaaaac acctttgcat acctgaaatt aaatccactc   41520
aattgtggtg tagatgataa gtgctatccc caatagcaaa ttgaatccaa taatgtataa   41580
aagtatacag ttttatgtgg aggattttg aatctatgtt catgagaggt acttgtctat    41640
agttttattt tcttgcagtg tctttgattt ttgatattag ggtaatgctg gccttataga   41700
atgagttgag aagtattcct cctgctcctg cttacacaca ctgtcagata gtgtggagca   41760
ttgatacaat attgtcctta actatttgat agaattcagc aataaactca tctgggatta   41820
```

```
gtattttttg ttttgtaaca tcattttta tttattttct tgaatagata tagtcctatt    41880
cagagtttct atttcttttt gtgtgagttt tggtagattg tgccttttga gtaattgatg    41940
catttcatat aggttatcaa atttgtggat ttagagttgc tcataatatt tgtttattat    42000
ctgtttaatg tctattggat ctaaagtgat gtctctgtat cattttata tgaacaattt    42060 tcacttaata ccaatctaaa tctacttcca ataacatta taccacttta taggaggtac    42120
aagtaattta tggtaataaa atattactaa tttctccctc ctaaccttt atcactgcta    42180 tcattcattt cacttataaa taaacatata agcataattg aatacatggt tgctatcatt    42240
atttgaaggt attaactttt atatcaatta agaataagaa aaacaggctg ggggcgtgaa    42300
gattaaccac cccatgtgcc atcactggca ccaacaaatg ctgtccaggg ggctgcatat    42360
tggccaattc tactcaccac tgacagtgct tgtgtgcagc atctggtggc atgaggacag    42420
gtgcacctca ccataatttt cactaacaac cagagcctaa gccaatgaag aactctcaga    42480
caatgctgac attgatcgca tccaaataga acatacagag acgacactac tgtgctagcc    42540
cagaattaaa gccaaaacat cttccccaaa caatactata attacagcta caggaaaagt    42600
ctttctctat gaaagaagcc aatccatgaa attaaaagag aaactgttaa aatagatgca    42660
cagataaggt aaggacatga gaaatatgaa aattcaagaa aaaaatgaca cctctgaagg    42720
aatacaatac ttcttcagta aaatatccca aagaaatgta aatatgttaa aaagcctgaa    42780
aaagaattca aaataatgtt cttaagaaaa tgcagcgaga tacaagagga cacagataca    42840
aatacaagag gacacaatag aaaaaaaaaa atgcattggg aaggcaattc atgtcttcaa    42900
tgagaatttc aagaaagaga gacagatata aaaagaacc cggcggcttc tagcccgccc    42960
gcccctcccc cgcgcgtcgg ccctgccgag ccggccggcc ggcctggctc ccctccccgg    43020
ccccgacggg cgggcggact gccctgagga ggcggggagg ggagggctgg accggccggc    43080
gggcgggcga cgatgccgaa cttctgcgct gccgccaact gcacgcggaa gagcacgcag    43140
tccgacttga cttggccttc ttcagcttcc cgcgggaccc tgccagatgc cagaagtggg    43200
tggagaactg taggagagca gacttagaag ataaaacacc tgatcagcta aataaacatt    43260
atcgattatg tgccaaacat tttgagacct ctatgatctg tagaactggt ccttatagga    43320
cagttcttcg agataatgca ataccaacaa tatttgatct taacagtcat ttgaacaacc    43380
cacatagtag acacagaaaa cgaataaaag aactgagtga agatgaaatc aggacactga    43440
aacagaaaaa aattgatgaa acttctgagc aggaacaaaa acataaagaa accaacaata    43500
gcaatgctca gaaccccagc gaagaagagg gtgaagggca agatgaggac attttacctc    43560
taacccttga agagaaggaa aacaaagaat acctcaaata tctacttgaa atcttgattc    43620
tgatgggaag gcaaaacata cctctggacg gacatgaggc tgatgaaatc ccagaaggtc    43680
tctttactcc agataacttt caggcactac tggagtgtcg gataaattct ggtgaagagg    43740
ttctgagaaa gcggtttgag acaacagcag ttaacacgtt gttttgttca aaaacacagc    43800
agaggcagat gctagagatc tgtgagagct gtattcgaga agaaactctc agggaagtga    43860
gagactcaca cgtctttttcc attatcactg acgatgtagt ggacatagca ggggaagagc    43920
acctacctgt gttggtgagg tttgttgatg aatctcataa cctaagagag gaatttatag    43980
gcttcctgcc ttatgaagct gatgcagaaa ttttggctgt gaaatttcac actatgataa    44040
ctgagaagtg gggattaaat atggagtatt gtcgtggcca ggcttacatt gtctctagtg    44100 gatttttcttc caaaatgaaa gttgttgctt ctagactttt agagaaatat ccccaagcta    44160
tctacacact ctgctctttc tgtgccttaa atatgtggtt ggcaaaatca gtacctgtta    44220
```

```
tgggagtatc tgttgcatta ggaacaatcg aggaagtttg ttcttttttc catcgatcac   44280
cacaactgct tttagaactt gacaacgtaa tttctgttct ttttcagaac agtaaagaaa   44340
ggggtaaaga actgaaggaa atctgccatt ctcagtggac agggaggcat gatgcttttg   44400
aaattttagt ggaactcctg caagcacttg ttttatgttt agatggtata aatagtgaca   44460
caaatattag atggaataac tgtatagctg ccgagcatt tgtactctgc agtgcagtaa    44520
cagattttga tttcattgtt actattgttg ttcttaaaaa tgtcctatct tttacaagag   44580
cctttgggaa aaacctccag gggcaaacct ctgatgtctt ctttgcagcc ggtagcttga   44640
ctgcagtact gcattcactc aacgaagtga tggaaaatat tgaagtttat aatgaatttt   44700
ggtttgagga agccacaaat ttggcaacca aacttgatat tcaaatgaaa ctccctggga   44760
aattccgcag agctcaccag ggtaacttgg aatctcagct aacctttgag agttactata   44820
aagaaaccct aagtgtccca acagtggagc acattattca ggaacttaaa gatatattct   44880
cagaacagca cctcaaagct cttaaatgct tatctctggt accctcagtc atgggacaac   44940
tcaaattcaa tactttggag gaacaccatg ctgacatgta tagaagtgac ttacccaatc   45000
ctgcacacgt gtcagctgag cttcattgtt ggggaatcaa atggaaacac agggggaaag   45060
atatagagct tccgtccacc atctatgaag ccctccaact gcctgacatc aagttttttc   45120
ctaatgtgta tgcattgctg aaggtcctgt gtattcttct gtgatgaagg ttgagaatga   45180
gcggtatgaa aatggatgaa agcgtcttaa agcatatttg aggaacactt tgacagacca   45240
aaggtcaagt aacttggctt tgcttaacat aaattttgat ataaaacacg acctggattt   45300
aatggtggac acatatatta aactctatac aagtaagtca gagcttccta cagataattc   45360
cgaaactgtg gaaaatacct aagagacttt taaaaacagg cttcttata tttgatattt     45420 ggaagtaaaa gccgtaaggt gtatgtaggc cacttaatca ctaaatatct ttgcctatag   45480
gactccattg aatacattag ccattgataa tctacctgtt taaatggccc ctgtttgaac   45540
tctcaagctt tgaagaccta cctgttcttc cagaagagaa cgttgaaagt tccatgtttc   45600
cttttgcgtg atctctgttg acggcactct ggaattgttt cagttaagtc attttagaca   45660
tagcatttat tatcactgtg gatctctact tgttgggtgt tatgaattct ttgaaaaaat   45720
atattttgaa gaggtgtggg aggaaggaat acattttata aaatgttata gttaagccca   45780
caattgacct ttgactaata ggagttttaa gtatgttaaa aatctatact ggacagttgc   45840
aagaaattac cagagaaaag cttgtgagct caccaaacaa ggatttcagt gtagattttg   45900
tctttctcaa acttaaagaa acaaatgaca aagtttgaat ggaaaagcct gctgttgttc   45960
cacatctcat tgctgtttac attccttttgt ggagcctaca tcttcctaag cttttttagca  46020 ggtatatgtt gaacacttct gtttcatggt tgagacagaa tcagaggcca tggatactga   46080
caactgattt gtctggtttt tttttctgt cttttttcca tgactcttat ctactgcctc     46140
atcttgattt ataagcaaaa cctggaaaac ctacaaaata agtgttgtgg tttatctaga   46200
aaaatatgga aaatattgct gttattttg gtgaagaaaa tcaattttgt atagtttatt    46260
tcaatctaaa taaatgtga gttttgttta aagctaaaaa aaaaaagaa cccagcagaa     46320 atcctggaaa taaataattc agtggatgaa attaaatat atatatacaa tcaagagttc     46380
aacaatagac taaatcaagc agaagaattt ttgaacttgg tcttttaaaa taacaaagcc   46440
agattaaaaa aaaggtgggg ggggaata aagaataaa agagaatgaa gaaagcctaa     46500
tgacatatag gacaccataa agcaaacaaa tatttgaatt ttataagttc cataagaata   46560
```

```
agaaaatgga aatgccatag acaacctatt tattgaaata atatctgaaa aattcttcct    46620
tcttgtgaag gatatagaca tctagatata gaaagctaaa atatctacta gtagattcaa    46680
taaaaatata agtgttctcc aaggcacatt aaagttacac tgtgaaaggt tgaagacaga    46740
gggagaattt taaaaatagc aagagaaaaa catcaagtca catgttgggg gaaatcccat    46800
cagactagca gcctattact cagtaaaaat cttgcaggcc aggagagcat gagaaactat    46860
attcaaagtg ctgagagaaa aatgccaatg aagaatacta tgcccaggaa agctatcctt    46920
taaaaaggat ggagaaataa catctttttc agacaagtaa aaactgaagg aaattcatca    46980
ctactagatc aaccatacaa taaatgcttc agggagtaca acatctataa gtaaaaggat    47040
gatgtctact atttagaaag cacaagaaag aattaaactc acgggtagag cagatacact    47100
aatgaaagca agaaagaaat caaagcttgt cactacagaa aatgaccaaa ctgtaaagat    47160
aaatattaaa agaggaaaga gaaacaaagg atatacagaa cattcagaaa acagctatca    47220
aaatgacagt agtaagttct cacctattat taacaacatt gaatgtaaat ggtttaaatt    47280
ctacaattat aaagtataga ctggctgaat gggtagaaaa gaaaacacaa aagacccaat    47340
tatatgctgc caacaagaaa ttcacatcat gggtaaagac actatattag tctgtcctca    47400
tgctgctaat aaagacatac ctgagactgg gtaacttata aaggaaagag gttaaatgga    47460
ctcacagttc cacatgtctg gaaggtctc acagtcatgg tgtaaaacaa gggaagaaca    47520
aagggatatc ttacatgagg gctggcaata gaacttgtat aaggaaattc tcatttataa    47580
aaccatgaga tctcatgaga cttattcact atcacaagaa cagcatggga aagacccaca    47640
atcatgagtc aattacctcc tactgggtcc ctcccacaac acatgggaat tatgggagct    47700
acaattcaag atgagatttg ggtgaggaca cagccaaacc atatcagaca caaatagact    47760
gaaagtgaag tgacggaaac catatcccat gcatatgaaa gccaaaactt tgcaggagta    47820
gctatactta tatcggacaa agtagactta aagtcaaaga acataacaag agataaagag    47880
gtctagtatg taatgatgaa gggatcaatt cattaacagg atataacaat tgtaaatata    47940
tatggactca acactggagc actaagatat ataaagcaaa tattattaga gctaaagaga    48000
gagatagact ccaatacagt aagagttgga aatttcagca ccccactttc agcactgggg    48060
agatcatcta gagagaaaat caacaaagaa atattggact taatctgtgc tatagaccaa    48120
gtggacctag caggtatttta cgtaatattt tatccaacag ctacagaata cacattcttt    48180
tcaccagcac atggaacgtt cttcaggata aaccatatgc tagtccacaa aacaagtctc    48240
aaaaaatttt taaaaatcaa aatcatgttg agtaccttcc cagagtacaa tggaataaaa    48300
ctatagatca ataataagag aaattttgga aactgtacaa atacattgaa ataaagcaat    48360
aggcttcaaa gtgatcatta gattaatgaa aaaatgaaga tcaaaatgaa aaaaaatctg    48420
aaacaaatga aaatgtaaac acaacatacc caaacctatg gaatatagta aaagtagtgc    48480
taagagggaa tgtttatagca atagccatct acatcaaaaa agtggaaaga tttcaaataa    48540
acatcctaac agtgcaccac aaggaactag aaaagcaaga gggatccaag cccaaaatta    48600
atacaaagaa ggcaaaaata aagagcagaa aaaaggaaa tagaaactaa aagctaaact    48660
aaactaaata ataaaactat taacaaaaca aaattttatt tcttgaaaag ataaacataa    48720
accacttgga aaataaaata aaaataaaat cctagaaaaa atttaaccaa ggagatgaaa    48780
agataaaaaa taaaccacta gctggactaa ctaataaaga gagaagaccc aaataagtaa    48840
atcagaaaca aataaagcac acattacaac tgataccaca gaaatataaa ggactatcag    48900
agattatttt gagcaactat acactaacaa attggaaaac ctagcggaaa tgaatcaatt    48960
```

```
cctaaataca tctaccctgt caagacagaa ccagaaataa ataggaaaca tgaacagacc    49020
aataacgagt aacaagactg aatcaataat aaaattctcc caaaaaagaa aagcccagga    49080
ccagatggct ttatttctga gttctaccaa acttttaaag caagacaaat gccaattctt    49140
ctcaagctat tcttaaagaa aaaaacgaaa aggagagaat tcttcttaat tcattctaca    49200
aagccagcat taccctgata gcaataccag ataaagagac aaccaaaaag aaaactacaa    49260
gccaatatgc aaagtttctc aacaaaatac taacaaactg aatctaacaa cacatctaaa    49320
aaataatcga acataataaa gtgggattta tcccaaggat gcaaagaagg ttcaacatac    49380
acaaatcaat aaatgtgata catcacttca aaagagtgaa gaacaaaaac catatgatta    49440
tctcaactag cacagaaaaa aagcatttga tataattcaa gaactcttta tgatgaaaac    49500
tcttaacaaa ttggcataga aacaaagtat tgcaactcaa taaaggccat atattattaa    49560
cccacagcta tcatcttaca gaatgaggaa aaactgaaag tctttcttat aataactgaa    49620
taagacaagg atgcccactt ttaccactcc tattcaacat ctcactggaa gccctagcca    49680
gagcaattag gcaagagaaa gaaataaaag atgtccaagt tagaaaagaa gaagtcaatt    49740
gtccctcttt gcagatgaca tgattataca tagaaaaatc taaatactcc accaggaaac    49800
tcttagaact gataaatgaa ttcagtaaag ttgccagata caaaattaac atacgagaat    49860
cagtagcatt tttttatatc ataatgaact agctgaagga gaatcaaga aagcaatctg    49920 atttacaatt tttgccagga aaataaaata aaaataaaaa cctagaaata aatttaacca    49980
aggaggtgaa gacctctaca atgaaaacta caaaacacta atgaaagact gaagagaata    50040
caaacaactg taaagatata atatgcctat ggattggaaa aattaatatt gttaaaatga    50100
ccatactaca caaagcaatc tacaacttta atgcaatccc tatcataata ccaatgacat    50160
ttttcacaga aagagaaaaa acagtcctaa aatttgtatg gaaatacaaa ggacttgaat    50220
agcaaaagca atactgctca aaaagaacaa agctggaggt ctcatactat ataatttcaa    50280
aatatactac aaagctataa ccaaaacaac atagcactgg tataaaaaca gacacataga    50340
ccaagggaat ggaatagaga agccagaaat aaatcaatgt atttacagcc aacttatttt    50400
tggcaaatat gaaagaacat acatgggaaa atgatggtct ctttaataaa tagtgctagg    50460
aaaactggat gttcacaggc agaagaagga aactagaccc ctatctctca ccatatataa    50520
gaatcaactt gaaatggata aaagacttaa acatgaaacc cagaaatata aaaccactag    50580
aagagaatat aggagaaatg cttcagaaca ttttaggga agatattgt ggctgagatt    50640 tcaaagcac aagtagcaaa aacaaaaaga aacaaatgtg actgtattaa actaaaaact    50700
tctacacagc aatggaaata attaacagag tggagagaca acctatagaa tgagacaaaa    50760
tatgtgcaaa ttattcatcc aacaagggat taatttcag aatatataag gaattcatac    50820
agctcaacag caaaacaaaa caacaacaaa aacctgatta aaaagtgagc aaagccttgt    50880
agcatagttt gaagtcaggt agcgtgacgc ctccagcttt gttcttttg cttaggattg    50940 tcttggctat acgggctctt ttttggttct atgtgaaatt taaagtagct ttttctaact    51000
ctgtgaagaa tttcagtgat agcttgttgg gaatagcatt gaatctataa attgctttgg    51060
gcagtatggc cattttcacg acattgattc ttctttccat gagcatgaa tgttttttcca    51120 tttgcttgtg tcctctctta tttccttgag cagtggtttg tagttctcct tcaagaggtc    51180
cttcacatcc cttgtaagtt gtattcctag ttattttatt ctctttgtag caattgtgaa    51240
ttggagtttt ctcatgattt ggctctctat tattggttta tagggatgct tgtgattttt    51300
```

```
gcacattgat tttgtatcct gagactttgc tgaagttgct tatcagctta aggagttttg   51360
gggctgagac gatgaggttt tctaaatata caatcacatc atctgcaaac agagataatt   51420
tcacatcctc tcttcctatt tgaatatcct ttatttcttt ctcttgcctg attgccctgg   51480
ccagaacttc caatactatg ttgaatagga gtggtgagag agggcatcct tgttttgtac   51540
cagttttcaa aggaaatgta accgaacagc atggtaatgg aaccaaaaca aatatataga   51600
ccaattgaac agaaccgagg cctcagaaat agcatcacac atctacagcc atctttgaca   51660
aacctgacaa aaacaggaaa tggggaaagg tttccctatt taataaatgg cgctgggaaa   51720
actggctagc catatgcaga aaactgaaac tggacccctt ccttatgcct tagaacaaaa   51780
attaactcaa gatggattaa agacttaaac atacgaccta aaaccataaa accctagaa    51840 gaaaacctag gcaataccat tcacgacata ggcatgggaa gacttcatga ctaaaacacc   51900
aaaagcaatg gcaacaaagg cccaaattga caaatggtat ctatttaaac taaagagctt   51960
ctgcacagca aaagaaacta taatcagagt gaacaggtta cctacagaat gggagaaaat   52020
gtttgcaatt tatccacctg acaaagacct aatatccaga atctacaagg aacttaaaca   52080
aatttataag aaaaaaataa acaaacccat caaaaagtgg gcaaaggata tgaacagaca   52140
cttttcaaat ttatgcggcc aacaaacata tcaaaaaaag ttcatcatca ctggtcatta   52200
gagaaatgca aatcaaaacc acaaagagat atcatctcac accagttaga atggcgatca   52260
ttaaaaagtc aggaaacaac agatgctgga gaggatgtgg agaaatagga acgttttgc    52320 actgtttgta ggagtgtaaa ttagttcaac cattgtggaa gacagtgtgg tgattcctca   52380
aggatctaga actataaata ccatttgacc caccaatccc atatacccag aggattttaa   52440
atcattctac tataaagaca cattcacata tatgtttatt gcagctattc acaatagcaa   52500
agacttggaa ccaacccaaa tgcccatcaa tgttagactg gataaagaaa acgtggcaca   52560
tatacaccat ggaatactat acagccataa aaaataatga gttcatgtcc tttgcaggga   52620
catggatgaa gcaggaaacc atcattctca gcaaactaac acaggaacag aaaaccaaag   52680
accgcacgtt ctcactccta agtgggagtt gaacaatgag aacatattgg cacagggagg   52740
ggaacatcac acattgggc ctgtcgcagg gtggggaca aggggagaga tagcattaag     52800
agagatacct aatgtagatg acggggttgac gggtgcaaca aaccaccatg gcacatgtat   52860
acctatgtta caagcctgca cgttctgtat cccagaactt caagtataat aataaaacaa   52920
aagtgagcaa aggatgtgaa tagacatttta tgaaactaaa acatacaaat ggccaataag   52980
tatgagaaaa aatgctcaag atcactaatc actggaaaaa aatgcaaatc aataccacaa   53040
tgagctatca cacctgtcag aatggctatt atcaaaaaga caaagataa gtgttgatga    53100 ggatgtggag aaaaggaaac cattggaatt gttggtggga atgtgaatta gtacagccat   53160
tattgaaaac agtatgaagt ttcctcacaa aattaaaaat ggaactagca tgtgctcctg   53220
caatctcact accaagcagt tatccaaagg aaaggaaatc agtctattaa agggacacct   53280
gtaacttaat gtttattgca gcagtattca caatggctaa gacatggaat taacttaggt   53340
gtccatcaac aaacaaatgg atgaagaaaa tgtagtatat atacactcaa tgaaataacc   53400
ttcaggtata aaaaaagtat gaaatcctgt cactcacagc aacacagatg agcctggagg   53460
actttatatt aagccaaatc ggtcagtcac agaaagataa acaccacatg ctgtcattta   53520
tatgtgggag ctaaaacata attgagttca tggaagtaga gaataaaatt gtgggtatta   53580
aaggcacaaa agggtaggag ggaggggacg atagggagaa gttggttaac agatgcaaaa   53640
ttataactag ataggaggaa ttagccctgg cattctgcag cactgcaggg tgaacatagt   53700
```

```
ttaccataat ttattgtata tgctcagaaa gctagaatag aggatttgga ttgttcataa    53760
cagaaagaaa tgatgaatgt tagaggggat ggatatgcta attaccctga tttgatcatt    53820
acacattgta tatcacatat ggaaatatat cactgtgtca tccataaata tgtacgacta    53880
ttgtgtcaac taaaaataaa aggaaaaaaa gtaaaaataa gggaaagtat ttattttacc    53940
ttcacttatt ctctgatgtt gttccttcct ttatttagat ccatgtttct aacttatgta    54000
attttccttc ttcctgaata gcttctgcta agatttcttg caaggcaggt ttacttgtaa    54060
caaattctct caattttttgt ttgtctgaga aaggctttat tcctccttca cttttgaagg    54120
ctaaattcac agagtacata atttaaacac tggttttta ctcttaacat tttgaatatt    54180
tcattcctct ctcttttttgc ttgcatgatt tctgtggtga atttggatgt aattcttatc    54240
tttgctcttc tataagtaag ttgtttcttt tctccacttt gcattctttt ctagatattt    54300
tcttcatccc ttgattttttc ttttttctgtc tcttctcctt ttttatattc ccattacatg    54360
tatgctactc cttttgtagt tgtcccacag ttcttagata ttctgttctt ttttatcagt    54420
tttttttttt ttgaattttt gcttctcagt tttggaagtt tctgttgtcc tatcattaga    54480
ctccaagatt ctttcctcag ctatgtgaag tctactaatg agcccatcaa aggcatattt    54540
tctttctgtt tttgatcttt atcattttaa aattatttcc tagaattta atctctctgc    54600 ttaaatttcc tatctgttct tgtctgttgt ctaattttttt cattacagct ctgacagctc    54660
tgagcatatt aatcatagac tttatttatt ttctttttt gagacggagt ctcgctctgt    54720
tgcccaggct ggagtgcagt ggcacgatct cggctcacag aaacctccac ctctcaggtt    54780
cacgccattc tcctgcctca gcctcctgag tagctgggac tacaggtgcc cgccaccatg    54840
tccagctaat ttttttggtat ttttagtaga cacggggttt caccgtgtta gccaggatgg    54900
tctcgatctc ctgacctcgt gatctgcctg ccttggcctc tcaaagtgct gggattacag    54960
gcgtgagcca ccacgcctgg cctcaatcat agacttttaa aaagatttct gttctgataa    55020
ttccaacctc atggccatag gtaagtctag tccttatgct tgctctggct cttcaaactg    55080
tgtgttttgc cttctagtat gccttgtaat tttttttttc atagctgatt ataatgttct    55140
gagtaaaaga aactgtgata aacaggcctt tagtgatgtc acaatacggt gtggaaaaag    55200
gggatgtgtt ctataagcct gtgattaggt cttagtcttt tggcgagcct gtgacctgga    55260
ctgtgaactt tcagtgctgc tcttttttt cccctcctta ggtggtacag ggcagccttc    55320
caacatgtga aaaactagag gacccttgag ctgggtattt ttttccccag gcagatcaga    55380
ctctgataaa acctcagaag gttaggctct ggtaaaatag tcacccttga gtttaggccc    55440
tttaaaggag aacagactat tcagcttttt agaaattagt atttttttt tgagacaggg    55500 tcttactgtc acccaggctg gagtgcagtg atataaatca tggctcactg cagccttgac    55560
ctcctgggtt caagtgatgc tcctatttca acctgagtag ctgggaccac cagcatgtgc    55620
caccatgcat ggctaatttt tttgtaattg tttgtaaaga taggatctca ctatgttgtc    55680
caggctggtc tcaaacttct gggctcaagt gatcctccca cctctggctt attttataat    55740
agttttttcc cctcctccta ccagaagcac aagaggactt tctcatctga tacttactgt    55800
gaggacctag tagttagagc tcctaaagat caaactcata aaagtatata gcccccacaa    55860
ctatgactgg gtacccttgg agttttttaat tctctaagtt gtttcacact gagccttcag    55920
caatttgcca attacagttt aatttttttct acccccacaa tggttgctat ggaggtttct    55980
gctcatggat ctctgcttca gtaagttgtg gttctatctg tttctctaat ttggggatcc    56040
```

```
tctctttctc tccaactttta gggcagtggt ttgccctgtg acctcacttc tctgatctaa   56100
gaagagttgt tgattttttt ttaatgggtt tagcttttta cttttaagta tggattggca   56160
acttctaagc ttcttatatg ccaaatggaa aagtagaagt tctcaaaaca actattttat   56220 actaatatt tattgattta tatagtatta agtattataa ttaaatgcta agtataactt   56280
agtgttaagg aattgactta gtcaataagc aactgaaatg gtgggagaaa atatacacga   56340
gtacataaga aactaaacta ctagtttgga gtcttcattg ttctctgggc attagtgaat   56400
atgttttgac agaaggaata gaaactattg atcatccaga aagtcagtta aatgacagtt   56460
aaacttctgg tagataagtg tgttcaagtg tctacatatg cattcacatt taaatatagg   56520
cttctacata gtacctttt ctcttaatgt tttattatag atttaccact tgtttatgaa   56580
cattacctga aaacaaatat atctgcttaa tattttattt tattttccat catctatttt   56640
accattccat tattagcttt cttttctatt ttagctgttt tctttatgta gataaatttt   56700
gaacaagact caatttactt gacctttaa ttggcattta ctatggacca ccacttcctc   56760
aaaacaatcc attctcttgg ctttccttct aactctctgg ctttactatt tgtctatttg   56820
acatctgttc ctgaatcttt gaaagtcagc tcaaacgtca tctgtttaaa acctaacaca   56880
taatttatac actccacctc ttcttctatt tcctatctca atggcaacac aatactgatg   56940
gtaaccagct taccatagtt aggcttataa ttttgaatt tacaatgggc ttattggaat   57000
gtaaacccat tgtaagttaa ggagcatctg actcttttgt tgtactcacc agacaactca   57060
agaatgatcc ttgatatgtc catcttgctt aattttatt ttcaaatcac attaaatttg   57120
cttatttctc aaatctattc atgtatttct agattctctc ttactatcaa gtgcaataaa   57180
taattatgtt aagcactgac tatgtaatag cctcataaag attcacccat atactttctt   57240
gaatctctcc aaaccatctg gcatatggct gttaatatga ccattgaaaa aagtaaaacta   57300 gaaaaactgt tcccatgttt gtaagtacaa atacattaat tattgctttt aggattgata   57360
caaaacttct taaaatatcc ttaaggccac acataatttg gtctcttcca gctctggctt   57420
tatgtcaaac cagttctgtc tcttcctctc tcagccatat tcctactttc ccttgctctc   57480
ttctttctag ccacatacag gccatgatcc ctctctcttc aaagtagtca cctatactat   57540
ttgctactga atccccttt tccctaaggt acttatgatt gagatctctt gtgaagtatc   57600
cttctccggg aagtattcat tgaggtttt aagtaaaatc ttcttgtata ggcttcatgg   57660
cagcatatat cttgtattca taacagttct caagttggga attgattgct gttattggat   57720
taatgttttt gccaccaaat aataaacttc ttgagggaag gagccacgta tgattttgat   57780
ccctgttgta ttcctaatac taaatggcac atggtaaatg ctcaaatatt tgatcaaaga   57840
ataaatgact ttaatttaaa ctaagaatta actaataagt catactataa tctgctaagc   57900
tacctgacaa atggtaaaaa ttgtagcaat tgagatagaa ttccaggaac aatatacacc   57960
tttttcaaat ttcatacaga gtagattttc taaaaaataa gcagcgcatt ttaaaaggcc   58020
ccctaaataa ggcttcagat ggcacaaggc catggatagg ttgtcatagt gatgatcaga   58080
aatgaaaaat atttctactt tacttgaggt aaggagtttg aggacagcct ggccaacatg   58140
gtgaaaccca gtgtctacta aaaatataaa cattagctgg ctttggtggt gcatgcctgg   58200
aatccagtta cttaggaagc tgaggcagga gaattgcttg aacccaggag gcagaggttg   58260
cagtgagccg agaccatgcc actgcactcc agcctgggca acagacccca tctcaaaaaa   58320 aaaaaaaaa aaaagcaat gaagtatatt tctatagggg ccaactttat ttatagcaag   58380
agacatgaga ctgaatatat tctatgccaa aactttccaa tccttagaat cagccctaca   58440
```

```
aaaagaaaga aaaaagaaca gaaaggaagc agcaatcagc tatgagcaat aattagacat    58500
tcgtttgcta gctctagcac atgtgaccat gaagagtaac tgtgaaccat attgactttc    58560
tctcctgaaa agaaaaatat gaaaaaaatt cagaagaaaa ctgtcctatc acaaagaata    58620
cagaaattgg gtaagaatga acagctgttt catttcatta cctttgccct tttccacctt    58680 tattttttgga caattagttg atctaaaaag caatagttct ctatcagtca gttttttgcta   58740 caaacacata cacacacaga aagagagaaa ggcatacagt aatatgcatt taccttaggt    58800
tcacaggtat gcagtttggc tgagttcgat tacctccatg tgtttcattc taagtcataa    58860
gatggaagga gcagctgtat gggagtttta acatatgcac aaagatactc caccttacaa    58920
gaggtacagc ttaaattccc tcctcttgag tgtggattag aattagtgac tcactgcaag    58980
caactgaata atgaggaaat ggcagtgtgt gacttccatg taataaaaga catggcttcc    59040 tccttgctt tctcttacatt gatacttggg ggaaagtcag caactatctt ggaaggatat    59100
tgaagaaagc ctgtggagaa actcatgtgg tgagaaattg aggcattctg ccaatacctg    59160
catgaatagg tcatcttggg aatagatcct ctaatcctga tggagtccag atgactacag    59220
acatgaccaa catcttgact gcctcctcat gaaagatgaa ctagaagctc ccggttaggc    59280
agcttccaaa ttcttgatcc acagaaactg tactgaaagc atcaatttct taccacatgt    59340
cttttggaca aactcaacat taatggacag aggagcatac ttctctatag taggctaaat    59400
aatggccacc cagataaaaa aattctaatc tgaaaatgta taaggtaaag gaatctacag    59460
atgtgattga attaagaatg ttggtgtgat aagtttattt tggattatct tggtgggccc    59520
taaatgctat cacaagttcc ttctaagaga aaagcaggag aagacttgac acccacacaa    59580
agaaggtgat gtgaagatgg aggcagagac tggagccact aggccacaag ccaaggaaca    59640
ctaaggaatg ctggcagaca ccagaagata gaagaggcaa acaatgcatg ctctcccaga    59700
gcctctagaa atgtgagata taagttttt attgttttga gcctccaaat ttttggtaat     59760
ttgttacatc agccatatgg aatgaaaaca tcctctcatt tgttgagttt agatgttaaa    59820
tactggctga acaataatct actctacttt agcatctttt caaaaataat cacaaaattt    59880
aaaaggaaaa ttatgcactg gtactagcaa aataaatgaa caaatgaatt aacacaaaat    59940
aggcaaaagg aaaatgaagt atctagacca aagtttaatt atccatgaaa gcaatggaaa    60000
atgtgaagtc tctaagaaac caatgtaaaa agagctaaaa acaatatagt atgaaagaaa    60060
ccagaaagaa acaaatgttc tttggatttt ggagaaatac agagactaaa ataaaaacca    60120
gaaatgaata ctccattaaa acaggcatat gaaagacagg atgggtaaaa accacacaaa    60180
acgaaattgt gtgtttgtgt atatatacgt gtgtacacac atacacgaaa agaaaaagtt    60240
caatagaaga ttcattttt atgtaattag tgtttctaaa gaagatactt aaaatgtaat     60300
ttaaaaattc aaagatagaa gaaaactatg ctgaaattaa agaagatata attctacaaa    60360
tgtaaagaac attatgtatt ttaagaactt gaaagaaaag gagtgggga gtggccaaga    60420 tggccaacta gaagcagctc gtgtgagtgg ctctcacaaa gagggacaaa agggcgagta    60480
aatacagcac cttccactga aacatccaag tactcgcact gggactaatc aaggaaacaa    60540
cttgacccat ggagaacata gaaaacaaag gcaggacgac agcccacctg gcacgacac     60600 ccagccaggt gaacctcccc tgcccagaga atcggtgagt gaatgtgtga ccctggaaac    60660
cacactcttc ccacgaatct ttgcaacctc gagttgggag atcccctctt gaacccactc    60720
catcagggct ttcagtctaa tacacagaga tacgggagtc ttggcagaga agctgctcag    60780
```

```
gcacatgttg gagaaccagg aactgtagat attccacctt caggcttccc ggcaaaagta    60840
actgcaactc cagaaaagca ggagattaga tccttgtgca tacccttagg aaagaggctg    60900
aatccagtgg gccaagcagc gatggtctgt aggccctact tccatggtgc ctcaaaggat    60960
aagacacatt ggcttggaat tccagccagc caccagcagc agtgttgtgc ctacctggga    61020
cagagttccc agggagaggg gaaggccacc atcttcactg tttgggcaag tcaccttttt    61080
cagcctgcag actttgaaga gtccaaaccg atcgggcaga agggatcccc caacacagca    61140
caattgctct accaacacgt ggccagactg cttctttaag caggtccctg agccatccct    61200
ccttattggg caggacctcc caaccagggc ctccagccat ccccgctggt gttctctggc    61260
ctacagagat ttgaaaactc cctgggacag aggtctcaga gggaggggtg ggctgacatc    61320
tctgctattt gggtactgaa cctgtccagc ctgtgggctt tggagagccc aagccaacag    61380
gcggtgaagc gttaccccag cactgcgcag ctgctctaca aaagcatggc cagactgctt    61440
ctataagtgg gtccccaatc ctcttcctcc tgactgggca agacctccca accaggatct    61500
ccagccacct cctgcaggtg cgttccacct ggcaacaggt tcatacctcc ctgggccaga    61560
gctcttagaa gaagtggcag gctgccatct ttgctgtttt gcagccttca ctggtgatac    61620
cttcagctac cggaaaatcc aaggcaacta gggactggag tagaccccca gcaaaccaca    61680
gcagccctat ggaaaattgg ccaaattgtg ccaggggaa aaaaaaggt aggcaacgtc    61740 gaacattgaa ggtagattag ataagctcac agaaatgaga aagaatcaga gcaagaatgc    61800
tgaaacctca aaaagcctga gtgccctctt tcctccagct gacctcatta cctctccagc    61860
aagggttcaa aatagccagt atagagaagt acttaatcct cctgataggg ctgaaaaaca    61920
cactacaaga atttcgtaat gcaatcacaa gtattaatag tagaatagac caaacagagg    61980
aaagaatttc agagcttaat gaaatatggc aggcagacaa atgtagagaa aaagaatga    62040 aaggaatga acaaaacctc cgagaaatat ggaataccat atcacaccag tcagaatggc    62100
tataattaaa aagtcaaaaa ataacatgct ggcaaggttg tgaagaaaaa ggaatgctta    62160
tacactgttg gtgggaatgt aaatcagttc agccattgtg gaagatggta tggcaatttc    62220
tcaaagacct aaagacagat atactattca acccagcagt cccattactg gcatataac    62280 caagggaata taaatcattc tgttataaag acacatgcac atgtatgttc attgcagcac    62340
tattcacaat ggcaaagaca tggaatcaaa ctaaatggcc atcaataatg gactggataa    62400
agaaaatgtg gtacgtatac accatggaac actatgcagc cacaaaaaag aatgagatca    62460
atgagatcat gtccttttgca gggacatgga tggagctgga ggccattatc cttagcaaac    62520
taatgcagga acagaaaacc aaataccaca tgttctcact tataagtggc agctaaatga    62580
tcagaacaca tggacacata cagggggaaca atacacactg gggctttttg gaggatggag    62640
ggtaggaaga gggagaggat caaaaaacaa ttaatggata ctaggcttaa tacctgggtg    62700
atgaaataat ctatacaaaa aaacccatg acacaagttt acctatgtaa caaacctgca    62760
cttgtacccc tggacttaaa ataaatgttt aaaaaataga gaaagaaaaa gacactaaaa    62820
acatgaaaag atatgaaagc atataactca ctgtaaagat aaagcataaa attcaccata    62880
aagataaaat atagtcaaat tcagagggct gtaatgaatt tgtatgtaat taagtgtata    62940
ctgtaattat agtttataag ttactttcc tctactataa gagttaaaag acaaaagtat    63000
taaaaaataa cttcacctaa aaaaagaac ttagccaatg tcatgtttta tactagaaaa    63060
tactgcagtt cagtcttata atcctggctt ttctcttctg attttccata tttataaaat    63120
atttgaagaa atttgtttct tatgtacatc ttgacatatg tgatatatga tttgtttctt    63180
```

```
tttattttttt attttttttct gagacagagt cttgctctgt tgcccaggct ggagtgcagt    63240
ggcgtgatct cagctcactg caagctccgc ctcccaggtt caagcgattc tcctgcctca    63300
gcctcccaag cagctgagat tacaggcatg tgccaccaca cccggctaat tttttttttt    63360 tttttttgtat tttagtaga gatggggttt caccatgttg gccaggctgg tctcgaacta    63420
ctgacctcac gatctaccca ctttggcctc ccaaagggct gggattacag gcataaggca    63480
ccatgcctag ctgtgatttg tttcttattt gcatctggac atatgtgaca tgtgaataag    63540
aaacaattat tgggactttg gtcaagtaat tctattcttt gttaaatcaa aagatggcca    63600
tctaagtttc ttttcaacac catgtatcta taattcttac tctgagccat tcttctgata    63660
gggcatgaat gaaagaatt ttagaaagca acagtaattg gcaatcatat agatctatat    63720
tagatgcatt aataaaatgt actaaggtcg atgaattaat aactgtgacc tctataggag    63780 tcaaccttt aagggtatag taacacattt acattccata tcaagcatta ggtaaaaaat    63840
aatcaactgg tataacatta tctttctgtg gatctgccaa aaataagttt tattaataac    63900
ctagaacagc cacctaacca atatggcttt ttaaatattc atgtgtcatg caatttgcta    63960
acatgttgca agaaattggc attcattatg tgacatattg tctcatacga tatttttggt    64020
gaattggaag ataacatata gagtagctac acgtttcacc ttcttttttg aaggatgaca    64080
tggtaaaaat taaatactct atgttttatc aaagaaaaaa ttatgtatga gttattgtcc    64140
ttggggtatg gggaagtcaa catgaaaatg acttaatagg caaatattaa ttatccacta    64200
aattttcagg aatatgtaca atggcaatgt gaagatagtt attgaaaatg tatcttttac    64260
acttgagatg tatgtattca gacacttctt gcagataaag ctgatagtat atacatttta    64320
aaatcagggt aaacccagac atcatcatgc ttttcacagg tgataagagt aatgaatact    64380
tttctgagag gcagatgagg attcaaagcc catgactaaa tcctgccatt gctccacttc    64440
ttatcctgtt tctctggaga cattacatag gctaagattg ctttcagtcc cagaagctct    64500
gatagcatgg agttgctagt ttgctggaca gagctagtcc aacccggtgc ataagaaaat    64560
ctgaaacctt aggaggtttt tcctaatatc aactaaatta ttgatttaga taatctctac    64620
cttcttctac tacattcctt gtaaatgaaa aaaaaatag cgcacatatc agtctgcttt    64680
ctcactccta tgtttataat acacacatat aattacactg tctcaggaaa attctacctc    64740
aaccatccca gaaaattgga ttgctaaaaa tgttgtgaac aaatttcaac cttaattctc    64800
actgtcaatt tcaaagtact aatgcagatg gttttatatt ccttgcacat ccaattaatt    64860
agttgtgact gttgaaaata ctatgttgat tataagcctg tagtctcagc tcaactgaaa    64920
agagtgtaaa acagacaact gatatgaagg ggtaaagggt ttaggtatgt tatacatttg    64980
tgattctttc tcttatgtgt tgagctttgt atggatccct tcattctaat ataaattcct    65040
tttcttgtta tttgttgatg gcaggaaatt tgactgaata acctcttaag ttcatctcaa    65100
cttaatgact tcacatttta taatactttg tctataaagc ataacttcta aaataggtac    65160
ttctatttcc ctagatgagc cagattctct tagagaattc tgggattcaa ttatgggatc    65220
tgggaggggc tctaaatatg ggaggatttg tgtatacact tatttatcct tcaactatag    65280
aaaatgattc ctcatgctta gtcagctgag ccaggcaaaa cttatttttcc ttaaaatgca    65340 catataaata tcagatatta taagattatt attttttata attacaagat attagaaaag    65400
tactcagttt taaccatatt atttttatgtt atttattaca ggacagcatg aaagaaattg    65460
gtagcaattg cctgaataat gaatttaact tttttaaaag acatatctgt gatgctaata    65520
```

```
aggtaatgat aattatttgg agtttgtcat tcaagcttga ttttatagaa gcttctattt   65580
tttgtgcctc tgttagacaa ttatatgaat actattaata tttgcagcct gatcacataa   65640
ttcccattga ttaaatcata ctatggccca attttatatt tttgttttac aaatagtcct   65700
gtgcttatta aataacaagt ttttttttgtt tcaccattct attttttacc ttgaaaatac   65760
tagaattgtc gaattcaaag acacacctat ctcttatttt cttttcttct ttctttcttt   65820
gttttttttt ttggaggcag agtttcgctc tgtcaccagg ctggagtgta gtggcgcaat   65880
ctcagctcac tgcaaactcc gcctcctggt tcaagcgat tctcctgcct cagtctcccg   65940
agtaactggg tctacaggca tgcaccacca cacccaacta attttttgtat ttttagtgga   66000 gacggggttt caccatgctg gccaggatga tctcgatctc ctgacctcat gatccgcctg   66060
cctccgcctc ccaaagtgct gggattacag gcgtgagcca cggtgcctgg cctctaaatt   66120
tcttatacag aaaaatactt gttaatgtga atgcttgcac acatcaaat ataagtcatt   66180 ggtataattt agttggaagc gtcttgaaaa ttttctttc aatatttgct tatctctaaa   66240
tgattaccac atctagttgg tataatatta cactttaaaa aacctaaaaa gtttatatca   66300
tttctcccta cagaaacaag tgtgctattt catagtcttt taaaaactca cagtagctaa   66360
gttagcctca tggcatctca caaccataaa ttcttttttt taaatttctt aatttaaata   66420
tctgcaaaac ttatgtttta ggtgactaca gtcctttatt ttcttattat cagctattct   66480
tccatagctc aaaagatgca agaaatacta agaaaaaacc acacatacct cttataatac   66540
attgttgctt ccagaagtct tctccttcgg ttatcatgtt taaaattgaa taatcttcta   66600
atatgttcac acataagcga taagatcaca taagcataat agagaaaaca aactttaaaa   66660
gtcaagataa ttattaaacc aagttctaag aacttcatgc tgtcacctag gagccaaaca   66720
gttttagttc tgttacttgt caatcacatg attaactgga atagaaagct ggggtggagg   66780
cggggcatta cctagcaaca tagctcaagc tctaggctcc ttaagaaagc ttataatttc   66840
ttaatatttt atttgaacca tggcccttct gacttttttcc tataatagga aggtatgttt   66900
ttattccgtg ctgctcgcaa gttgaggcaa tttcttaaaa tgaatagcac tggtgatttt   66960
gatctccact tattaaaagt ttcagaaggc acaacaatac tgttgaactg cactggccag   67020
gtaagctaag gactatttac tttgaataaa aatattaaat actcctgtgc caagatacca   67080
ctattctctg atgatcacat ccattatcat agaatcctaa gtgttatta tcatctaaag   67140 ttgaagtatg tttactcaat cctagaagag gaaaggctca gtttggaaat acctatttat   67200
ctcttggcta gagtgaattg tttgtgaaag gggagtaaaa aataaataaa taaattcttc   67260
attgccataa taacttccaa ggatactagg gtgatatatt gggtggggaa tggtaaattt   67320
ctatatctaa aacttattaa tagctttaat ccatatatgt acacatttac aagaactcct   67380
agtcaataaa acaggaaatc aaatgtattt aacaaatatc tttataggct taaactagac   67440
ataaacatgt ccaacaattt tcccttcttt aaataatttt gatacaaata gggctaatat   67500
tttcctactt ttctactagt ggttatgaac taaaacaaca aaaccaaata tggaagacat   67560
catctagaga ctagacagca gtttccttat ctacaaaatg cagaaaaaca tatctacatt   67620
gtgggatttg aaaggattaa atggcataac acatgtaaag tgcttagtac taaaaagttt   67680
tcaatattta atacagtgct ttattttatt tgtattattt acctctttttt ggattttacc   67740 agctgccaca caaaaccaaa agtttatttt atggttttaa atattttctt aaataacatt   67800
tttatgactt aaaaaagaat tttgttttgt ttgagcacta gtagtttccc atagaaggta   67860
aaatggtaag attatctttg aatcctattg acagtgataa aaatgtagat tatctattat   67920
```

```
ataacttgga tagcctcatt tatcattgct ttatgtactt gatggaagca agtctcctct   67980
tagtgtgctg gatttgccaa acttatttcc aaacttgcgt ccttacgttt gtcccctaga   68040
gagcatttct actttttttt tctataaatt ggatctattt tgttctatgc cttcaaggct   68100
cggctcaaga ttcatgaaga cttcctactc tagtctacca tttcttcatt cctacttaac   68160
agcggtttca aagtactgtc taatgcagat aggttttatg ttgcttgcac atccaattaa   68220
ttagttgtga ctgttgaaaa tactgtgttg attataagcc tccactcttg gttcaactga   68280
aaagagtgta aaacggaaaa ctgatatcac ctcttggtct actaagaggt aaaggtctta   68340
ggtatgttat atatttgtga ttcttttctct tatgtattga gctttatatg gatcatcatg   68400
ttccaaaatt aactgtagag aaagaaaata tgcaaataat ttaaatcttt gaattaaat    68460 tatattacat tgattaactt gatacaagtc acctttttct tgaaataaca aggcaagatg   68520
ttaaagcagt cagctacact gaattttctt catgagccag gcacgctaca agctttttac   68580
tattgtttta tttcattttg tttctgataa gtgaagctta ataaaatgta tggccaggat   68640
ttaacaattt cttgttaact ttattttat attgattaaa attcaagttt tatctctgct    68700
actataccct actatgttaa ttttcatac ctcacagtag ttaacacagt actaggcaga    68760
cctacaaaat tatggattct gggtattcag aagactgaac tatcttgctt cttcctttac   68820
cctgatattc catttctaaa tcatattaat attttacttt cttaacaata agaaatttaa   68880
agtagagtct caaatagatt agatgagctg aaggcaatat gaaaattagc aattacaaac   68940
aactggagga gcaatgaaga aatattcaat attataaatg tgactttgtt tttaaggtta   69000
aaggaagaaa accagctgcc ctgggtgaag cccaaccaac aaagagtttg gtgagaataa   69060
ttgtataatt ttccttatgg ttcatcaggt ttttactcaa cttaattcct aattttcat    69120 tttgaattgt ttccttctta tagctggttt tgaaataatt tattataaca ttgataaaag   69180
gagaagcgag gtgcccctca aaaatttgat tcctttaaat tgcattttta aacccactat   69240
tttaaaatag aagctgttag ggcaaataca aaagcatgat ttttttttt tttagaagaa    69300 gcagcattaa aatattgcag ctagcacgta aagaaatga acaaataatt tatataggag    69360
aaaataaact agatgacaaa tacatgaaga aaaaaagcca tccctgttag tttgtaaaga   69420
aataaaaatt aaacaataag gacttatctt atatataccct cttttattag tgtagattgt   69480
acagtataaa taatatataa tagtatataa acatatattt atacatatac tactagacat   69540
tattagataa attatacaat aatatggaaa atatttatga atgacttaat aaggcagaat   69600
acttaaatgg atctgactaa actttaaaat gatataggta ctaattaagt tgaggcatgg   69660
aaaaatgagc acacctggtt cataaaagtg atggattctt cttttatatt tccattattt    69720
gaccaatagc tacatggcaa catggaaatt ccttactctt ttcagaaaag caaagtgagc   69780
ctgtacactc tgagatttag gaaattctag ggattctatg caaagtggaa catctgaagt   69840
gaatacagaa gctaaaagca atataatcac cctgaaggct tttcactaag agaatttgga   69900
aagtttagaa aagaaaggtt gggtgcggtg gctcacgcct gtaatcccag cactttgggg   69960
gtccgaggtg ggcggatcac aaggtggaaa gatcaagacc atcctggcca acatggtgaa   70020
accccgtctc tactaaaaat acaaaaatta gctgggcgtg gtgcacgcct gtagtcccag   70080
ctactcagga ggctgaggca ggagaatcac ttgaacccag gaggtggagg ttgcagtgag   70140
ccgagatcgc gccactacac tctagcctgg gcaacagagt gggactccgt ctcaaaacaa   70200 aaacaaaaa acagagcaaa aaaaaaaaa caaaaaaaaa aaaaaagaa aagaaaagat     70260
```

```
aactatttttc ccaggatgca ggggtaaaac caagattctc tgttttttac tttttagtga    70320
atgcttattc tcggtgtgca aggaaaagta tgaaattttc acatctgtat atttcaaatc    70380
tgcttaggca aatcaacttc aacttgtact taaaaaaatt gtccaggacc ccctattgaa    70440
aacaatatga aaagtttgcc tttatatttc cctttgagat ctgttgttta atctttgaaa    70500
tgtattcttt aaaagtatg tgctagtgtt actaaataca tgacaaaaag agatctgaat    70560
ttgtggccaa attaaaaata ggacagagga gctcaagatt cagtcattat atttacttga    70620
catatattta tttacttgac cttagcagct tatttatctt ctttgcggat cagtttcttc    70680
atctgtgaaa tgagttcaaa tcatcaagtt catatgatga ttaagcaaat aaaatgaagt    70740
aaattatgtt aaacactgag cacaatatat gactgagaga atacccaata acttgttatc    70800
taaattatct agttacccaa taactagtta taatagtttt tatattgctt gcacatccat    70860
ttacttgcta gtgattgttg aaaacactat gttgattta accctgaagt ctgggctcaa    70920
ctgtgaagag tgtaaaacaa acaactgata tcacctcctg gtctaggaag gggtaaaagt    70980
cactggtatg ctttatattt gtgatcaact agttgttatc taagtgaaga attactctac    71040
cctgcactat tcccattctc acaggtcaga ggactcagag aaatataact gagtctatac    71100
agagttactc ctttatatgt ctgttcatgc caagtatctc tttcttccta caggttgtac    71160
aggtagccct ttttaagatt cttgtcaggt gctaaaacct agcttatgag gcaggcatct    71220
gacatactct ggtgaaggtt agttgttgga ggagaccta gggtacaagt tccatcagct    71280
atatccttat tatctttggc aaaataatct gagtattttc aatgttgatt attcttccca    71340
ctaaaaatac atttttctac attaaagaaa ctcaactgag taacctacaa ttacctttct    71400
catgaaattc caaacagtgt tattatgtcc actgttaaac tgtgaaaatg gcggtcagct    71460
gatatagctc tttggagaat cctaagtctt taatcacacc aaccttgaat tttctacatg    71520
tcagttatca caaagatagt tagaaatcat cgtctttaaa atgtcacaca ggattctacc    71580
ttttcattgc accagttttt cagtataaag taatatgatg aaaaatagta ttttaaaata    71640 tatattttg taaaaatgtg aagtttaaac ttttaaaact ctattctcta ggaagaaaat    71700
aaatctttaa aggaacagaa aaaactgaat gacttgtgtt tcctaaagag actattacaa    71760
gagataaaaa cttgttggaa taaaattttg atgggcacta agaacactg aaaaatatgg    71820 agtggcaata tagaaacacg aactttagct gcatcctcca agaatctatc tgcttatgca    71880
gtttttcaga gtgaatgct tcctagaagt tactgaatgc accatggtca aaacggatta    71940
gggcatttga gaaatgcata ttgtattact agaagatgaa tacaaacaat ggaaactgaa    72000
tgctccagtc aacaaactat ttcttatata tgtgaacatt tatcaatcag tataattctg    72060
tactgatttt tgtaagacaa tccatgtaag gtatcagttg caataatact tctcaaacct    72120
gtttaaatat ttcaagacat taaatctatg aagtatataa tggtttcaaa gattcaaaat    72180
tgacattgct ttactgtcaa ataattttta tggctcacta tgaatctatt atactgtatt    72240
aagagtgaaa attgtcttct tctgtgctgg agatgtttta gagttaacaa tgatatatgg    72300
ataatgccgg tgagaataag agagtcataa accttaagta agcaacagca taacaaggtc    72360
caagatacct aaaagagatt tcaagagatt taattaatca tgaatgtgta acacagtgcc    72420
```

```
ttcaataaat ggtatagcaa atgttttgac atgaaaaaag gacaatttca aaaaaataaa    72480
ataaaataaa aataaattca cctagtctaa ggatgctaaa ccttagtact gagttacatt    72540
gtcatttata tagattataa cttgtctaaa taagtttgca atttgggaga tatattttta    72600
agataataat atatgtttac cttttaatta atgaaatatc tgtatttaat tttgacacta    72660
tatctgtata taaaatattt tcatacagca ttacaaattg cttactttgg aatacatttc    72720
tcctttgata aaataaatga gctatgtatt aa                                  72752

<210> SEQ ID NO 4
<211> LENGTH: 78
<212> TYPE: DNA
<213> ORGANISM: Unknown
<220> FEATURE:
<223> OTHER INFORMATION: Mammal

<400> SEQUENCE: 4
tgcaagcacc aaaaaggtga ccacacttca cattggcgat cgcgggtttc tatctgagga    60
tgtgaattta tttacaga                                                  78

<210> SEQ ID NO 5
<211> LENGTH: 152
<212> TYPE: DNA
<213> ORGANISM: Unknown
<220> FEATURE:
<223> OTHER INFORMATION: Mammal

<400> SEQUENCE: 5
gttatgtgct gatgggcttt atttgatcta cagaagatgc tctggtgaca ccctcagtgt    60
gtgttggtaa caccttcctg cctcgagata acttcgtata atgtatgcta tacgaagtta    120
tatgcatggc ctccgcgccg ggttttggcg cc                                  152

<210> SEQ ID NO 6
<211> LENGTH: 153
<212> TYPE: DNA
<213> ORGANISM: Unknown
<220> FEATURE:
<223> OTHER INFORMATION: Mammal

<400> SEQUENCE: 6
gtatgctata cgaagttatg ctagtaacta taacggtcct aaggtagcga gctagcccaa    60
ttgcgtactt tggatagtgt ctcttttaa cctaaatgac ctttattaac actgtcaggt     120
tcccttactc tcgagagtgt tcattgctgc act                                 153

<210> SEQ ID NO 7
<211> LENGTH: 24
<212> TYPE: DNA
<213> ORGANISM: Unknown
<220> FEATURE:
<223> OTHER INFORMATION: Mammal

<400> SEQUENCE: 7
ttgcattctt ttccaaataa gtgg                                           24

<210> SEQ ID NO 8
<211> LENGTH: 25
<212> TYPE: DNA
<213> ORGANISM: Unknown
<220> FEATURE:
<223> OTHER INFORMATION: Mammal

<400> SEQUENCE: 8
```

```
ttccaggatg aataggataa acagg                                             25

<210> SEQ ID NO 9
<211> LENGTH: 30
<212> TYPE: DNA
<213> ORGANISM: Unknown
<220> FEATURE:
<223> OTHER INFORMATION: Mammal

<400> SEQUENCE: 9
atccatcatc actccctgtg tttgtttccc                                        30

<210> SEQ ID NO 10
<211> LENGTH: 19
<212> TYPE: DNA
<213> ORGANISM: Unknown
<220> FEATURE:
<223> OTHER INFORMATION: Mammal

<400> SEQUENCE: 10
agctgactgc tgccgtcag                                                    19

<210> SEQ ID NO 11
<211> LENGTH: 31
<212> TYPE: DNA
<213> ORGANISM: Unknown
<220> FEATURE:
<223> OTHER INFORMATION: Mammal

<400> SEQUENCE: 11
tagactttgt agtgttagaa acatttggaa c                                      31

<210> SEQ ID NO 12
<211> LENGTH: 33
<212> TYPE: DNA
<213> ORGANISM: Unknown
<220> FEATURE:
<223> OTHER INFORMATION: Mammal

<400> SEQUENCE: 12
atttttgtaa tgcaatcatg tcaactgcaa tgc                                    33

<210> SEQ ID NO 13
<211> LENGTH: 22
<212> TYPE: DNA
<213> ORGANISM: Unknown
<220> FEATURE:
<223> OTHER INFORMATION: Mammal

<400> SEQUENCE: 13
ctcactctat cccatccaag gg                                                22

<210> SEQ ID NO 14
<211> LENGTH: 21
<212> TYPE: DNA
<213> ORGANISM: Unknown
<220> FEATURE:
<223> OTHER INFORMATION: Mammal

<400> SEQUENCE: 14
atgggcaggt agcatcccaca g                                                21

<210> SEQ ID NO 15
<211> LENGTH: 29
<212> TYPE: DNA
```

```
<213> ORGANISM: Unknown
<220> FEATURE:
<223> OTHER INFORMATION: Mammal

<400> SEQUENCE: 15
tgaatcatcc ctttgtctag cagaaccgg                                              29
```

US 8,962,913 B2

HUMANIZED IL-7 RODENTS

CROSS-REFERENCE TO RELATED APPLICATIONS

This application claims the benefit under 35 USC §119(e) of U.S. Provisional Application No. 61/660,976 filed 18 Jun. 2012, and U.S. Provisional Application No. 61/740,074 filed on 20 Dec. 2012, all of which are hereby incorporated by reference.

FIELD

Non-human animals (e.g., mammals, e.g., rodents such as mice, rats, and hamsters) that comprise a genetic modification comprising a replacement, at an endogenous locus, of a non-human IL-7 gene sequence with a human IL-7 gene sequence. Rodents and other non-human animals that express human IL-7 or humanized IL-7 from a locus under control of endogenous non-human regulatory sequences, or from an endogenous non-human IL-7 locus that comprises endogenous non-human regulatory sequences.

BACKGROUND

Transgenic mice that have randomly inserted transgenes that contain a human IL-7 sequence are known in the art. However, most if not all of these transgenic mice are not optimal in one aspect or another. For example, most mice transgenic for human IL-7 exhibit abnormal levels and/or ratios of certain cells, including T cells, that are likely due to a dysregulation of immune cell development, e.g., T cell development.

There remains a need in the art for non-human animals that comprise human IL-7-encoding sequences, wherein the human IL-7 encoding sequences are at an endogenous non-human IL-7 locus, and for non-human animals that express human IL-7 under the control of endogenous non-human regulatory elements. There is a need in the art for non-human animals that express human IL-7 in a manner that is as physiologically relevant in the non-human animal as possible. There is a need in the art for non-human animals that express a human IL-7, wherein the non-human animals lack a significant abnormality in peripheral T cells, and/or in ratios of T cell subtypes.

SUMMARY

Genetically modified non-human animals, cells, tissues, and nucleic acids are provided that comprise a human IL-7 genomic sequence at an endogenous non-human IL-7 locus. The non-human animals express a humanized IL-7 protein from a modified locus regulated by one or more endogenous non-human regulatory sequences of the modified endogenous IL-7 locus. In various embodiments, the non-human animals are rodents, e.g., mice, rats, hamsters, etc. In a specific embodiment, the rodent is a mouse or a rat.

In various embodiments and aspects, the non-human animals comprise a modified IL-7 gene in the germline of the non-human animal at a modified endogenous IL-7 locus, wherein the modified endogenous IL-7 locus comprises a humanization of at least a portion of the endogenous IL-7 gene. In various embodiments, the mice are heterozygous or homozygous with respect to the modified IL-7 locus. In one embodiment, a non-human animal is provided that comprises a lack of a first endogenous IL-7 allele and a humanization of a second endogenous IL-7 allele. In various embodiments and aspects, the humanization is of one or more exons and/or introns. In various embodiments and aspects, non-human animals having a modified IL-7 locus are provided wherein one or both of an endogenous non-human 5'-untranslated region and an endogenous non-human 3'-untranslated region are retained in the modified animal.

In one aspect, a genetically modified rodent is provided that comprises a replacement at an endogenous rodent IL-7 locus of an endogenous rodent IL-7 genomic sequence with a human IL-7 genomic sequence.

In one embodiment, the genetically modified rodent comprises a first rodent regulatory sequence upstream (with respect to the direction of transcription of the IL-7 gene) of the human IL-7 genomic sequence and a second rodent regulatory sequence downstream of the human IL-7 genomic sequence. In one embodiment, the first rodent regulatory sequence comprises a rodent promoter and/or enhancer, and the second rodent regulatory sequence comprises a 3'-UTR.

In one embodiment, the rodent is a mouse and comprises an endogenous mouse IL-7 gene locus having a mouse exon 1 and human exons 2, 3, 4, 5, and 6. In one embodiment, the endogenous mouse IL-7 gene locus comprises, from upstream to downstream with respect to the direction of transcription, mouse exon 1, at least a portion of a first mouse intron, and a contiguous human genomic fragment comprising human exon 2 through human exon 6. In one embodiment, the mouse further comprises a contiguous sequence of endogenous mouse DNA comprising an complete endogenous mouse IL-7 upstream (with respect to the direction of transcription of the IL-7 gene) promoter and regulatory region, wherein the contiguous mouse DNA is upstream of the human genomic fragment; and further comprises a contiguous sequence of endogenous mouse DNA 3'-UTR downstream of the human genomic fragment.

In one embodiment, the mouse comprises a mouse sequence that is at least 90%, at least 95%, at least 96%, at least 97%, at least 98%, or at least 99% identical with a sequence selected from SEQ ID NO:1, SEQ ID NO:2, and a combination thereof. In a specific embodiment, the mouse comprises a mouse sequence selected from SEQ ID NO:1 and SEQ ID NO:2.

In one aspect, a genetically modified mouse is provided that comprises a replacement at an endogenous mouse IL-7 locus of an endogenous mouse IL-7 genomic sequence with a human IL-7 genomic sequence to form a modified locus, wherein the human IL-7 genomic sequence comprises at least one human exon, and the modified locus comprises a mouse sequence selected from a sequence of SEQ ID NO:1, SEQ ID NO:2, and a combination thereof.

In one embodiment, the replacement comprises a human genomic fragment comprising exons 2 through 6, and the human genomic fragment is linked to mouse exon 1 to form a modified endogenous mouse IL-7 locus, wherein the modified mouse IL-7 locus comprises a mouse sequence selected from SEQ ID NO:1, SEQ ID NO:2, and a combination thereof.

In one aspect, a genetically modified rodent is provided that comprises an IL-7 gene that comprises a rodent exon 1 and at least a portion of a rodent intron 1, and a human IL-7 gene sequence of human IL-7 exons 2, 3, 4, 5, and 6, wherein the rodent comprises a sequence selected from a rodent upstream IL-7 regulatory sequence, a rodent IL-7 3'-UTR, and a combination thereof.

In one aspect, a genetically modified mouse is provided that comprises a sequence selected from SEQ ID NO:1, SEQ ID NO:2, and a combination thereof; wherein the mouse lacks an endogenous sequence encoding exons 2 through 5 of a mouse IL-7 protein, and the mouse comprises a nucleic acid sequence at an endogenous mouse IL-7 locus wherein the nucleic acid sequence encodes human IL-7 exons 2, 3, 4, 5, and 6.

In one aspect, a genetically modified rodent is provided that expresses a human or humanized IL-7 protein from an endogenous rodent IL-7 locus that is modified to express at least one human IL-7 exon. In one embodiment, the rodent IL-7 locus is modified to express a human or humanized iL7 protein encoded by a sequence comprising at least two human IL-7 exons. In one embodiment, the rodent IL-7 locus is modified to express a human or humanized IL-7 protein encoded by a sequence comprising at least three human IL-7 exons. In on embodiment, the rodent IL-7 locus is modified to express a human or humanized IL-7 protein encoded by a sequence comprising at least human IL-7 exons 2, 3, 4, 5, and 6 (i.e., 2 through 6). In one embodiment, the rodent IL-7 locus is modified to express a human IL-7 protein.

In one aspect, a genetically modified rodent is provided that expresses a human or humanized IL-7 protein from an endogenous mouse IL-7 locus that is modified to comprise at least human IL-7 exons 2 through 6 in place of mouse IL-7 exons 2 through 5.

In one aspect, a genetically modified rodent is provided that expresses a human or humanized IL-7 protein from a humanized endogenous rodent IL-7 locus comprising a humanized endogenous rodent IL-7 coding region, wherein the humanized endogenous rodent IL-7 locus comprises all endogenous rodent regulatory elements that are present in a wild-type rodent upstream of a wild-type rodent IL-7 coding region and that are downstream of the wild-type rodent IL-7 coding region.

In one aspect, a genetically modified rodent is provided that expresses a human or humanized IL-7 protein from a humanized rodent IL-7 locus that comprises rodent regulatory regions upstream and downstream of a nucleic acid sequence encoding the human or humanized IL-7 protein, wherein the human or humanized IL-7 protein is expressed in an expression pattern that is about the same as the expression pattern of a rodent IL-7 protein in a wild-type rodent. In one embodiment, the level of serum expression of the human or humanized IL-7 is about the same as the level of serum expression of a rodent IL-7 protein in a wild-type rodent.

In one aspect, a genetically modified rodent is provided that expresses a humanized IL-7 protein, wherein the lymphocyte population of the rodent is characterized by its B cell population that is about the same in number as a population of B cells in an age-matched wild-type mouse. In one embodiment, the modified rodent is characterized by a population of mature B cells that is about the same in number as a population of mature B cells in an age-matched wild-type mouse. In one embodiment, the humanized IL-7 protein is identical to a human IL-7 protein. In one embodiment, the humanized IL-7 protein comprises human sequence encoded by at least exons 2 through 6 of a human IL-7 gene.

In one aspect, a genetically modified rodent is provided that expresses a humanized IL-7 protein, wherein the lymphocyte population of the rodent is characterized by a population of T cells that is about the same in number as a population of T cells in an age-matched wild-type mouse. In one embodiment, the modified rodent exhibits a population of mature T cells that is about the same in number as a population of mature T cells in an age-matched wild-type mouse. In one embodiment, the modified rodent exhibits a population of peripheral T cells that is about the same in number as the population of peripheral T cells in an age-matched wild-type mouse. In one embodiment, the humanized IL-7 protein is identical to a human IL-7 protein. In one embodiment, the humanized IL-7 protein comprises human sequence encoded by at least exons 2 through 6 of a human IL-7 gene.

In one aspect, a genetically modified rodent is provided that expresses a humanized IL-7 protein, wherein the lymphocyte population of the rodent is characterized by a T cell population that exhibits a CD4:CD8 ratio that is about the same as the CD4:CD8 ratio in the T cell population of an age-matched wild-type mouse. In one embodiment, the humanized IL-7 protein is identical to a human IL-7 protein. In one embodiment, the humanized IL-7 protein comprises human sequence encoded by at least exons 2 through 6 of a human IL-7 gene.

In one aspect, a genetically modified rodent is provided that expresses a humanized IL-7 protein, wherein the rodent comprises a characteristic selected from a lack of a propensity to develop a chronic colitis; lack of over-expression of IL-7 in colonic mucosal lymphocytes; normal, or wild-type, expression of IL-7 in colonic mucosal lymphocytes; lacks a severe dermatitis; lacks a dermatitis characterized by a massive dermal infiltration of mononuclear cells; exhibits a CD4:CD8 ratio in its T cell population that is about the same as the CD4:CD8 ratio of an age-matched wild-type mouse; exhibits an expression pattern of human IL-7 that is about the same as an expression pattern of mouse IL-7 in a wild-type mouse; and a combination thereof.

In one aspect, a genetically modified rodent is provided that expresses a humanized IL-7 protein, wherein the rodent lacks a propensity to develop a chronic colitis.

In one aspect, a genetically modified rodent is provided that expresses a humanized IL-7 protein, wherein the rodent does not exhibit over-expression of IL-7 in colonic mucosal lymphocytes.

In one aspect, a genetically modified rodent is provided that expresses a humanize IL-7 protein, wherein the rodent does not exhibit a dermatitis characterized by a massive dermal infiltration of mononuclear cells.

In one aspect, a genetically modified rodent is provided that expresses a humanized IL-7 protein, wherein the rodent does not exhibit a lymphoproliferation into dermis.

In one aspect, a genetically modified rodent is provided that expresses a humanized IL-7 protein, wherein the rodent does not exhibit B and/or T cell lymphomas at a higher frequency than an age-matched wild-type mouse.

In one aspect, a genetically modified mouse is provided that expresses a humanized IL-7 protein, or a human IL-7 protein, wherein the mouse is no more prone than a wild-type mouse to developing a pathology selected from colitis, chronic colitis, severe dermatitis, pathological and/or massive infiltration of the dermis by mononuclear cells, lymphoproliferation of the dermis, B cell lymphomas, T cell lymphomas, reduction in the number of mature B and/or T cells, reduction in the number of peripheral B and/or T cells, abnormal numbers of CD4+ T cells, abnormal numbers of CD8+ T cells, and a combination thereof.

In one aspect, a genetically modified non-human animal is provided, comprising in its germline a replacement of at least one non-human IL-7 exon with at least one human IL-7 exon to form a human or humanized IL-7-encoding gene, wherein the replacement is at an endogenous non-human IL-7 locus, wherein the human or humanized IL-7-encoding gene is under control of endogenous non-human regulatory elements.

In one embodiment, the genetically modified non-human animal is a rodent. In one embodiment, the rodent is selected from a rat and a mouse.

In on embodiment, the human or humanized IL-7-encoding gene comprises human exons selected from the group consisting of human exon 1, human exon 2, human exon 3, human exon 4, human exon 5, human exon 6, and a combination thereof. In one embodiment, the human or humanized IL-7-encoding gene comprises no more than five human exons.

In one embodiment, the genetically modified non-human animal is a rodent that is a mouse and the modified locus comprises a replacement of mouse exons 2, 3, 4, and 5 with a human genomic segment comprising human IL-7 exons 2, 3, 4, 5, and 6.

In one embodiment, the human or humanized IL-7-encoding gene comprises a cDNA encoding a human or humanized IL-7 protein.

In one aspect, a genetically modified non-human animal is provided, comprising in its germline a transgene comprising a nucleic acid sequence encoding a human or humanized IL-7 gene, wherein the human or humanized IL-7 gene is flanked upstream and downstream with endogenous non-human regulatory sequences.

In one embodiment, the genetically modified non-human animal is a rodent. In one embodiment, the rodent is selected from the group consisting of a mouse, a rat, and a hamster.

In one embodiment, the genetically modified non-human animal comprises a human exon selected from the group consisting of human exon 1, human exon 2, human exon 3, human exon 4, human exon 5, human exon 6, and a combination thereof. In one embodiment, the human or humanized IL-7 gene comprises at least five human exons.

In one aspect, a method is provided for making a non-human animal with a human or humanized IL-7-encoding gene, comprising modifying the germline of the non-human animal to comprise a human or humanized IL-7-encoding gene flanked upstream and downstream with endogenous non-human IL-7 regulatory sequences.

In one embodiment of the method, the modification is at an endogenous non-human IL-7 locus.

In one embodiment of the method, the non-human animal is a rodent. In one embodiment, the rodent is selected from the group consisting of a mouse, a rat, and a hamster.

In one aspect, a genetically modified non-human animal is provided that is genetically modified to express human IL-7 in an expression pattern that is the same expression pattern as observed for a wild-type non-human animal of the same genus and species. In one embodiment, the non-human animal is a rodent. In a specific embodiment, the rodent is selected from a mouse and a rat.

In one embodiment, the genetically modified non-human animal of claim 17, wherein the level of human IL-7 expressed in the non-human animal is about the same as the level of non-human IL-7 in a corresponding wild-type mouse. In one embodiment, the non-human animal is a rodent. In a specific embodiment, the rodent is selected from a mouse and a rat.

In one aspect, a DNA construct is provided, comprising from 5' to 3' with respect to direction of transcription, a nucleic acid sequence homologous to a mouse IL-7 5' noncoding sequence, a human genomic fragment encoding a human IL-7 protein but not comprising a human regulatory sequence upstream or downstream of sequence encoding the human IL-7 protein, and a nucleic acid sequence homologous to a mouse IL-7 3' noncoding sequence.

In one aspect, a DNA construct is provided, comprising from 5' to 3' with respect to direction of transcription, a nucleic acid sequence that comprises a region of homology to a mouse IL-7 exon 1 sequence, a human genomic fragment encoding a human IL-7 protein but not comprising a human regulatory sequence upstream or downstream of sequence encoding the human IL-7 protein, and a nucleic acid sequence homologous to a mouse IL-7 3' noncoding sequence.

In one aspect, a genetically modified rodent cell is provided, wherein the rodent cell comprises a replacement at an endogenous rodent IL-7 locus of a gene sequence encoding a rodent IL-7 with a human genomic sequence encoding a human IL-7.

In one embodiment, the human genomic sequence comprises a contiguous human nucleic acid sequence spanning human IL-7 exons 2 through human IL-7 exon 6.

In one embodiment, the genetically modified rodent comprises a mouse IL-7 promoter at the endogenous rodent IL-7 locus.

In one embodiment, the cell is selected from a pluripotent cell, an induced pluripotent cell, a totipotent cell, an ES cell, and an ovum.

In one embodiment, the cell secretes human IL-7. In one embodiment, the cell that secretes human IL-7 is selected from an epithelial cell (e.g., an intestinal epithelial cell), a hepatocyte, a keratinocyte, a dendritic cell, and a follicular dendritic cell.

In one embodiment, the rodent cell is a bone marrow dendritic cell. In one embodiment, the cell that secretes human IL-7 is a thymic stromal cell; in a specific embodiment, the thymic stromal cell is a cortical epithelial cell.

In one aspect, a rodent embryo is provided, wherein the embryo comprises at least one rodent donor cell (e.g., an ES cell, a pluripotent cell, a totipotent cell, etc.) comprising a replacement of an endogenous rodent IL-7-encoding nucleic acid sequence with a nucleic acid sequence encoding a human IL-7 at the endogenous rodent IL-7 locus. In one embodiment, the donor cell is a mouse ES cell and the embryo is a host mouse embryo that is a pre-morula, a morula, or a blastocyst.

In one aspect, a rodent tissue that comprises a humanized IL-7 gene at an endogenous rodent IL-7 locus is provided, wherein the rodent tissue is selected from thymic, splenic, epidermal, and intestinal.

In one aspect, a genetically modified mouse is provided that comprises a DNA sequence that encodes a human IL-7, wherein the mouse does not express a mouse IL-7, and wherein the mouse exhibits a T cell population that is about the same size as the T cell population of a wild-type mouse.

In one embodiment, the mouse exhibits a peripheral T cell population that is about the same size as a peripheral T cell population of a wild-type mouse.

In one embodiment, the T cell population is a mouse T cell population.

In one embodiment, the mouse is not more prone than a wild-type mouse to develop a B cell tumor comprising a pro-B or a pre-B cell.

In one embodiment, the mouse is not more prone than a wild-type mouse to develop a lymphoid tumor.

In one embodiment, the mouse does not exhibit a lymphoproliferative disorder in the absence of a known lymphoproliferative causative agent.

In one embodiment, the mouse does not exhibit a pathologic infiltration of T cell in a skin layer. In one embodiment, the mouse does not exhibit a symptom of alopecia.

In one embodiment, the majority of T cells of the genetically modified mouse are about the same in size distribution as in an age-matched wild-type mouse. In a specific embodiment, the genetically modified mouse does not exhibit an enlargement of T cell In one aspect, a rodent is provided that expresses a humanized or human IL-7 protein from an endogenous modified rodent IL-7 locus, wherein the serum concentration of human IL-7 in the rodent is physiologically normal.

In one aspect, a humanized rodent is provided that expresses a humanized IL-7 gene in the serum of the rodent at a physiologically normal concentration.

In one embodiment, the rodent is selected from a mouse and a rat.

In one embodiment, the physiologically normal serum concentration of human IL-7 is less than 10 picograms/mL. In one embodiment, the physiologically normal serum concentration of human IL-7 is less than 5 picograms/mL. In one embodiment, the physiologically normal serum concentration of human IL-7 in the rodent is about 2 picograms/mL to about 4 picograms/mL. In one embodiment, the physiologically normal serum concentration of human IL-7 in the rodent serum is about 2.4 picograms/mL to about 3.2 picograms/mL.

In one aspect, a method for making a human IL-7 protein is provided, comprising inserting into the germline of the non-human animal a human or humanized IL-7 coding gene under control of endogenous non-human regulatory elements, allowing the non-human animal to make the human or humanized IL-7, and isolating from the non-human animal (e.g., a mammal, e.g., a rodent such as, e.g., a mouse or rat or hamster) human or humanized IL-7.

In one aspect, a method for making a human IL-7 protein is provided, comprising isolating from a non-human animal as described herein (e.g., a mammal, e.g., a rodent such as, e.g., a mouse or rat or hamster).

In one aspect, a method is provided for making a non-human animal that comprises a human or humanized IL-7 gene in its germline, comprising inserting into the germline of the non-human animal a human or humanized IL-7-encoding nucleic acid sequence or fragment thereof, wherein the human or humanized IL-7-coding nucleic acid sequence or fragment thereof is under regulatory control of endogenous non-human regulatory elements. In one embodiment, the human or humanized IL-7 gene is at an endogenous non-human IL-7 locus (i.e., inserted between upstream and downstream non-human regulatory elements at the endogenous non-human IL-7 locus, wherein the human or humanized IL-7-coding nucleic acid sequence replaces the wild-type existing non-human IL-7 coding sequence in whole or in part). In one embodiment, the non-human animal is a mammal, e.g., rodent. In one embodiment, the rodent is selected from a mouse, a rat, and a hamster.

In one aspect, a method is provided for isolating from a non-human animal a T cell that has been exposed to a human or humanized IL-7 protein, comprising a step of isolating a T cell from a non-human animal as described herein. In one embodiment, the non-human animal is a mouse or a rat. In one embodiment, the T cell is a non-human T cell, e.g., a rodent T cell, e.g., a T cell of a mouse or a rat. In one embodiment, the T cell is selected from a T cell in the thymus and a peripheral T cell.

In one aspect, a method for identifying an agent that is an antagonist of human IL-7 is provided, comprising a step of administering an agent to a genetically modified rodent as described herein, determining an effect of the agent on a human IL-7 mediated function in the rodent, and identifying the agent as an IL-7 antagonist if it antagonizes the function of human IL-7 in the genetically modified rodent.

In one embodiment, the agent comprises an immunoglobulin variable domain that binds IL-7. In one embodiment, the agent specifically binds human IL-7 but not rodent IL-7. In one embodiment, the agent is an antibody.

In one aspect, a method for determining whether an agent reduces IL-7-mediated peripheral T cell population is provided, comprising a step of administering to a genetically modified rodent as described herein an IL-7 antagonist for a period of time, measuring peripheral T cell population number of the rodent at one or more time periods following administration, and determining whether the IL-7 antagonist reduces the peripheral T cell population.

In one aspect, the genetically modified non-human animal is heterozygous for a human or humanized IL-7-encoding gene. In one embodiment, the non-human animal is unable to express an endogenous IL-7 protein. In a specific embodiment, the non-human animal comprises a knockout of both endogenous IL-7 alleles.

Each of the aspects and embodiments described above and below may be used together, unless otherwise stated and unless otherwise clear from the context.

DETAILED DESCRIPTION

Figure 1:
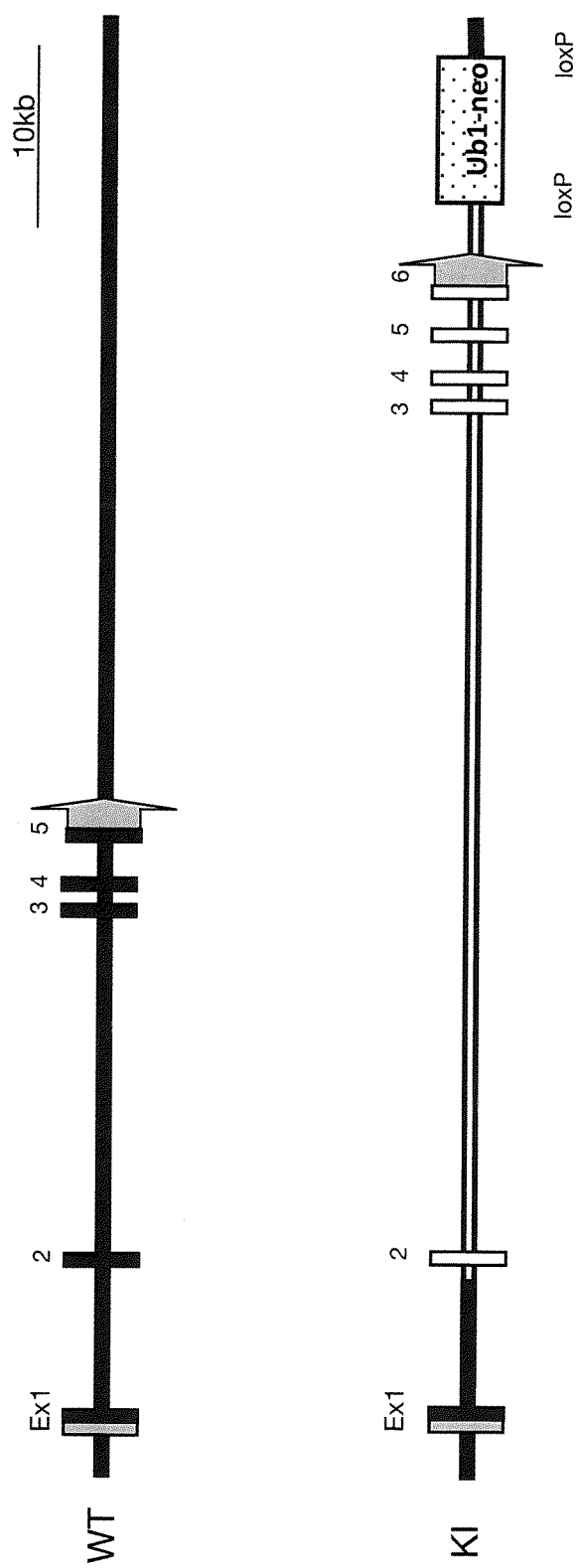
FIG. 1 depicts (not to scale) a schematic of a wild-type mouse IL7 gene locus (top) and a humanized endogenous mouse IL-7 locus (bottom). Open symbols indicate human sequence; closed symbols indicate mouse sequence; shaded items indicate untranslated regions; stippled region indicates other sequence.

In various embodiments, non-human animals are described that comprise the genetic modification(s) described herein. The genetically modified non-human animal may be selected from a group consisting of a mouse, rat, rabbit, pig, bovine (e.g., cow, bull, buffalo), deer, sheep, goat, chicken, cat, dog, ferret, primate (e.g., marmoset, rhesus monkey). For the non-human animals where suitable genetically modifiable ES cells are not readily available, other methods are employed to make a non-human animal comprising the genetic modification. Such methods include, e.g., modifying a non-ES cell genome (e.g., a fibroblast or an induced pluripotent cell) and employing nuclear transfer to transfer the modified genome to a suitable cell, e.g., an oocyte, and gestating the modified cell (e.g., the modified oocyte) in a non-human animal under suitable conditions to form an embryo.

In one aspect, the non-human animal is a mammal. In one aspect, the non-human animal is a small mammal, e.g., of the superfamily Dipodoidea or Muroidea. In one embodiment, the genetically modified animal is a rodent. In one embodiment, the rodent is selected from a mouse, a rat, and a hamster. In one embodiment, the rodent is selected from the superfamily Muroidea. In one embodiment, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, Malagasy rats and mice), Platacanthomyidae (e.g., spiny dormice), and Spaiacidae (e.g., mole rates, bamboo rats, and zokors). In a specific embodiment, the genetically modified rodent is selected from a true mouse or rat (family Muridae), a gerbil, a spiny mouse, and a crested rat. In one embodiment, the genetically modified mouse is from a member of the family Muridae. In one embodiment, the animal is a rodent. In a specific embodiment, the rodent is selected from a mouse and a rat. In one embodiment, the non-human animal is a mouse.

In various embodiments, the non-human animal is a rodent that is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/OIa. In another embodiment, the mouse is a 129 strain selected from the group consisting of a strain that is 129P1, 129P2, 129P3, 129X1, 129S1 (e.g., 129S1/SV, 129S1/SvIm), 129S2, 129S4, 129S5, 12959/SvEvH, 129S6 (129/SvEvTac), 129S7, 129S8, 129T1, 129T2 (see, e.g., Festing et al. (1999) Revised nomenclature for strain 129 mice, Mammalian Genome 10:836, see also, Auerbach et al (2000) Establishment and Chimera Analysis of 129/SvEv- and C57BL/6-Derived Mouse Embryonic Stem Cell Lines). In a specific embodiment, the genetically modified mouse is a mix of an aforementioned 129 strain and an aforementioned C57BL/6 strain. In another specific embodiment, the mouse is a mix of aforementioned 129 strains, or a mix of aforementioned BL/6 strains. In a specific embodiment, the 129 strain of the mix is a 129S6 (129/SvEvTac) strain. In another embodiment, the mouse is a BALB strain, e.g., BALB/c strain. In one embodiment, the mouse is a mix of a BALB strain and another aforementioned strain.

In one embodiment, the non-human animal is a rat. In one embodiment, the rat is selected from a Wistar rat, an LEA strain, a Sprague Dawley strain, a Fischer strain, F344, F6, and Dark Agouti. In one embodiment, the rat strain is a mix of two or more strains selected from the group consisting of Wistar, LEA, Sprague Dawley, Fischer, F344, F6, and Dark Agouti.

Genetically modified non-human animals that comprise a replacement of a non-human IL-7 gene sequence with a human IL-7 gene sequence are provided. Rodents that comprise a humanization of an IL-7 gene, at an endogenous rodent IL-7 locus, are provided. Methods for making rodents, e.g., mice, that comprise a replacement of an endogenous IL-7 gene or fragment thereof (e.g., a fragment comprising one or more exons) with a humanized IL-7 gene, or fragment thereof (e.g., a fragment comprising one or more exons), at the endogenous IL-7 locus. Cells, tissues, and mice are provided that comprise the humanized gene are provided, as well as cells, tissues, and mice that express human IL-7 from an endogenous non-human IL-7 locus.

IL-7 is a cytokine that is essential for development of immature B and T cells and, to some degree, mature T cells; IL-7 knockout mice display a severe depletion of mature B and T cells (von Freeden-Jeffry U. et al. (1995) Lymphopenia in interleukin (IL)-7 gene-deleted mice identifies IL-7 as a nonredundant cytokine, J. Exp. Med. 181:1519-1526). The depletion is apparently due to a block between pro-B and pre-B cells, and a block in T cell proliferation (rather than a block in T cell differentiation; ratios of T cell types in IL-7 KO mice are about normal) that results in a depressed population of T cells and mature B cells (Id.). IL-7 is produced by epithelial cells in the thymus and intestine, in keratinocytes, liver, and dendritic cells—but not by normal lymphocytes (reviewed, e.g., in Fry T. J. and Mackall, C. L. (2002) Interleukin-7: from bench to clinic, Blood 99(11):3892-3904).

Simply put, IL-7 increases T cell number and enhances T cell function (see, e.g., Morrissey, J. J. (1991) Administration of IL-7 to normal mice stimulates B-lymphopoiesis and peripheral lymphadenopathy, J. Immunol. 147:561-568; Faltynek, C. R. et al. (1992) Administration of human recombinant IL-7 to normal and irradiated mice increases the numbers of lymphocytes and some immature cells of the myeloid lineage, J. Immunol. 149:1276-1282; Risdon, G. J. et al. (1994) Proliferative and cytotoxic responses of human cord blood T lymphocytes following allegenic stimulation, Cell. Immunol. 154:14-24). Functional enhancement of T cells can be achieved by a short duration of IL-7 exposure, whereas increases in T cell number reflect a proliferative effect that is achieved with a longer duration exposure (Geiselhart, L. A. et al. (2001) IL-7 Administration Alters the CD4:CD8 Ratio Increases T Cell Numbers, and Increases T Cell Function in the Absence of Activation, J. Immunol. 166:3019-3027; see also, Tan J. T. et al. (2001) IL-7 is critical for homeostatic proliferation and survival of naïve T cells, Proc. Natl. Acad. Sci. USA 98(15):8732-8737).

IL-7 is necessary for both early and late stage T cell regulation. IL-7 is not expressed by T cells, which must encounter IL-7 that is released by non-thymic cells in the periphery and that is believed to be responsible for peripheral T cell proliferation and maintenance (reviewed, e.g., in Guimond, M (2005) Cytokine Signals in T-Cell Homeostasis, J. Immunother. 28(4):289-294). IL-7 starvation results in severely impaired T cell development and survival of naïve T cells. IL-7 also appears to be necessary for the survival of mature T cells; mature T cells acquired through adoptive transfer into IL-7-deficient mice enter apoptosis where the mice lack an IL-7 gene, but not in mice that express IL-7 that lack an IL-7R gene (Schluns, K. S. et al. (2000) Interleukin-7 mediates the homeostasis of naïve and memory CD8 T cells in vivo, Nat. Immunol. 1(5):426-432. Loss of IL-7 function results in a SCID-like phenotype in mice (Puel, A. and Leonard, W. J. (2000) Mutations in the gene for the IL-7 receptor result in T(-)B(+)NK(+) severe combined immunodeficiency disease, Curr. Opin. Immunol. 12:468-473), presumably due to T cell atrophy and death caused by diminished growth rate likely mediated by glycolytic insufficiency in the absence of IL-7 stimulus (Jacobs, S. R. et al. (2010) IL-7 Is Essential for Homeostatic Control of T Cell Metabolism In Vivo, J. Immunol. 184:3461-3469).

The human IL-7 gene comprises 6 exons that extend over 33 kb and is located on chromosome 8 at 8q12-13. Mouse IL-7 comprises 5 exons (there is no counterpart in mouse to human exon 5) and is about 80% homologous to the human gene; analysis of non-coding sequences of the human and the mouse genes revealed a paucity of recognizable regulatory motifs responsible for transcription and regulation of gene expression (Lupton, S. D. et al. (1990) Characterization of the Human and Murine IL-7 Genes, J. Immunol. 144(9):3592-3601), suggesting that regulation of IL-7 expression may be complex. However, mouse BAC fragments comprising a reporter gene at the hIL-7 locus have been expressed in mice to successfully ascertain expression patterns of IL-7 in mice (see, e.g., Avles, N. L. et al. (2009) Characterization of the thymic IL-7 niche in vivo, Proc. Natl. Acad. Sci. USA 106 (5):1512-1517; Mazzucchelli, R. I. (2009) Visualization and Identification of IL-7 Producing Cells in Reporter Mice, PLoS ONE 4(11):e7637; Repas, J. F. et al. (2009) IL7-hCD25 and IL7-Cre BAC transgenic mouse lines: new tools for analysis of IL-7 expressing cells, Genesis 47:281-287). In at least one case, a BAC-based replacement of an IL-7 exon with a reporter required the entire 43 kb IL-7 locus as well as 96 kb of 5' flanking sequence and 17 kb of 3' flanking sequence in the hope of faithfully recapitulating IL-7 expression of wild-type mice (Repass, J. F. et al. (2009)). In any case, data from the different studies on reporter expression driven by putative IL-7 regulatory elements vary somewhat from one another and from earlier observations, supporting an inference that IL-7 regulation might not have been faithfully recapitulated in these reporter mice (IL-7 reporter transgenic mice are reviewed in Kim, G. Y. et al. (2011) Seeing Is Believing: Illuminating the Source of In Vivo Interleukin-7, Immune Network 11(1):1-10). Human IL-7 is functional on mouse cells, but mouse IL-7 is not functional on human cells.

Transgenic mice that express abnormally or poorly regulated human IL-7 exhibit a panoply of pathologies or syndromes. Mice transgenic for a murine IL-7 cDNA under control of mouse Ig heavy chain enhancer, κ light chain enhancer, and light chain promoter) to target expression in the lymphoid compartment) exhibit significantly enhanced numbers of B cell precursors and an overall expansion of all subsets of thymocytes in the thymus and peripheral T cells (Samaridis, J. et al. (1991) Development of lymphocytes in interleukin 7-transgenic mice, Eur. J. Immunol. 21:453-460).

Transgenic mice that express IL-7 from a mouse cDNA under control of an SRα promoter develop a panoply of pathologies, including a chronic colitis that histopathologically mimics chronic colitis in humans, and is characterized by at least a transient over-expression of IL-7 in colonic mucosal lymphocytes (but not colonic epithelial cells) and its apparent accumulation in mucus of goblet cells of the colonic mucosa (Watanabe, M. et al. (1998) Interleukin 7 Transgenic Mice Develop Chronic Colitis with Decreased Interleukin 7 Protein Accumulation in the Colonic Mucosa, J. Exp Med. 187(3):389-402; Takebe, Y. et al. (1988) sR alpha promoter: an efficient and versatile mammalian cDNA expression system composed of the simian virus 40 early promoter and the R-U5 segment of human T-cell leukemia virus type 1 long terminal repeat, Mol. Cell Biol. 8(1):466-472). Constitutive expression of mouse IL-7 driven by the same promoter in transgenic mice also develop a severe dermatitis characterized by gross deformities and a massive dermal infiltration of mononuclear cells that are mostly TCRγẟ cells (Uehira, M. et al. The development of dermatitis infiltrated by γẟ T cells in IL-7 transgenic mice, Intl. Immunol. 5(12):1619-1627). Transgenic mice expressing a murine IL-7 cDNA driven by a murine heavy chain promoter and enhancer also exhibited dermatitis and lymphoproliferation into the dermis, but reportedly of TCRαβ cells and cells that express Thy-1, CD3, and CD5 but lack CD4 and CD8 (CD4+/CD8+ thymocytes are virtually absent from these transgenic mice); these mice also developed B and T cell lymphomas, presumably associated with a prolonged lymphoproliferation observed in these mice (see, Rich, B. E. et al. (1993) Cutaneous lymphoproliferation and lymphomas in interleukin 7 transgenic mice, J. Exp. Med. 177:305-316).

Dysregulation of the IL-7 gene is associated with a variety of pathological states. Mice expressing transgenic mouse IL-7 under control of the MHC class II Eα promoter are highly prone to lympoid tumors (see, e.g., Fisher, A. G. et al. (1995) Lymphoproliferative disorders in IL-7 transgenic mice: expansion of immature B cells which retain macrophage potential, Int. Immunol. 7(3):414-423; see, also, Ceredig, R. et al. (1999) Effect of deregulated IL-7 transgene expression on B lymphocyte development in mice expressing mutated pre-B cell receptors, Eur. J. Immunol. 29(9):2797-2807). T cell sizes are also larger in the transgenic mice, and a polyclonal T cell expansion is observed (predominantly CD8+, indicating a perturbed regulation in these mice) (Mertsching, E. et al. IL-7 transgenic mice: analysis of the role of IL-7 in the differentiation of thymocytes in vivo and in vitro, Intl. Immunol. 7(3):401-414). Other transgenic mice that overexpress mIL-7 (by about 25-50-fold) through the MHC class II Ea promoter appear grossly healthy (but for a low incidence of B cell tumors) and exhibit a 10-20-fold increase in T cell number over wild-type mice, characterized by large numbers of CD8+ cells that are also CD44$^{hi}$ and CD122$^{hi}$ (Kieper W. C. et al. (2002) Overexpression of Interleukin (IL)-7 Leads to IL-15-independent Generation of Memory Phenotype CD8+ T Cells, J. Exp. Med. 195(12):1533-1539).

Mice that constitutively express mouse IL-7 from a cDNA under control of the MHC class II Eα promoter selectively expand IL-7-responsive early B cells, and are a good source of tumors comprising pro-B and pre-B cells. Mice that express IL-7 driven by a human K14 promoter develop a lymphoproliferative response that results in T cell infiltrates of skin that resemble alopecia.

Mice transgenic for IL-7R display large reductions in double negative (CD4-CD8-) precursor cells in thymus, presumably due to depletion of IL-7 by the large number of double positive thymocytes in the transgenic mice, suggesting that IL-7 levels must be exquisitely controlled to promote normal thymocyte development (see, e.g., Malek, T. R. (2004) IL-7: a limited resource during Chymopoiesis, Blood, 104(13):2842).

As early as the cloning of human IL-7, it has been known that human IL-7 can induce proliferation of murine pre-B cells (Goodwin, R. G. et al. (1989) Human interleukin 7: Molecular cloning and growth factor activity on human and murine B-lineage lines, Proc. Natl. Acad. Sci. USA 86:302-306). Although expressed in certain chronic lymphocytic leukemia cells, expression of mouse IL-7 in tumor cells implanted in mice induce inflammation and reduced tumorigenicity, yet paradoxically mice transgenic for IL-7 are prone to lymphomas (reviewed in Foss, H.-D. et al. (1995) Frequent Expression of IL-7 Gene Transcripts in Tumor Cells of Classical Hodgkin's Disease, Am. J. Pathol. 146(1):33-39). Thus, it is desirable to obtain mice that express human IL-7 (but not mouse IL-7) from endogenous mouse IL-7 loci in a physiologically relevant fashion, in particular but not limited to mice that comprise human or mouse tumors, e.g., lymphocytic tumors.

Mice that express human IL-7 in a physiologically relevant manner are also useful for evaluating anti-tumor properties of putative therapeutics (including human IL-7 and analogs thereof) in xenograft models of human solid tumors in mice. For example, SCID mice implanted with HT29 human colon adenocarcinoma and tested under a variety of conditions (e.g., ablation of native T cells and addition of human T cells; addition of recombinant human IL-7, etc.) (see, Murphy, W. J. et al. (1993) Antitumor Effects of Interleukin-7 and Adoptive Immunotherapy on Human Colon Carcinoma Xenografts, J. Clin. Invest. 92:1918-1924). That study found that human IL-7 when administered with human T cells resulted in a significantly prolonged survival than in the absence of human IL-7 (Id.).

Thus, mice that express human IL-7, in particular mice that are capable of supporting a xenograft (e.g., a human tumor), such as, e.g., immunodeficient mice, have a specific and a well-established utility. IL-7 signaling has been shown to be necessary for development and survival of human T-cell acute lymphoblastic leukemias (T-ALL) in vitro and in vivo. (Touw, I. et al. (1990) Interleukin-7 is a growth factor of precursor B and T acute lymphoblastic leukemia. Blood 75, 2097-2101) T-ALL is an aggressive hematological cancer with poor prognosis; the understanding of mechanisms driving proliferation and survival of T-ALL cells remains relatively poor due to lack of xenograft models that can support the growth of patient derived tumors in vivo. Thus, an immunodeficient animal expressing human IL-7 can serve as an invaluable in vivo system for testing pharmaceutical compositions against such T-cell related malignancies, e.g., testing the efficacy of a pharmaceutical composition to target IL-7-mediated signaling in a mouse that expresses human IL-7 and has an implanted T-cell derived tumor, wherein the tumor requires IL-7 signaling for development and survival.

EXAMPLES

Example 1

Humanizing the Mouse IL-7 Locus

Mouse ES cells were modified to replace mouse IL-7 gene sequences with human IL-7 gene sequences at the endogenous mouse IL-7 locus, under control of mouse IL-7 regulatory elements, using VELOCIGENE® genetic engineering technology, to produce a humanized locus as shown in FIG. 1.

Targeting Construct.

Bacterial homologous recombination (BHR) is performed to construct a large targeting vector (LTVEC) containing the human IL-7 gene for targeting to the mouse IL-7 locus using standard BHR techniques (see, e.g., Valenzuela et al. (2003) High-throughput engineering of the mouse genome coupled with high-resolution expression analysis, Nature Biotech. 21(6):652-659). Linear fragments are generated by ligating PCR-generated homology boxes to cloned cassettes followed by gel isolation of ligation products and electroporation into BHR-competent bacteria harboring the target bacterial artificial chromosome (BAC). Mouse BAC bMQ-271g18 is used as the source of mouse sequence; human BAC RP11-625K1 is used as the source of human sequence. Following a selection step, correctly recombined clones are identified by PCR across novel junctions, and by restriction analysis. A large targeting vector (LTVEC) containing the homology arms and human IL-7 gene sequences was made. Mouse ES cells were electroporated with the LTVEC constructs, grown on selection medium, and used as donor ES cells to make humanized IL-7 mice.

The mouse IL-7 gene (mouse GeneID: 96561; RefSeq transcript: NM_008371.4) is modified by deleting exons 2 through 5 (deletion coordinates NCBIM37:ch3:7604650-7573021; minus strand) and replacing them with human IL-7 (EntrezGeneID:6023; RefSeq transcript NM_000880.3) exons 2 through 6 (replacement coordinates GRCh37Lch*: 79711168-79644608; minus strand). The human genomic IL-7 sequence is provided in SEQ ID NO:3 (NC#166E2F2). The mouse genomic IL-7 locus is known and reported as a 41,351 nt sequence under accession number NC0000696 (hereby incorporated by reference); relevant 5' and 3' sequences of the mouse IL-7 genomic locus are provided in SEQ ID NO:1 (5' flanking) and SEQ ID NO:2 (3' flanking).

The LTVEC comprising the humanized IL-7 gene had a 48 kb upstream mouse targeting arm flanked upstream with a NotI site, and a 77 kb downstream mouse targeting arm flanked downstream with a NotI site. The LTVEC was linearized with NotI for electroporation.

Following construction of the LTVEC, nucleotide sequence of the LTVEC was obtained across the mouse/human 5' junction, which included, from 5' (mouse) to 3' (human), the following sequence with the mouse/human junction nucleotides in uppercase:

(SED ID NO: 4)
5'- tgcaagcacc aaaaaggtga ccacacttca cattggcgat cgcGGgtttc tatctgagga tgtgaattta tttacaga -3'.

Nucleotide sequence of the LTVEC across the junction of the human insertion and the 5' end of the cassette (see FIG. 1) was determined and included the following sequence having, from 5' to 3', human sequence/restriction site/loxp/cassette sequence with the human sequence/restriction site junction nucleotides in uppercase:

(SEQ ID NO: 5)
5'-
gttatgtgct gatgggcttt atttgatcta cagaagatgc tctggtgaca ccctcagtgt gtgttggtaa caccttcctg CCtcgagata acttcgtata atgtatgcta tacgaagtta tatgcatggc ctccgcgccg ggtttggcg cc -3'.

Nucleotide sequence of the LTVEC across the junction of the end of the cassette and the beginning of mouse sequence was determined and included the following sequence having, from 5' to 3', cassette sequence/restriction site/mouse sequence with the junction nucleotides in uppercase:

(SEQ ID NO: 6)
5'- gtatgctata cgaagttatg ctagtaacta taacggtcct aaggtagcga gctagCCcaa ttgcgtactt tggatagtgt ctcttttaa cctaaatgac ctttattaac actgtcaggt tcccttactc tcgagagtgt tcattgctgc act -3'.

Following electroporation of the ES cell, a loss of native allele assay (see, e.g., Valenzuela et al. (2003)) is performed to detect loss of endogenous IL-7 sequence due to the targeting. Primer pairs, fragment sizes, and TAQMAN™ probes are as shown in Table 1. The C1 probe binds the mouse IL-7 genomic sequence (NC0000696) at nts 9,635-9,664; the C2 probe binds the mouse IL-7 genomic sequence (NC0000696) at nts 39,793-39,825. For a gain of allele assay, the C3 probe binds the human IL-7 genomic sequence (NC#166E2F2) at nts 29,214-29,242.

TABLE 1

LTVEC Primers and Probes

| Primer | | Sequence Position (5' to 3') | SEQ ID | Size (bp) |
|---|---|---|---|---|
| Primer Pair C1 | Forward Reverse | ttgcattctt ttccaaataa gtgg<br>ttccaggatg aataggataa acagg | 7<br>8 | 81 |
| C1 TAQMAN ™ probe | | atccatcatc actccctgtg tttgtttccc | 9 | |
| Primer Pair C2 | Forward Reverse | agctgactgc tgccgtcag<br>tagactttgt agtgttagaa acatttggaa c | 10<br>11 | 125 |
| C2 TAQMAN ™ probe | | atttttgtaa tgcaatcatg tcaactgcaa tgc | 12 | |
| Primer Pair C3 | Forward Reverse | ctcactctat cccatccaag gg<br>atgggcaggt agcatccaca g | 13<br>14 | 74 |
| C3 TAQMAN ™ probe | | tgaatcatcc ctttgtctag cagaaccgg | 15 | |

Example 2

Humanized IL-7 Mice

Generating Humanized IL-7 Mice.

Donor mouse ES cells comprising a humanized IL-7 locus are introduced into early stage mouse embryos by the VELOCIMOUSE® method (Poueymirou et al. (2007) F0 generation mice fully derived from gene-targeted embryonic stem cells allowing immediate phenotypic analyses, *Nat Biotechnol* 25:91-99). Four F0 mice fully derived from donor ES cells were obtained that were heterozygous for humanization of the endogenous mouse IL-7 locus. F0 mice are bred to homozygosity with respect to the humanization. Homozygous mice are genotyped to confirm homozygosity. All mouse studies were overseen and approved by Regeneron's Institutional Animal Care and Use Committee (IACUC).

Example 3

Expression of Human IL-7 in a Mouse

Figure 2:
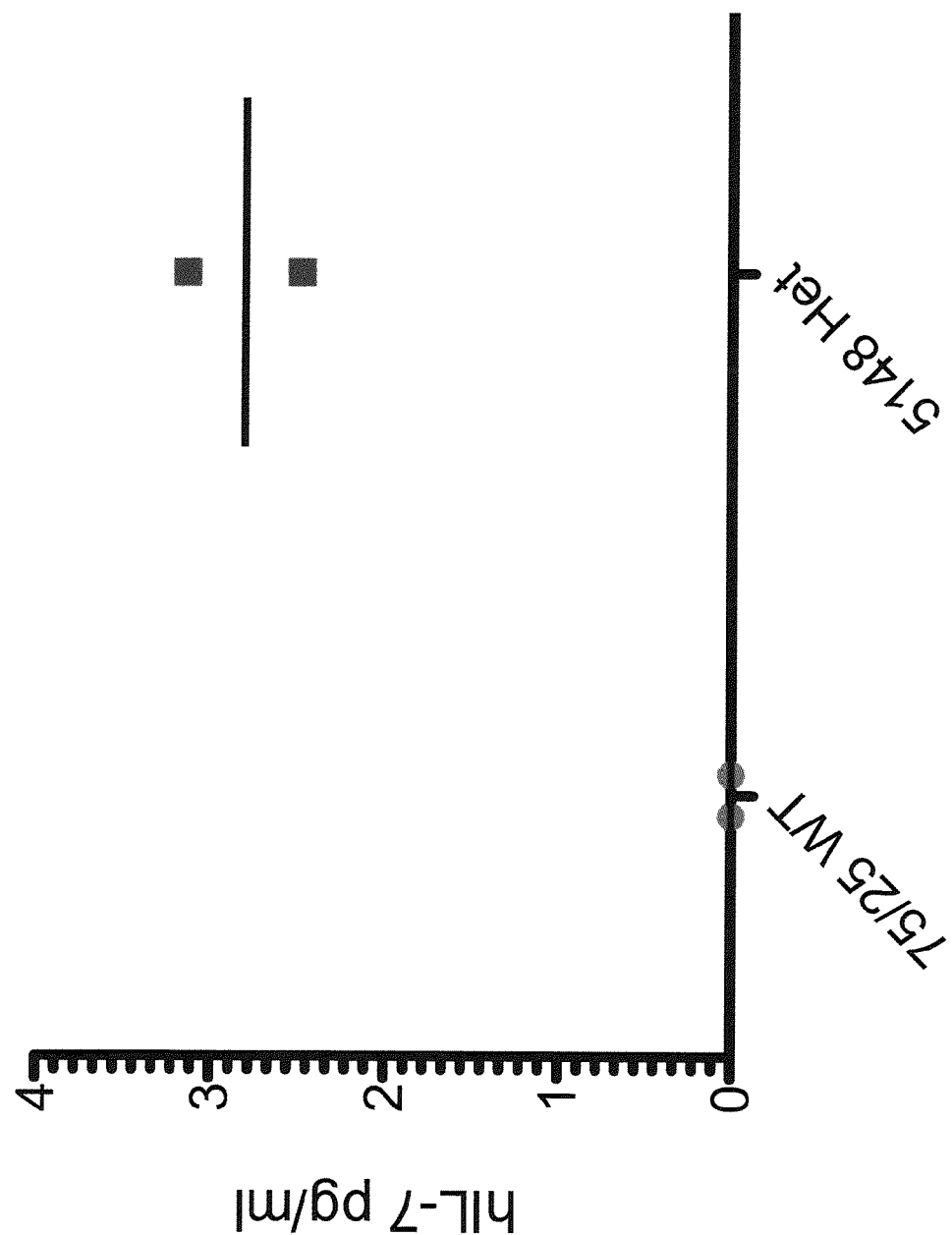
FIG. 2 depicts human IL-7 concentration in serum of wild-type mice that has a genetic background of 75% C57B6 and 25% 129/svJ (75/25 WT) and mice heterozygous for a humanized endogenous IL-7 locus as described herein (5148 Het).

Mice humanized for the IL-7 gene and their non-humanized littermate controls were bled and serum concentrations of human IL-7 were measured using QuantikineHS Human IL-7 Immunoassay kit from R&D Systems, Inc. Data was analyzed using Microsoft Excel and plotted using Prism statistical analysis software. Mice heterozygous for the humanized IL-7 locus (designated MAID 5148 het) expressed human IL-7 in serum at a physiologically relevant concentration. This is in contrast to transgenic human IL-7 mice bearing lentivirally transduced human IL-7 in double knockout mice, which mice exhibit unphysiologically and potentially seriously detrimental high levels of human IL-7 in serum (10 to 100 pg/mL) (O'Connell. R. M. et al. (2010) Lentiviral Vector Delivery of Human Interleukin-7 (hIL-7) to Human Immune System (HIS) Mice Expands T Lymphocyte Populations, PLoS ONE 5(8):e12009). In contrast, mice heterozygous for a humanized endogenous IL-7 locus exhibited about 2.4 to about 3.2 pg/mL in serum (FIG. 2), reflecting normal, or physiologically appropriate, levels of IL-7.

I claim:

1. A mouse whose genome comprises a replacement of at least mouse IL-7 exons 2, 3, 4, and 5 with a human genomic segment comprising human IL-7 exons 2, 3, 4, 5, and 6 to form a human or humanized IL-7-encoding gene, wherein the replacement is at an endogenous mouse IL-7 locus, wherein the human or humanized IL-7-encoding gene is under control of endogenous mouse IL-7 regulatory elements, and wherein the mouse comprises human or humanized IL-7 in serum at a level that is about the same level of endogenous mouse IL-7 in serum of an age matched wild-type mouse.

2. The mouse of claim 1, wherein the level is about 2.4 to about 3.2 pg/mL.

3. The mouse of claim 1, wherein said replacement forms a human IL-7-encoding gene, and wherein the mouse comprises human IL-7 in serum at a level that is about the same level of endogenous mouse IL-7 in serum of an aged-matched wild-type mouse.

4. A method for making a mouse with a human or humanized IL-7-encoding gene, comprising modifying the genome of a mouse by replacing at the endogenous mouse IL-7 gene locus at least mouse exons 2, 3, 4 and 5 of the endogenous mouse IL-7-encoding gene with a human genomic segment comprising human IL-7 exons 2, 3, 4, 5, and 6 to form a human or humanized IL-7-encoding gene, wherein the human or humanized IL-7-encoding gene is under control of endogenous mouse IL-7 regulatory sequences, and wherein the mouse comprises human or humanized IL-7 in serum at a level that is about the same level of endogenous mouse IL-7 in serum of an aged-matched wild-type mouse.

5. The method of claim 4, wherein the level is about 2.4 to about 3.2 pg/mL.

6. The method of claim 4, wherein said human or humanized IL-7 gene encodes human IL-7, and wherein the mouse comprises human IL-7 in serum at a level that is about the same level of endogenous mouse IL-7 in serum of an aged-matched wild-type mouse.

* * * * *